US007288253B2

(12) United States Patent
Roskos et al.

(10) Patent No.: US 7,288,253 B2
(45) Date of Patent: Oct. 30, 2007

(54) ANTIBODIES DIRECTED TO PARATHYROID HORMONE (PTH) AND USES THEREOF

(75) Inventors: Lorin Roskos, Pleasanton, CA (US); Ian Foltz, Burnaby (CA); Chadwick King, Vancouver (CA)

(73) Assignee: Amgen Fremont, Inc., Fremont, CA (US)

( * ) Notice: Subject to any disclaimer, the term of this patent is extended or adjusted under 35 U.S.C. 154(b) by 518 days.

(21) Appl. No.: 10/638,265

(22) Filed: Aug. 8, 2003

(65) Prior Publication Data

US 2005/0031614 A1 Feb. 10, 2005

(51) Int. Cl.
A61K 39/395 (2006.01)
A61K 39/00 (2006.01)
A01N 37/18 (2006.01)

(52) U.S. Cl. .............................. 424/158.1; 424/139.1; 424/142.1; 514/2

(58) Field of Classification Search ..................... None
See application file for complete search history.

(56) References Cited

U.S. PATENT DOCUMENTS

| | | | |
|---|---|---|---|
| 4,341,755 A | 7/1982 | Lindall | |
| 5,077,389 A | 12/1991 | Takahashi | |
| 5,482,706 A | 1/1996 | Igari | |
| 6,001,347 A | 12/1999 | Leone-Bay | |
| 6,030,790 A | 2/2000 | Adermann et al. | |
| 6,642,411 B1 | 11/2003 | Leone-Bay | |
| 6,645,974 B2 | 11/2003 | Hutchinson | |
| 6,646,162 B2 | 11/2003 | Tang | |
| 6,649,161 B1 | 11/2003 | Donovan | |
| 6,649,657 B2 | 11/2003 | Cameron | |
| 6,652,875 B1 | 11/2003 | Bannister | |
| 6,655,379 B2 | 12/2003 | Clark | |
| 6,656,904 B2 | 12/2003 | Mundy | |
| 6,660,715 B2 | 12/2003 | Klibanov | |
| 6,660,760 B1 | 12/2003 | Robl | |
| 6,670,386 B2 | 12/2003 | Sun | |
| 6,673,574 B2 | 1/2004 | Stern | |
| 6,689,118 B2 | 2/2004 | Alchas | |
| 6,689,566 B1 | 2/2004 | Cantor et al. | |
| 6,689,922 B1 | 2/2004 | Bernardon | |
| 6,692,767 B2 | 2/2004 | Burnside | |
| 6,693,208 B2 | 2/2004 | Gscheidner | |
| 6,696,090 B1 | 2/2004 | Nilsson | |
| 6,696,474 B2 | 2/2004 | Bigge | |
| 6,696,550 B2 * | 2/2004 | LaRosa et al. ......... 530/388.23 |
| 6,697,669 B2 | 2/2004 | Dev | |
| 6,699,467 B2 | 3/2004 | Leone-Bay | |
| 6,699,833 B1 | 3/2004 | Gefter | |
| 6,706,289 B2 | 3/2004 | Lewis | |
| 6,713,293 B1 | 3/2004 | Grummt | |
| 6,716,842 B2 | 4/2004 | Fakhoury | |
| 6,720,153 B1 | 4/2004 | Labaudiniere | |
| 6,740,333 B2 | 5/2004 | Beckett | |
| 6,743,590 B1 | 6/2004 | Cantor | |
| 6,750,255 B2 | 6/2004 | Sakai et al. | |
| 6,756,480 B2 | 6/2004 | Kostenuik | |
| 6,767,928 B1 | 7/2004 | Murphy | |
| 6,770,623 B1 | 8/2004 | Chang | |
| 6,828,422 B1 * | 12/2004 | Achim et al. ............... 530/380 |
| 2003/0082179 A1 | 5/2003 | Hutchison | |
| 2003/0206939 A1 | 11/2003 | Bannister | |
| 2003/0208045 A1 | 11/2003 | Yamaguchi | |
| 2003/0216287 A1 | 11/2003 | Tang | |
| 2003/0216589 A1 | 11/2003 | Gschneidner | |
| 2003/0220226 A1 | 11/2003 | Tang | |
| 2003/0220227 A1 | 11/2003 | Gungor | |
| 2003/0220377 A1 | 11/2003 | Chesworth | |
| 2003/0220470 A1 | 11/2003 | Govindan | |
| 2003/0220494 A1 | 11/2003 | Cameron | |
| 2003/0224450 A1 | 12/2003 | Lee | |
| 2003/0225000 A1 | 12/2003 | Chang | |
| 2003/0225300 A1 | 12/2003 | Leone-Bay | |
| 2003/0228275 A1 | 12/2003 | Ekwuribe | |
| 2003/0228652 A1 | 12/2003 | Radhakrishnan | |

(Continued)

FOREIGN PATENT DOCUMENTS

| | | |
|---|---|---|
| EP | 1 197 225 A1 | 4/2002 |
| EP | 1 374 905 A1 | 1/2004 |
| EP | 1 380 589 A1 | 1/2004 |
| EP | 1 393 721 A1 | 3/2004 |
| EP | 1 417 972 A1 | 5/2004 |
| EP | 1 428 524 A1 | 6/2004 |
| EP | 1 431 394 A1 | 6/2004 |
| EP | 1 437 141 A1 | 7/2004 |
| JP | 2000-159799 | 6/2000 |
| WO | WO 03/090723 | 11/2003 |

(Continued)

OTHER PUBLICATIONS

Green L.C. et al. Antigen-specific human monoclonal antibodies from mice engineered with human Ig heavy and light chain YACs. 1994. Nature Genetics. vol. 7, p. 13-21.*

(Continued)

Primary Examiner—Robert S. Landsman
Assistant Examiner—Bruce D Hissong
(74) Attorney, Agent, or Firm—Knobbe Martens Olson & Bear LLP

(57) ABSTRACT

Embodiments of the invention described herein relate to antibodies directed to the antigen parathyroid hormone (PTH) and uses of such antibodies. In particular, in some embodiments, there are provided fully human monoclonal antibodies directed to the antigen PTH. In further embodiments, nucleotide sequences encoding, and amino acid sequences comprising, heavy and light chain immunoglobulin molecules, particularly sequences corresponding to contiguous heavy and light chain sequences spanning the framework regions and/or complementarity determining regions (CDRs), specifically from FR1 through FR4 or CDR1 through CDR3, are provided.

16 Claims, 6 Drawing Sheets

U.S. PATENT DOCUMENTS

| | | |
|---|---|---|
| 2003/0232046 A1 | 12/2003 | Scallon |
| 2003/0232085 A1 | 12/2003 | Milstein |
| 2003/0235612 A1 | 12/2003 | Leone-Bay |
| 2003/0235889 A1 | 12/2003 | Rivera |
| 2004/0001824 A1 | 1/2004 | Yoshida |
| 2004/0002524 A1 | 1/2004 | Chesworth |
| 2004/0002525 A1 | 1/2004 | Robl |
| 2004/0002770 A1 | 1/2004 | King |
| 2004/0005619 A1 | 1/2004 | Karaplis |
| 2004/0009149 A1 | 1/2004 | Altman |
| 2004/0009506 A1 | 1/2004 | Stephan |
| 2004/0014150 A1 | 1/2004 | Bringhurst |
| 2004/0019063 A1 | 1/2004 | Sun |
| 2004/0023847 A1 | 2/2004 | Gschneidner |
| 2004/0028707 A1 | 2/2004 | Pinkerton |
| 2004/0029099 A1 | 2/2004 | Cooper |
| 2004/0029175 A1 | 2/2004 | Comper |
| 2004/0029252 A1 | 2/2004 | Rhee |
| 2004/0029935 A1 | 2/2004 | Robl |
| 2004/0033267 A1 | 2/2004 | Merisko-Liversidge |
| 2004/0033535 A1 | 2/2004 | Boyle |
| 2004/0033950 A1 | 2/2004 | Hock |
| 2004/0037834 A1 | 2/2004 | Woloski |
| 2004/0038865 A1 | 2/2004 | Gelber |
| 2004/0038963 A1 | 2/2004 | Wang |
| 2004/0043003 A1 | 3/2004 | Chen |
| 2004/0043031 A1 | 3/2004 | Hart |
| 2004/0043064 A1 | 3/2004 | Iorio |
| 2004/0043076 A1 | 3/2004 | Dulieu |
| 2004/0043077 A1 | 3/2004 | Brown |
| 2004/0047811 A1 | 3/2004 | Edwards |
| 2004/0048777 A1 | 3/2004 | Weidner |
| 2004/0052862 A1 | 3/2004 | Henriksen |
| 2004/0059282 A1 | 3/2004 | Flock |
| 2004/0062717 A1 | 4/2004 | Rosell |
| 2004/0067231 A1 | 4/2004 | Yoshikawa |
| 2004/0067526 A1 | 4/2004 | Cantor |
| 2004/0072875 A1 | 4/2004 | Torday |
| 2004/0072881 A1 | 4/2004 | Robl |
| 2004/0077528 A1 | 4/2004 | Steiner |
| 2004/0077540 A1 | 4/2004 | Quay |
| 2004/0077573 A1 | 4/2004 | Maruyama |
| 2004/0081652 A1 | 4/2004 | Zack |
| 2004/0082588 A1 | 4/2004 | Evans |
| 2004/0092559 A1 | 5/2004 | Hamann |
| 2004/0092573 A1 | 5/2004 | Robl |
| 2004/0096403 A1 | 5/2004 | Steiner |
| 2004/0097500 A1 | 5/2004 | Liao |
| 2004/0097883 A1 | 5/2004 | Roe |
| 2004/0101482 A1 | 5/2004 | Sanders |
| 2004/0101912 A1 | 5/2004 | Rubin |
| 2004/0102381 A1 | 5/2004 | Ekwuribe |
| 2004/0105839 A1 | 6/2004 | Park |
| 2004/0105889 A1 | 6/2004 | Ryde |
| 2004/0106155 A1 | 6/2004 | Comper |
| 2004/0106773 A1 | 6/2004 | Wang |
| 2004/0106825 A1 | 6/2004 | Bay |
| 2004/0109828 A1 | 6/2004 | Yang |
| 2004/0110735 A1 | 6/2004 | Ekwuribe |
| 2004/0110767 A1 | 6/2004 | Cameron |
| 2004/0110839 A1 | 6/2004 | Leone-Bay |
| 2004/0115167 A1 | 6/2004 | Cormier |
| 2004/0121003 A1 | 6/2004 | Chickering |
| 2004/0121320 A1 | 6/2004 | DePhillipo |
| 2004/0136904 A1 | 7/2004 | Pitcairn |
| 2004/0137032 A1 | 7/2004 | Wang |
| 2004/0138424 A1 | 7/2004 | Takeda |
| 2004/0142919 A1 | 7/2004 | Meissner |
| 2004/0146549 A1 | 7/2004 | Ben-Sasson |
| 2004/0147568 A1 | 7/2004 | Yu |
| 2004/0152094 A1 | 8/2004 | Danielsen |
| 2004/0156826 A1 | 8/2004 | Dangond |
| 2004/0156914 A1 | 8/2004 | Rowe |
| 2004/0157329 A1 | 8/2004 | Roubin |

FOREIGN PATENT DOCUMENTS

| | | |
|---|---|---|
| WO | WO 03/090868 | 11/2003 |
| WO | WO 03/091700 | 11/2003 |
| WO | WO 03/092588 | 11/2003 |
| WO | WO 03/092685 | 11/2003 |
| WO | WO 03/093314 | 11/2003 |
| WO | WO 03/096980 | 11/2003 |
| WO | WO 03/099852 | 12/2003 |
| WO | WO 03/100015 | 12/2003 |
| WO | WO 03/100026 | 12/2003 |
| WO | WO 03/102132 | 12/2003 |
| WO | WO 03/102230 | 12/2003 |
| WO | WO 03/102593 | 12/2003 |
| WO | WO 03/104449 | 12/2003 |
| WO | WO 03/105772 | 12/2003 |
| WO | WO 2004/000817 | 12/2003 |
| WO | WO 2004/000867 | 12/2003 |
| WO | WO 2004/003145 | 1/2004 |
| WO | WO 2004/003204 | 1/2004 |
| WO | WO 2004/006907 | 1/2004 |
| WO | WO 2004/007675 | 1/2004 |
| WO | WO 2004/009774 | 1/2004 |
| WO | WO 2004/011599 | 2/2004 |
| WO | WO 2004/012672 | 2/2004 |
| WO | WO 2004/014411 | 2/2004 |
| WO | WO 2004/016151 | 2/2004 |
| WO | WO 2004/019853 | 3/2004 |
| WO | WO 2004/019884 | 3/2004 |
| WO | WO 2004/019886 | 3/2004 |
| WO | WO 2004/021984 | 3/2004 |
| WO | WO 2004/022033 | 3/2004 |
| WO | WO 2004/024758 | 3/2004 |
| WO | WO 2004/026231 | 4/2004 |
| WO | WO 2004/026290 | 4/2004 |
| WO | WO 2004/026823 | 4/2004 |
| WO | WO 2004/028339 | 4/2004 |
| WO | WO 2004/028379 | 4/2004 |
| WO | WO 2004/028444 | 4/2004 |
| WO | WO 2004/030669 | 4/2004 |
| WO | WO 2004/030743 | 4/2004 |
| WO | WO 2004/031727 | 4/2004 |
| WO | WO 2004/041277 | 5/2004 |
| WO | WO 2004/041755 | 5/2004 |
| WO | WO 2004/043442 | 5/2004 |
| WO | WO 2004/044007 | 5/2004 |
| WO | WO 2004/045518 | 6/2004 |
| WO | WO 2004/045592 | 6/2004 |
| WO | WO 2004/047751 | 6/2004 |
| WO | WO 2004/048409 | 6/2004 |
| WO | WO 2004/052340 | 6/2004 |
| WO | WO 2004/052405 | 6/2004 |
| WO | WO 2004/053080 | 6/2004 |
| WO | WO 2004/057002 | 7/2004 |
| WO | WO 2004/057333 | 7/2004 |
| WO | WO 2004/060344 | 7/2004 |
| WO | WO 2004/060473 | 7/2004 |
| WO | WO 2004/060920 | 7/2004 |
| WO | WO 2004/062588 | 7/2004 |
| WO | WO 2004/064758 | 8/2004 |
| WO | WO 03/099853 | 12/2004 |
| WO | WO 2005/016111 A2 | 2/2005 |

OTHER PUBLICATIONS

Babcook et al., "A novel strategy for generating monoclonal antibodies from single, isolated lymphocytes producing antibodies of defined specificites," *Proc. Natl. Acad. Sci. USA*, 93: 7843-7848 (1996).

Bradwell et al., "Control of hypercalcaemia of parathyroid carcinoma by immunisation," *Lancet*, 353: 370-373 (1999).

Duvos et al., "The (18-48)-Fragment of Human Parathyroid Hormone Is a Partial Agonist for cAMP-Dependent Actions With Retained Mitogenic Function," *Bone*, 17: 403-406 (1995).

Logue et al., "Production and characterisation of monoclonal antibodies to parathyroid hormone (1-34)," *J. Immunol. Methods*, 137: 159-166 (1991).

Magerlein et al., "Production of Sequence Specific Polyclonal Antibodies to Human Parathyroid Hormone 1-37 by Immunization with Multiple Antigenic Peptides," *Drug Res.*, 48: 783-787 (1998).

Vieira et al., "Monoclonal Antibodies to Bovine Parathyroid Hormone: Production and Characterization," *Braz. J. Med. Biol. Res.*, 21: 1005-1011 (1988).

Visser et al., "Production and Characterization of Antisera to Synthetic 1-34 Human Parathyroid Hormone Fragments: Possible Implications for the Correctness of Proposed Structures," *Acta Endocrinol.*, 90: 90-102 (1979).

Immunology, 5$^{th}$ Edition. pp. 1 and Chapter 14 (p. 188-197). Roitt, Brostoff, and Male, eds. Mosby Int. (publisher). 1998.

Errazahi et al. (2003) Functional type I PTH/PTHrP receptor in freshly isolated newborn rat keratinogytes: identification by RT-PCR and immunohistochemistry. Journal of Bone and Mineral Research. 18(4):737-750.

Gardella et al. (1993) Analysis of parathyroid hormones's principal receptor-binding region by site-directed mutagenesis and analog design. Endocrinology. 132(5):2024-2030.

Nussbaum et al. (1982) Monoclonal antibodies directed against the biologically active region parathyroid hormone. Abstract-XP-001094830.

* cited by examiner

FIG. 3A

| SEQ ID NO. | Single cell | Well | V Heavy (D/J) | FR1 | CDR1 | FR2 |
|---|---|---|---|---|---|---|
| - | - | - | Germline | EVQLVESGGGLVKPGGSLRLSCAAS | GFTFSNAWMS | WVRQAPGKGLEWVG |
| 26 | 11 | 133A8 | VH3-15/DIR3/JH4b | ------------------------ | ---------- | ---D---------- |
| 10 | 57 | 119G2 | | ------E----------------- | ---------- | -------------- |
| 30 | 86 | 133D2 | | ------------------------ | ---------- | ---D---------- |
| 70 | 113 | 126H9 | | --------M--------------- | ---------- | -------------- |
| 42 | 96 | 143C7 | | ------------------------ | ---------- | -------------- |
| 14 | 45 | 132B12 | | ------------------------ | -----R---- | -------------- |
| 34 | 124 | 135H11 | | ------------------------ | ---------- | -------------- |
| 22 | 140 | 132G12 | | ----------T------------- | -------L-- | -------------- |
| 66 | 163 | 130A1 | | ------------------------ | ----S----- | -------------- |
| 6 | 262 | 284D9 | | ------------------------ | ----L----- | -------------- |
| 58 | 195 | 277F10 | | -M---------------------- | -S-----N-- | -------------- |
| 54 | 225 | 275A4 | VH3-15/DIR1/JH4b | ------------------------ | ---------- | -------------- |
| 50 | 214 | 267D10 | | ------------------------ | ---------- | -------------- |
| 46 | 238 | 264E5 | VH3-15/D21-9/JH4b | ------------------------ | ---------- | -------------- |
| 38 | 275 | 141G11 | | ------------------------ | ---------- | -------------- |
| - | - | - | Germline | EVQLVQSGAEVKKPGESLKISCKGS | GYSFTSYWIG | WVRQMPGKGLEWMG |
| 2 | 183 | 292A10 | VH5-51/D21-10/JH4b | ------------------------ | R-I-N----- | -------------- |
| 62 | 168 | 302A7 | | ------------------------ | ---------- | -------------- |
| - | - | - | Germline | QVQLVQSGGGVVQPGRSLRLSCAAS | GFTFSSYGMH | WVRQAPGKGLEWVA |
| 18 | 26 | 126B1 | VH3-30/DIR3/JH4b | ------------------------ | ---------- | ---D---------- |
| - | - | - | Germline | EVQLVESGGGLVQPGGSLRLSCAAS | GFTFSSYDMH | WVRQATGKGLEWVS |
| 74 | 302 | 130C6 | VH3-13/D6-6/JH4b | ---D-------------------- | ---------Y | -------------- |

| CDR2 | FR3 | CDR3 | FR4 |
|---|---|---|---|
| RIKSKTDGGTTDYAAPVKG | RFTISRDDSKNTLYLQMNSLKTEDTAVYYCTT | GATFDS | WGQGTLVTVSS |
| ------------------- | -------------------------------- | GATFDS | ----------- |
| ------------------- | -------------------------------- | GATFDS | ----------- |
| ------------------- | --------------K--------------- | GATFDS | ----------- |
| ------------------- | -------------------------------- | GATFDS | ----------- |
| ------------------- | ------------E------------------ | GATFDS | ----------- |
| ------------------- | -------------------------L------ | GATFDC | ----------- |
| ------------------- | -----------------G-------------- | GATFDS | ----------- |
| ------------------- | ------------T------------------- | GATFDS | ----------- |
| -------S----------- | ------------V------------------- | GATFDS | ----------- |
| ------------------- | ------------F------------------- | GATFDS | ----------- |
| --------N---------- | ----------------N--------------- | GAVLDY | ----------- |
| --------R---A------ | ------S---E-------------H-S---- | YYFDSSGFPFDY | -----S----- |
| --------S---------- | ---------------L-K-------------- | YYFDSSGFPFDY | -----S----- |
| ------------------- | -------------------------------- | YYFDSSGFPFDY | -----S----- |
| ------------------- | -------------------------------- | YYFDSSGFPFDY | -----S----- |
| IIYPGDSDTRYSPSFQG | QVTISADKSISTAYLQWSSLKASDTAMYYCAR | QGDYVWGSYDS | WGQGTLVTVSS |
| ---S------------- | --------------M----------------- | QGDYVWGSFDS | ----------- |
| VISYDGSNKYYADSVKG | RFTISRDNSKNTLYLQMNSLRAEDTAVYYCAR | DHWELLDY | WGQGTLVTVSS |
| ------F---------- | -------------------------------- |  | ----------- |
| AIGTAGDTYYPGSVKG | RFTISRENAKNSLYLQMNSLRAGDTAVYYCAR | GEQFVRGLFDY | WGQGTLVTVSS |

FIG. 4A

| SEQ ID NO. | Single cell | Well | V kappa/J | FR1 | CDR1 | FR2 |
|---|---|---|---|---|---|---|
| | | | Germline | DIVMTQSPLSLPVTPGEPASISC | RSSQSLLHSNGYNYLD | WYLQKPGQSPQLLIY |
| 28 | 11 | 133A8 | A3/JK1 | ---------------------- | -----KF-------- | -F------------- |
| 12 | 57 | 119G2 | | ---------------------- | ---Y---K------- | -F------------- |
| 32 | 86 | 133D2 | | ---------------------- | -----K--------- | -F------------- |
| 72 | 113 | 126H9 | | ---------------------- | -----KF-------- | -F------------- |
| 44 | 96 | 143C7 | | ---------------------- | ---R----------- | -F------------- |
| 16 | 45 | 132B12 | | ---------------------- | ---------KF---- | -F------------- |
| 36 | 124 | 135H11 | | ---------------------- | ---Y---FK------ | -F------------- |
| 24 | 140 | 132G12 | | ---------------------- | ---------KF---- | -F------------- |
| 68 | 163 | 130A1 | | ---------------------- | ---R-----K----- | ---------------- |
| 8 | 262 | 284D9 | | ---------------------- | ---------K----- | -F------------- |
| | | | Germline | DIVMTQSPLSLPVTPGEPASISC | RSSQSLLHSNGYNYLD | WYLQKPGQSPQLLIY |
| 56 | 225 | 275A4 | A3/JK4 | ---------------------- | ---------K---E- | ---------------- |
| 52 | 214 | 267D10 | | ---------------------- | ---------K---E- | ---------------- |
| 48 | 238 | 264E5 | | ---------------------- | ---------K---E- | --------------V- |
| 40 | 275 | 141G11 | | ---------------------- | ---------K---E- | ---------------- |
| 60 | 195 | 277F10 | | ---------------------- | ---N--R------E- | ---------------- |
| | | | Germline | DIVMTQTPLSLSVTPGQPASISC | KSSQSLLHSDGKTYLY | WYLQKPGQPPQLLIY |
| 4 | 183 | 292A10 | A2/JK1 | ---------------------- | --------D------ | ---------------- |
| 64 | 168 | 302A7 | | ---------------------- | --------D------ | ---------------- |
| | | | Germline | DIVMTQTPLSLSVTPGQPASISC | KSSQSLLHSDGKTYLY | WYLQKPGQPPQLLIY |
| 20 | 26 | 126B1 | A2/JK3 | ---------------------- | --------D------ | -----RS-H------- |
| | | | Germline | DIQMTQSPSSVSASVGDRVTITC | RASQGISSWLA | WYQQKPGKAPKLLIY |
| 76 | 302 | 130C6 | L5/JK3 | ---------------------- | ----------- | ---------------- |

| CDR2 | FR3 | CDR3 | FR4 |
|---|---|---|---|
| LGSNRAS | GVPDRFSGSGSGTDFTLKISRVEAEDVGVYYC | MQALQTPWT | FGQGTKVEIK |
| ---Y--- | -------R----------------------- | --------- | ---------- |
| ---Y--- | ------------------------------- | --------- | ---------- |
| ---Y-V- | -------R----------------------- | --------- | ---------- |
| ---Y--- | ----------------I-------------- | ---R----- | ---------- |
| ---Y--- | ---------------T--------------- | --------- | ---------- |
| ---Y--- | --------------S---------------- | --------- | ---------- |
| ---I--- | ------------------------------- | --------- | ---------- |
| LGSNRAS | GVPDRFSGDGDGTDFTLKISRVEAEDVGVYYC | MQALQTPLT | FGGGTKVEIK |
| ------- | ------------------------------- | ---T--I-- | ---------- |
| ------- | ------------S------------------ | ---T--I-- | ---------- |
| ------- | ------------------------------- | ---T--I-- | ---------- |
| ------- | ------------------------------- | ---S----- | ---------- |
| EVSNRFS | GVPDRFSGSGSGTDFTLKISRVEAEDVGVYYC | MQSIQLWT | FGQGTKVEIK |
| ------- | -------R----------------I-F---- | ---P--H-- | ---------- |
| EVSNRFS | GVPDRFSGSGSGTDFTLKISRVEAEDVGVYYC | MQSIQLPFT | FGPGTKVDIK |
| ---Y-I- | -------------------------A----- | --GK-F--I | ---------- |
| AASSLQS | GVPSRFSGSGSGTDFTLTISSLQPEDFATYYC | QQANSFPFT | FGPGTKVDIK |
| ---I--- | -------------------------------- | --------- | ---------- |

ANTIBODIES DIRECTED TO PARATHYROID HORMONE (PTH) AND USES THEREOF

BACKGROUND OF THE INVENTION

1. Field of the Invention

Embodiments of the invention described herein relate to antibodies directed to the antigen parathyroid hormone (PTH) and uses of such antibodies. In particular, in accordance with embodiments of the invention described herein, there are provided fully human monoclonal antibodies (mAbs) directed to the antigen PTH. Nucleotide sequences encoding, and amino acid sequences comprising, heavy and light chain immunoglobulin molecules, particularly sequences corresponding to contiguous heavy and light chain sequences spanning the framework regions and/or complementarity determining regions (CDRs), specifically from FR1 through FR4 or CDR1 through CDR3, are provided. The antibodies of the invention find use as diagnostics and as treatments for diseases associated with the overproduction of PTH.

2. Description of the Related Art

Parathyroid glands are part of the endocrine system and produce parathyroid hormone (PTH). PTH regulates the levels of calcium, phosphorus, and magnesium, in the bloodstream, maintaining an appropriate balance of these substances, which is essential for normal bone mineralization. Chronic, excessive production of PTH is known as hyperparathyroidism (HPT). Overproduction of parathyroid hormone leads to an elevated blood calcium level and decreased blood phosphate level. Calcium is removed from bones and calcium absorption from the gastrointestinal (GI) tract increases. The kidneys attempt to compensate for the increased blood calcium level by secreting excess calcium in the urine, which can result in the formation of kidney stones. The effects of increased PTH levels are seen not only in the kidneys, but also in the skeleton, stomach and intestines, the nervous system, and the muscles (R. S. Cotran et al., eds., *Robbins Pathologic Basis of Disease* 124-647 (4th ed., W.B. Saunders Co., Philadelphia 1989).

In primary hyperparathyroidism, the increased secretion of PTH occurs because of the presence of a tumor, a parathyroid adenoma (~80%), or less commonly by hyperplasia of the parathyroid (~15%) or carcinoma (~5%). As a result of elevated blood calcium levels, symptoms can include kidney stones, bone pain, fatigue, anorexia, nausea and vomiting (L. M. Tierney, Jr., et al., eds., *Current Medical Diagnosis and Treatment* 1001-02 (35th ed., Appleton & Lange, Stamford, Conn. 1996)). Current medical management of primary HPT is not satisfactory because presently, there are no agents that can produce sustained blockage of PTH release by the parathyroid glands. Surgical removal of part or all of the parathyroid glands is the preferred treatment, although complications such as damage to the laryngeal nerve and prolonged hypocalcemia can occur postoperatively.

In secondary hyperparathyroidism, the excess production of PTH is normally a result of either vitamin D deficiencies (rickets and osteomalacia) or chronic renal failure (CRF). When secondary HPT is due to renal failure, the pathology is characterized by hypocalcemia and hyperphosphatemia and a relative inability to respond to PTH. This resistance to PTH function leads to hyperplasia of the parathyroid glands and excessive production of PTH as the glands try to re-establish normocalcemia and normophosphatemia. The resistance to PTH levels is due to a failure to produce calcitriol (active form of vitamin D) in the kidneys and a failure to excrete phosphate through the kidneys. Calcitriol acts directly on parathyroid glands to inhibit PTH production and the GI tract to promote calcium absorption. Therefore the loss of calcitriol leads to increased serum PTH levels. High phosphate levels also act directly on parathyroid tissue to induce the expression of PTH and can interact directly with calcium to maintain hypocalcemia. The loss of these negative feedback mechanisms account for most of the resistance to PTH seen in CRF (Fauci, A. S. et al., eds., *Harrison's Principles of Internal Medicine* 2214-47 (14th ed., McGraw-Hill Co. 1998)). In severe secondary HPT, extremely high levels of PTH overwhelm the bone's resistance to the hormone resulting in high serum calcium and phosphate levels that may cause diffuse calcification in the skin, soft tissues, and arteries (calciphylaxis). Such calcification can result in painful ischemic necrosis of the skin and gangrene, cardiac arrhythmias, and pulmonary failure (Tierney et al., supra at 1003).

Currently, secondary HPT is treated medically with phosphate binders such as calcium carbonate and with supraphysiological levels of vitamin D analogues such as calcitriol and doxercalciferol. Not all patients respond to calcitriol and hypercalcemia is a common complication of treatment (Felsenfeld, A. J., *J. Am. Soc. Nephrology* 8(6): 993-1004 (1997)). Calcimimetics, designed as allosteric modulators of the calcium receptor, are also in clinical development as a possible therapy.

PTH is an 84-amino-acid peptide secreted from the parathyroid glands. Its amino acid sequence (Keutman, H. T. et al., *Biochemistry* 17:5723-29 (1978)) and the nucleotide sequence of the related gene (Hendy et al., *Proc. Natl. Acad. Sci. USA* 78:7365-69 (1981)) are known. PTH acts through the PTH/parathyroid-related protein (PTHrP) receptor to promote bone resorption and decrease calcium excretion. Human parathyroid hormone (hPTH) circulates as substantially intact hPTH1-84 and fragments thereof. Full length hPTH1-84 and fragment hPTH1-34 are believed to be biologically active, while fragment hPTH35-84 is believed to be inactive. Fragments lacking the N-terminus of PTH (hPTH7-84 or hPTH7-34) are not only inactive, but can also inhibit biologically active PTH in vivo (Horiuchi et al., *Science* 220:1053-55 (1983)).

Lindall, in U.S. Pat. No. 4,341,755, describes an antibody radioimmunoassay of PTH in mammalian serum. A chicken antibody with a high affinity for the 65-84 portion of human PTH was utilized in the assay. Adermann et al., in U.S. Pat. No. 6,030,790, disclose polyclonal antibodies made by injecting unspecified animals with various fragments of hPTH1-37, which are useful in assays of biologically active PTH. Japan Tobacco, Inc., in Japanese Patent Application No. JP 98337263, filed Nov. 27, 1998, discloses human monoclonal antibodies with reactivity to human PTH or its fragments. However, the disclosed antibodies do not appear to be therapeutically useful, likely due to the fact that the affinities of such antibodies to human PTH are insufficient.

The obstacles to developing a monoclonal or polyclonal antibody to PTH for therapeutic applications have been described and have been attributed to inadequate affinity and immunogenicity (Bradwell, A. R. et al., *Lancet* 353:370-73 (1999)). Bradwell et al. successfully immunized a patient suffering from parathyroid carcinoma with PTH and the patient produced autoantibodies against PTH. However, due to the clinical need to titrate PTH to an individual target range in the hyperparathyroid patient population, a clinical immunization approach would not be generally applicable given the heterogeneity of immune responses and the need to break tolerance to a self antigen. Thus, the unmet need for a therapeutically useful anti-PTH antibody remains.

SUMMARY OF THE INVENTION

The invention described herein relates to monoclonal antibodies that bind PTH and affect PTH function. Accordingly, embodiments of the invention provide human anti-PTH antibodies and anti-PTH antibody preparations with desirable properties from diagnostic and therapeutic perspectives. In particular, one embodiment of the invention provides anti-PTH antibodies having characteristics that provide therapeutic utility, including, for example, but not limited to, strong binding affinity for PTH, the ability to neutralize PTH in vitro, and the ability to produce prolonged neutralization of PTH in vivo.

One embodiment of the invention is a fully human monoclonal antibody that binds to PTH and has a heavy chain amino acid sequence selected from the group consisting of SEQ ID NOS: 2, 6, 10, 14, 18, 22, 26, 30, 34, 38, 42, 46, 50, 54, 58, 62, 66, 70, 74 and 78. In one embodiment, the antibody further comprises a light chain amino acid sequence selected from the group consisting of SEQ ID NOS: 4, 8, 12, 16, 20, 24, 28, 32, 36, 40, 44, 48, 52, 56, 60, 64, 68, 72, 76 and 80.

Another embodiment of the invention is an isolated human monoclonal antibody having a heavy chain variable region sequence comprising SEQ ID NO: 2 and a light chain variable region sequence comprising SEQ ID NO: 4.

Another embodiment of the invention is a fully human antibody that binds to PTH that comprises a heavy chain amino acid sequence having the CDRs comprising the sequences shown in FIG. 3. It is noted that CDR determinations can be readily accomplished by those of ordinary skill in the art. In general, CDRs are presented in the invention described herein as defined by Kabat et al., in *Sequences of Proteins of Immunological Interest* vols. 1-3 (Fifth Edition, NIH Publication 91-3242, Bethesda Md. 1991).

Yet another embodiment of the invention is a fully human antibody that binds to PTH and comprises a light chain amino acid sequence having the CDRs comprising the sequences shown in FIG. 4.

A further embodiment of the invention is a fully human antibody that binds to PTH and comprises a heavy chain amino acid sequence having the CDRs comprising the sequences shown in FIG. 3 and a light chain amino acid sequence having the CDRs comprising the sequences shown in FIG. 4.

Another embodiment of the invention is an isolated high affinity anti-PTH antibody. In a further embodiment of the invention, a single dose of such high affinity antibody produces a reduction of unbound PTH levels in serum from hyperthyroid levels to a normal or near-normal level for 24 to 36 hours, preferably 48 to 60 hours, more preferably 72 to 84 hours. Another embodiment of the invention is an anti-PTH antibody that reduces the level of unbound PTH in normal Sprague-Dawley rats receiving 50 µg/kg/day human PTH(1-34) by subcutaneous Alzet osmotic pump by at least 50% for at least 48 hours following a single 3 mg/kg intravenous dose of antibody, as measured by direct assay or by a biomarker of PTH bioactivity.

A further embodiment of the invention is an antibody that cross-competes for binding to PTH with the fully human antibodies of the invention. In another embodiment of the invention, the fully human antibody is the Anti-PTH mAb 183.

Embodiments of the invention described herein are based upon the generation and identification of isolated antibodies that bind specifically to PTH. PTH is expressed at elevated levels in hyperthyroidism. Inhibition of the biological activity of PTH can delay the progression of symptoms caused by primary hyperthyroidism and secondary hyperthyroidism.

Accordingly, one embodiment of the invention described herein provides isolated antibodies, or fragments of those antibodies, that bind to PTH. As known in the art, the antibodies can advantageously be, for example, monoclonal, chimeric and/or human antibodies. Embodiments of the invention described herein also provide cells for producing these antibodies.

It will be appreciated that embodiments of the invention are not limited to any particular form of an antibody or method of generation or production. For example, the anti-PTH antibody may be a full-length antibody (e.g., having an intact human Fc region) or an antibody fragment (e.g., a Fab, Fab' or F(ab')$_2$). In addition, the antibody may be manufactured from a hybridoma that secretes the antibody, or from a recombinantly produced cell that has been transformed or transfected with a gene or genes encoding the antibody.

Other embodiments of the invention include isolated nucleic acid molecules encoding any of the antibodies described herein, vectors having an isolated nucleic acid molecules encoding any of such the anti-PTH antibodies, a host cell transformed with any of such nucleic acid molecules. In addition, one embodiment of the invention is a method of producing an anti-PTH antibody by culturing host cells under conditions wherein a nucleic acid molecule is expressed to produce the antibody followed by recovering the antibody.

A further embodiment of the invention includes a method of producing high affinity antibodies to PTH by immunizing a mammal with human PTH or a fragment thereof and one or more orthologous sequences or fragments thereof.

Another embodiment of the invention includes a method of diagnosing diseases or conditions in which an antibody prepared according to the invention described herein is utilized to detect the level of PTH in a patient sample. In one embodiment, the patient sample is blood or blood serum. In further embodiments methods for the identification of risk factors, diagnosis of disease, and staging of disease is presented which involves the identification of the overexpression of PTH using anti-PTH antibodies, such as mAb 183 discussed in detail below.

Other embodiments of the invention include pharmaceutical compositions comprising an effective amount of the antibody of the invention in admixture with a pharmaceutically acceptable carrier or diluent. In yet other embodiments, the anti-PTH antibody or fragment thereof is conjugated to a therapeutic agent. The therapeutic agent can be a toxin or a radioisotope. Preferably, such antibodies can be used for the treatment of diseases, such as, for example, primary and secondary hyperparathyroidism.

In yet another embodiment, a method for treating diseases or conditions associated with the overexpression of PTH in a patient is provided, comprising administering to the patient an effective amount of an anti-PTH antibody. In one embodiment, the patient is a mammalian patient, preferably a human patient. In another embodiment, the method comprises the treatment of primary and secondary hyperparathyroidism.

In another embodiment, the invention includes an assay kit for the detection of PTH in mammalian tissues or cells to screen for hyperparathyroidism, comprising an antibody that binds to PTH and a means for indicating the reaction of the antibody with the antigen, if present. Preferably the antibody is a monoclonal antibody. In one embodiment, the antibody that binds PTH is labeled. In another embodiment the antibody is an unlabeled first antibody and the means for indicating the reaction comprises a labeled second antibody that is an anti-immunoglobulin. Preferably the antibody is labeled with a marker selected from the group consisting of a fluorochrome, an enzyme, a Radionuclide and a radiopaque material.

In still another embodiment, the invention includes a method for treating diseases or conditions associated with the overexpression of PTH in a patient, comprising administering to the patient an effective amount of an anti-PTH antibody. The method can be performed in vivo. Additional embodiments include methods for the treatment of diseases and conditions associated with the overexpression of PTH, which can include identifying a mammal in need of treatment for overexpression of PTH and administering to the mammal, a therapeutically effective dose of anti-PTH antibodies. In another embodiment, the invention provides an article of manufacture comprising a container, comprising a composition containing an anti-PTH antibody, and a package insert or label indicating that the composition can be used to treat hyperparathyroidism characterized by the overexpression of PTH. Preferably a mammal, and more preferably, a human receives the anti-PTH antibody. In a preferred embodiment, primary and secondary hyperparathyroidism are treated.

Additionally, the nucleic acids described herein, and fragments and variants thereof, may be used, by way of nonlimiting example, (a) to direct the biosynthesis of the corresponding encoded proteins, polypeptides, fragments and variants as recombinant or heterologous gene products, (b) as probes for detection and quantification of the nucleic acids disclosed herein, (c) as sequence templates for preparing antisense molecules, and the like. Such uses are described more fully in the following disclosure.

Furthermore, the proteins and polypeptides described herein, and fragments and variants thereof, may be used, in ways that include (a) serving as an immunogen to stimulate the production of an anti-PTH antibody, (b) a capture antigen in an immunogenic assay for such an antibody, (c) as a target for screening for substances that bind to a PTH polypeptide described herein, and (d) a target for a PTH specific antibody such that treatment with the antibody affects the molecular and/or cellular function mediated by the target.

In some embodiments, the anti-PTH antibody is administered, followed by a clearing agent to remove circulating antibody from the blood.

In some embodiment, anti-PTH antibodies can be modified to enhance their capability of fixing complement and participating in complement-dependent cytotoxicity (CDC). In one embodiment, the anti-PTH antibody can be modified, such as by an amino acid substitution, to alter antibody clearance. For example, certain amino acid substitutions may accelerate clearance of the antibody from the body. Alternatively, the amino acid substitutions may slow the clearance of antibody from the body. In other embodiments, the anti-PTH antibody can be altered such that it is eliminated less rapidly from the body.

Yet another embodiment is the use of an anti-PTH antibody in the preparation of a medicament for the treatment of diseases such as hyperparathyroidism. In one embodiment, the disease is primary hyperthyroidism. In an alternative embodiment, the disease is secondary hyperparathyroidism. Still another embodiment is the use of an anti-PTH antibody in the preparation of a medicament for reducing the level of circulating PTH in an animal.

BRIEF DESCRIPTION OF THE DRAWINGS

FIG. 3A is an amino acid sequence alignment of heavy chain variable regions of anti-PTH mAbs generated according to the invention with their associated germline variable region sequences.

FIG. 3B is an amino acid sequence alignment of heavy chain variable regions of anti-PTH mAbs generated according to the invention with their associated germline variable region sequences.

FIG. 4A is an amino acid alignment of light chain variable regions of anti-PTH mAbs generated according to the invention with their associated germline variable region sequences.

FIG. 4B is an amino acid alignment of light chain variable regions of anti-PTH mAbs generated according to the invention with their associated germline variable region sequences.

DETAILED DESCRIPTION OF THE PREFERRED EMBODIMENT

Figure 1:
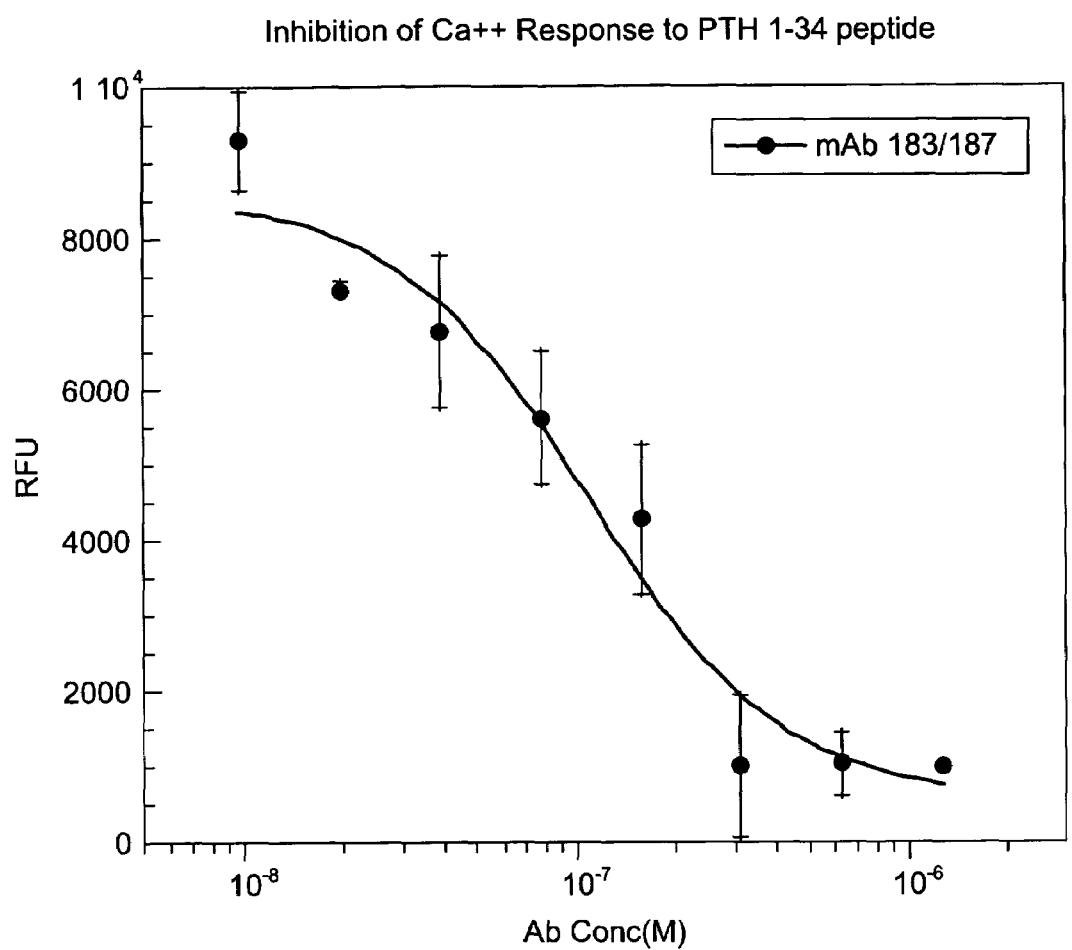
FIG. 1 is a graph showing neutralization data for anti-PTH mAb 183 as determined by calcium mobilization assay on FLuorometric Imaging Plate Reader (FLIPR).

Embodiments of the invention described herein relate to fully human anti-PTH antibodies and their uses. Such fully human antibodies have the advantage of improved pharmacokinetic and safety profiles relative to antibodies containing non-human sequences and, accordingly, immunogenicity in humans is not anticipated. Through use of a dual-antigen immunization strategy combined with the screening technology described herein, monoclonal antibodies with rare affinity and prolonged duration of action in vivo have been discovered that have utility in therapeutic applications. Additionally, the in vivo neutralization studies provided herein demonstrate that for an anti-PTH antibody to be highly therapeutically viable, it should possess high affinity, preferably in the nanomolar range and more preferably in the picomolar range. The anti-PTH antibodies of the invention described herein have been found to preferentially and specifically bind to PTH.

Accordingly, embodiments of the invention provide isolated antibodies, or fragments of those antibodies, that bind to PTH. As known in the art, the antibodies can advantageously be, e.g., monoclonal, chimeric and/or human antibodies. Embodiments of the invention also provide cells for producing these antibodies.

In addition, embodiments of the invention provide for using these antibodies as a diagnostic or treatment for disease. For example, embodiments of the invention provide methods and antibodies for inhibition expression of PTH associated with hyperparathyroidism. Preferably, the antibodies are used to treat primary and secondary hyperthyroidism. In association with such treatment, articles of manufacture comprising antibodies of the invention described herein are provided. Additionally, an assay kit comprising antibodies in accordance with the invention described herein is provided to screen for hyperthyroidism.

Antibodies of the invention described herein, such as anti-PTH mAb 183 antibody, possess high affinity, significant neutralization potential, and sustained half-life and prolonged duration of action. Anti-PTH antibodies in accordance with the invention described herein, such as anti-PTH mAb 183 antibody, reduce the level of unbound PTH in normal Sprague-Dawley rats receiving 50 µg/kg/day human PTH(1-34) by subcutaneous Alzet osmotic pump by at least 50% for at least 48 hours following a single 3 mg/kg intravenous dose of antibody, as measured by direct assay or by a biomarker of PTH bioactivity.

Accordingly, antibodies of the invention described herein possess therapeutic utilities. For example, a single dose of antibodies in accordance with the invention, such as anti-PTH mAb 183 antibody, will produce a reduction of unbound PTH levels in serum of a patient from hyperthyroid levels to a normal or near-normal level for 24 to 36 hours, preferably 48 to 60 hours, and more preferably 72 to 84 hours. Similarly, administration of at least one dose of an anti-PTH antibody of the invention, such as anti-PTH mAb 183 antibody, is capable of reducing circulating PTH levels in a patient by about 25%, preferably by about 50%, and more preferably by about 75% relative to the levels prior to administration and preferably maintain such reduction for a period of about 24 to 36 hours, preferably for a period of about 48 to 60 hours, and more preferably for a period of about 72 to 84 hours.

Further embodiments, features, and the like regarding the antibodies of the invention are provided in additional detail below.

Sequence Listing

The heavy chain and light chain variable region nucleotide and amino acid sequences of representative human anti-PTH antibodies are provided in the sequence listing, the contents of which are summarized in Table 1 below.

TABLE 1

| mAb ID No.: | Sequence | SEQ ID NO: |
|---|---|---|
| 183 | Nucleotide sequence encoding the variable region of the heavy chain | 1 |
| | Amino acid sequence encoding the variable region of the heavy chain | 2 |
| | Nucleotide sequence encoding the variable region of the light chain | 3 |
| | Amino acid sequence encoding the variable region of the light chain | 4 |
| 262 | Nucleotide sequence encoding the variable region of the heavy chain | 5 |
| | Amino acid sequence encoding the variable region of the heavy chain | 6 |
| | Nucleotide sequence encoding the variable region of the light chain | 7 |
| | Amino acid sequence encoding the variable region of the light chain | 8 |
| 57 | Nucleotide sequence encoding the variable region of the heavy chain | 9 |
| | Amino acid sequence encoding the variable region of the heavy chain | 10 |
| | Nucleotide sequence encoding the variable region of the light chain | 11 |
| | Amino acid sequence encoding the variable region of the light chain | 12 |
| 45 | Nucleotide sequence encoding the variable region of the heavy chain | 13 |
| | Amino acid sequence encoding the variable region of the heavy chain | 14 |
| | Nucleotide sequence encoding the variable region of the light chain | 15 |
| | Amino acid sequence encoding the variable region of the light chain | 16 |
| 026 | Nucleotide sequence encoding the variable region of the heavy chain | 17 |
| | Amino acid sequence encoding the variable region of the heavy chain | 18 |
| | Nucleotide sequence encoding the variable region of the light chain | 19 |
| | Amino acid sequence encoding the variable region of the light chain | 20 |
| 140 | Nucleotide sequence encoding the variable region of the heavy chain | 21 |
| | Amino acid sequence encoding the variable region of the heavy chain | 22 |
| | Nucleotide sequence encoding the variable region of the light chain | 23 |
| | Amino acid sequence encoding the variable region of the light chain | 24 |
| 11 | Nucleotide sequence encoding the variable region of the heavy chain | 25 |
| | Amino acid sequence encoding the variable region of the heavy chain | 26 |
| | Nucleotide sequence encoding the variable region of the light chain | 27 |
| | Amino acid sequence encoding the variable region of the light chain | 28 |
| 86 | Nucleotide sequence encoding the variable region of the heavy chain | 29 |
| | Amino acid sequence encoding the variable region of the heavy chain | 30 |
| | Nucleotide sequence encoding the variable region of the light chain | 31 |
| | Amino acid sequence encoding the variable region of the light chain | 32 |
| 124 | Nucleotide sequence encoding the variable region of the heavy chain | 33 |
| | Amino acid sequence encoding the variable region of the heavy chain | 34 |
| | Nucleotide sequence encoding the variable region of the light chain | 35 |
| | Amino acid sequence encoding the variable region of the light chain | 36 |
| 275 | Nucleotide sequence encoding the variable region of the heavy chain | 37 |
| | Amino acid sequence encoding the variable region of the heavy chain | 38 |
| | Nucleotide sequence encoding the variable region of the light chain | 39 |
| | Amino acid sequence encoding the variable region of the light chain | 40 |

TABLE 1-continued

| mAb ID No.: | Sequence | SEQ ID NO: |
|---|---|---|
| 96 | Nucleotide sequence encoding the variable region of the heavy chain | 41 |
| | Amino acid sequence encoding the variable region of the heavy chain | 42 |
| | Nucleotide sequence encoding the variable region of the light chain | 43 |
| | Amino acid sequence encoding the variable region of the light chain | 44 |
| 238 | Nucleotide sequence encoding the variable region of the heavy chain | 45 |
| | Amino acid sequence encoding the variable region of the heavy chain | 46 |
| | Nucleotide sequence encoding the variable region of the light chain | 47 |
| | Amino acid sequence encoding the variable region of the light chain | 48 |
| 214 | Nucleotide sequence encoding the variable region of the heavy chain | 49 |
| | Amino acid sequence encoding the variable region of the heavy chain | 50 |
| | Nucleotide sequence encoding the variable region of the light chain | 51 |
| | Amino acid sequence encoding the variable region of the light chain | 52 |
| 225 | Nucleotide sequence encoding the variable region of the heavy chain | 53 |
| | Amino acid sequence encoding the variable region of the heavy chain | 54 |
| | Nucleotide sequence encoding the variable region of the light chain | 55 |
| | Amino acid sequence encoding the variable region of the light chain | 56 |
| 195 | Nucleotide sequence encoding the variable region of the heavy chain | 57 |
| | Amino acid sequence encoding the variable region of the heavy chain | 58 |
| | Nucleotide sequence encoding the variable region of the light chain | 59 |
| | Amino acid sequence encoding the variable region of the light chain | 60 |
| 168 | Nucleotide sequence encoding the variable region of the heavy chain | 61 |
| | Amino acid sequence encoding the variable region of the heavy chain | 62 |
| | Nucleotide sequence encoding the variable region of the light chain | 63 |
| | Amino acid sequence encoding the variable region of the light chain | 64 |
| 163 | Nucleotide sequence encoding the variable region of the heavy chain | 65 |
| | Amino acid sequence encoding the variable region of the heavy chain | 66 |
| | Nucleotide sequence encoding the variable region of the light chain | 67 |
| | Amino acid sequence encoding the variable region of the light chain | 68 |
| 113 | Nucleotide sequence encoding the variable region of the heavy chain | 69 |
| | Amino acid sequence encoding the variable region of the heavy chain | 70 |
| | Nucleotide sequence encoding the variable region of the light chain | 71 |
| | Amino acid sequence encoding the variable region of the light chain | 72 |
| 302 | Nucleotide sequence encoding the variable region of the heavy chain | 73 |
| | Amino acid sequence encoding the variable region of the heavy chain | 74 |
| | Nucleotide sequence encoding the variable region of the light chain | 75 |
| | Amino acid sequence encoding the variable region of the light chain | 76 |
| 168g2/ 183k | Nucleotide sequence encoding the variable region of the heavy chain | 77 |
| | Amino acid sequence encoding the variable region of the heavy chain | 78 |
| | Nucleotide sequence encoding the variable region of the light chain | 79 |
| | Amino acid sequence encoding the variable region of the light chain | 80 |

Definitions

Unless otherwise defined, scientific and technical terms used in connection with the invention described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See, e.g., Sambrook et al., *Molecular Cloning: A Laboratory Manual* (2d ed., Cold Spring Harbor Laboratory Press, Cold Spring Harbor, N.Y. 1989), which is incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g. free of murine proteins, (3) is expressed by a cell from a different species, or (4) does not occur in nature.

The term "polypeptide" is used herein as a generic term to refer to native protein, fragments, or analogs of a polypeptide sequence. Hence, native protein, fragments, and analogs are species of the polypeptide genus. Preferred polypeptides in accordance with the invention comprise the human heavy chain immunoglobulin molecules and the human kappa light chain immunoglobulin molecules, as well as antibody molecules formed by combinations comprising the heavy chain immunoglobulin molecules with light chain immunoglobulin molecules, such as the kappa light chain immunoglobulin molecules, and vice versa, as well as fragments and analogs thereof.

The term "naturally occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

The term "polynucleotide" as referred to herein means a polymeric form of nucleotides of at least 10 bases in length, either ribonucleotides or deoxynucleotides or a modified form of either type of nucleotide. The term includes single and double stranded forms of DNA.

The term "oligonucleotide" referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g. for probes; although oligonucleotides may be double stranded, e.g. for use in the construction of a gene mutant. Oligonucleotides of the invention can be either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phoshoraniladate, phosphoroamidate, and the like. See e.g., LaPlanche et al. *Nucl. Acids Res.* 14:9081 (1986); Stec et al. *J. Am. Chem. Soc.* 106:6077 (1984); Stein et al. *Nucl. Acids Res.* 16:3209 (1988); Zon et al. *Anti-Cancer Drug Design* 6:539 (1991); Zon et al. *Oligonucleotides and Analogues: A Practical Approach*, pp. 87-108 (F. Eckstein, Ed., Oxford University Press, Oxford England (1991)); Stec et al. U.S. Pat. No. 5,151,510; Uhlmann and Peyman *Chemical Reviews* 90:543 (1990), the disclosures of which are hereby incorporated by reference. An oligonucleotide can include a label for detection, if desired.

The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest will be at least 80%, and more typically with preferably increasing homologies of at least 85%, 90%, 95%, 99%, and 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See M. O. Dayhoff, in *Atlas of Protein Sequence and Structure*, Vol. 5, 101-110 and Supplement 2 to Vol. 5, 1-10 (National Biomedical Research Foundation 1972). The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a "GTATA".

The following terms are used to describe the sequence relationships between two or more polynucleotide or amino acid sequences: "reference sequence," "comparison window," "sequence identity," "percentage of sequence identity," and "substantial identity". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window," as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman, *Adv. Appl. Math.* 2:482 (1981), by the homology alignment algorithm of Needleman and Wunsch, *J. Mol. Biol.* 48:443 (1970), by the search for similarity method of Pearson and Lipman, *Proc. Natl. Acad. Sci.* (*U.S.A.*) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See *Immunology—A Synthesis* (2d ed., Golub, E. S. and Gren, D. R. eds., Sinauer Associates, Sunderland, Mass. 1991), which is incorporated herein by reference. Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the invention described herein. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity. Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

As discussed herein, minor variations in the amino acid sequences of antibodies or immunoglobulin molecules are contemplated as being encompassed by the invention described herein, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains.

Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al., *Science* 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally occurring peptide sequence. For example, single or multiple amino acid substitutions (preferably conservative amino acid substitutions) may be made in the naturally occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, ed., W. H. Freeman and Company, New York 1984); *Introduction to Protein Structure* (Branden, C. and Tooze, J. eds., Garland Publishing, New York, N.Y. 1991); and Thornton et al., *Nature* 354:105 (1991), which are each incorporated herein by reference.

The term "polypeptide fragment" as used herein refers to a polypeptide that has an amino-terminal and/or carboxy-terminal deletion, but where the remaining amino acid sequence is identical to the corresponding positions in the naturally occurring sequence deduced, for example, from a full-length cDNA sequence. Fragments typically are at least 5, 6, 8 or 10 amino acids long, preferably at least 14 amino acids long, more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has at least one of the following properties: (1) specific binding to a PTH, under suitable binding conditions, (2) ability to block appropriate PTH binding, or (3) ability to inhibit PTH expressing cell growth in vitro or in vivo. Typically, polypeptide analogs comprise a conservative amino acid substitution (or addition or deletion) with respect to the naturally occurring sequence. Analogs typically are at least 20 amino acids long, preferably at least 50 amino acids long or longer, and can often be as long as a full-length naturally occurring polypeptide.

Peptide analogs are commonly used in the pharmaceutical industry as non-peptide drugs with properties analogous to those of the template peptide. These types of non-peptide compound are termed "peptide mimetics" or "peptidomimetics." Fauchere, *J. Adv. Drug Res.* 15:29 (1986); Veber and Freidinger, *TINS* p.392 (1985); and Evans et al., *J. Med. Chem.* 30:1229 (1987), which are incorporated herein by reference. Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —$CH_2NH$—, —$CH_2S$—, —$CH_2$—$CH_2$—, —CH=CH-(cis and trans), —$COCH_2$—, —CH(OH)$CH_2$—, and —$CH_2SO$—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch *Ann. Rev. Biochem.* 61:387 (1992), incorporated herein by reference); for example, by adding internal cysteine residues capable of forming intramolecular disulfide bridges which cyclize the peptide.

"Antibody" or "antibody peptide(s)" refer to an intact antibody, or a binding fragment thereof that competes with the intact antibody for specific binding. Binding fragments are produced by recombinant DNA techniques, or by enzymatic or chemical cleavage of intact antibodies. Binding fragments include Fab, Fab', F(ab')$_2$, Fv, and single-chain antibodies. An antibody other than a "bispecific" or "bifunctional" antibody is understood to have each of its binding sites identical. An antibody substantially inhibits adhesion of a receptor to a counterreceptor when an excess of antibody reduces the quantity of receptor bound to counterreceptor by at least about 20%, 40%, 60% or 80%, and more usually greater than about 85% (as measured in an in vitro competitive binding assay).

The term "epitope" includes any protein determinant capable of specific binding to an immunoglobulin or T-cell receptor. Epitopic determinants usually consist of chemically active surface groupings of molecules such as amino acids or sugar side chains and usually have specific three-dimensional structural characteristics, as well as specific charge characteristics. An antibody is said to specifically bind an antigen when the dissociation constant is $\leq 1$ μM, preferably $\leq 100$ nM and most preferably $\leq 10$ nM.

The term "agent" is used herein to denote a chemical compound, a mixture of chemical compounds, a biological macromolecule, or an extract made from biological materials.

"Active" or "activity" for the purposes herein refers to form(s) of PTH polypeptide which retain a biological and/or an immunological activity of native or naturally occurring PTH polypeptides, wherein "biological" activity refers to a biological function (either inhibitory or stimulatory) caused by a native or naturally occurring PTH polypeptide other than the ability to induce the production of an antibody against an antigenic epitope possessed by a native or naturally occurring PTH polypeptide and an "immunological" activity refers to the ability to induce the production of an antibody against an antigenic epitope possessed by a native or naturally occurring PTH polypeptide.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Mammal" refers to any animal classified as a mammal, including humans, other primates, such as monkeys, chimpanzees and gorillas, domestic and farm animals, and zoo, sports, laboratory, or pet animals, such as dogs, cats, cattle, horses, sheep, pigs, goats, rabbits, rodents, etc. For purposes of treatment, the mammal is preferably human.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an "F(ab')$_2$" fragment that has two antigen-combining sites and is still capable of cross-linking antigen.

"Fv" is the minimum antibody fragment that contains a complete antigen-recognition and binding site of the antibody. This region consists of a dimer of one heavy- and one light-chain variable domain in tight, non-covalent association. It is in this configuration that the three CDRs of each variable domain interact to define an antigen-binding site on the surface of the VH-VL dimer. Collectively, the six CDRs confer antigen-binding specificity to the antibody. However, for example, even a single variable domain (e.g., the VH or VL portion of the Fv dimer or half of an Fv comprising only three CDRs specific for an antigen) may have the ability to recognize and bind antigen, although, possibly, at a lower affinity than the entire binding site.

A Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. F(ab')$_2$ antibody fragments originally were produced as pairs of Fab' fragments which have hinge cysteines between them. Other chemical couplings of antibody fragments are also known.

"Solid phase" means a non-aqueous matrix to which the antibodies described herein can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phases can comprise the well of an assay plate; in others it is a purification column (e.g., an affinity chromatography column). This term also includes a discontinuous solid phase of discrete particles, such as those described in U.S. Pat. No. 4,275,149.

The term "liposome" is used herein to denote a small vesicle composed of various types of lipids, phospholipids and/or surfactant which is useful for delivery of a drug (such as a PTH polypeptide or antibody thereto) to a mammal. The components of the liposomes are commonly arranged in a bilayer formation, similar to the lipid arrangement of biological membranes.

The term "small molecule" is used herein to describe a molecule with a molecular weight below about 500 Daltons.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

The term "pharmaceutical agent or drug" as used herein refers to a chemical compound or composition capable of inducing a desired therapeutic effect when properly administered to a patient. Other chemistry terms herein are used according to conventional usage in the art, as exemplified by *The McGraw-Hill Dictionary of Chemical Terms* (Parker, S., Ed., McGraw-Hill, San Francisco (1985)), incorporated herein by reference).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term "patient" includes human and veterinary subjects.

Antibody Structure

The basic antibody structural unit is known to comprise a tetramer. Each tetramer is composed of two identical pairs of polypeptide chains, each pair having one "light" (about 25 kDa) and one "heavy" chain (about 50 to 70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989)) (incorporated by reference in its entirety for all purposes). The variable regions of each light/heavy chain pair form the antibody-binding site. Thus, an intact antibody has two binding sites. Except in bifunctional or bispecific antibodies, the two binding sites are the same.

The chains all exhibit the same general structure of relatively conserved framework regions (FR) joined by three hyper variable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, *Sequences of Proteins of Immunological Interest* (National Institutes of Health, Bethesda, Md. 1991) (1987), or Chothia and Lesk, *J. Mol Biol.* 196:901-17 (1987); Chothia et al., *Nature* 342:878-83 (1989).

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai and Lachmann, *Clin. Exp. Immunol.* 79: 315-21 (1990); Kostelny et al., *J. Immunol.* 148:1547-53 (1992). Production of bispecific antibodies can be a relatively labor intensive process compared with production of conventional antibodies and yields and degree of purity are generally lower for bispecific antibodies. Bispecific antibodies do not exist in the form of fragments having a single binding site (e.g., Fab, Fab', and Fv).

Human Antibodies and Humanization of Antibodies

Human antibodies avoid certain of the problems associated with antibodies that possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, fully human antibodies can be generated through the introduction of human antibody function into a rodent so that the rodent produces fully human antibodies.

Human Antibodies

One method for generating fully human antibodies is through the use of XenoMouse® strains of mice that have been engineered to contain human heavy chain and light chain genes within their genome. For example, a XenoMouse® mouse containing 245 kb and 190 kb-sized germline configuration fragments of the human heavy chain locus and kappa light chain locus is described in Green et al., *Nature Genetics* 7:13-21 (1994). The work of Green et al. was extended to the introduction of greater than approximately 80% of the human antibody repertoire through utilization of megabase-sized, germline configuration YAC fragments of the human heavy chain loci and kappa light chain loci, respectively. See Mendez et al., *Nature Genetics* 15:146-56 (1997) and U.S. patent application Ser. No. 08/759,620, filed Dec. 3, 1996, the disclosures of which are hereby incorporated by reference. Further, XenoMouse® mice have been generated that contain the entire lambda light chain locus (U.S. patent application Ser. No. 60/334,508, filed Nov. 30, 2001). And, XenoMouse® mice have been generated that produce multiple isotypes (see, e.g., WO 00/76310). XenoMouse® strains are available from Abgenix, Inc. (Fremont, Calif.).

The production of XenoMouse® mice is further discussed and delineated in U.S. patent application Ser. No. 07/466,008, filed Jan. 12, 1990, Ser. No. 07/610,515, filed Nov. 8, 1990, Ser. No. 07/919,297, filed Jul. 24, 1992, Ser. No. 07/922,649, filed Jul. 30, 1992, filed Ser. No. 08/031,801, filed Mar. 15, 1993, Ser. No. 08/112,848, filed Aug. 27, 1993, Ser. No. 08/234,145, filed Apr. 28, 1994, Ser. No. 08/376,279, filed Jan. 20, 1995, Ser. No. 08/430,938, Apr. 27, 1995, Ser. No. 08/464,584, filed Jun. 5, 1995, Ser. No. 08/464,582, filed Jun. 5, 1995, Ser. No. 08/463,191, filed Jun. 5, 1995, Ser. No. 08/462,837, filed Jun. 5, 1995, Ser. No. 08/486,853, filed Jun. 5, 1995, Ser. No. 08/486,857, filed Jun. 5, 1995, Ser. No. 08/486,859, filed Jun. 5, 1995, Ser. No. 08/462,513, filed Jun. 5, 1995, Ser. 08/724,752, filed Oct. 2, 1996, and Ser. No. 08/759,620, filed Dec. 3, 1996 and U.S. Pat. Nos. 6,162,963, 6,150,584, 6,114,598, 6,075,181, and 5,939,598 and Japanese Patent Nos. 3 068 180 B2, 3 068 506 B2, and 3 068 507 B2. See also Mendez et al. *Nature Genetics* 15:146-156 (1997) and Green and Jakobovits *J. Exp. Med.,* 188:483-495 (1998). See also European Patent No., EP 463,151 B1, grant published Jun. 12, 1996, International Patent Application No., WO 94/02602, published Feb. 3, 1994, International Patent Application No., WO 96/34096, published Oct. 31, 1996, WO 98/24893, published Jun. 11, 1998, WO 00/76310, published Dec. 21, 2000. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661,016, 5,770,429, 5,789,650, 5,814,318, 5,877,397, 5,874,299, and 6,255,458 each to Lonberg and Kay, U.S. Pat. No. 5,591,669 and 6,023.010 to Krimpenfort and Berns, U.S. Pat. Nos. 5,612,205, 5,721,367, and 5,789,215 to Berns et al., and U.S. Pat. No. 5,643,763 to Choi and Dunn, and GenPharm International U.S. patent application Ser. No. 07/574,748, filed Aug. 29, 1990, Ser. No. 07/575,962, filed Aug. 31, 1990, Ser. No. 07/810,279, filed Dec. 17, 1991, Ser. No. 07/853,408, filed Mar. 18, 1992, Ser. No. 07/904,068, filed Jun. 23, 1992, Ser. No. 07/990,860, filed Dec. 16, 1992, Ser. No. 08/053,131, filed Apr. 26, 1993, Ser. No. 08/096,762, filed Jul. 22, 1993, Ser. No. 08/155,301, filed Nov. 18, 1993, Ser. No. 08/161,739, filed Dec. 3, 1993, Ser. No. 08/165,699, filed Dec. 10, 1993, Ser. No. 08/209,741, filed Mar. 9, 1994, the disclosures of which are hereby incorporated by reference. See also European Patent No. 546,073 B1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175, the disclosures of which are hereby incorporated by reference in their entirety. See further Taylor et al., (1992), Chen et al., (1993), Tuaillon et al., (1993), Choi et al., (1993), Lonberg et al., (1994), Taylor et al., (1994), and Tuaillon et al., (1995), Fishwild et al., (1996), the disclosures of which are hereby incorporated by reference in their entirety.

Kirin has demonstrated the generation of human antibodies from mice in which, through microcell fusion, large pieces of chromosomes, or entire chromosomes, have been introduced. See European Patent Application Nos. 773,288 and 843,961, the disclosures of which are hereby incorporated by reference.

Lidak Pharmaceuticals (now Xenorex) has also demonstrated the generation of human antibodies in SCID mice modified by injection of non-malignant mature peripheral leukocytes from a human donor. The modified mice exhibit an immune response characteristic of the human donor upon stimulation with an immunogen, which consists of the production of human antibodies. See U.S. Pat. Nos. 5,476,996 and 5,698,767, the disclosures of which are herein incorporated by reference.

Human anti-mouse antibody (HAMA) responses have led the industry to prepare chimeric or otherwise humanized antibodies. While chimeric antibodies have a human constant region and a murine variable region, it is expected that certain human anti-chimeric antibody (HACA) responses will be observed, particularly in chronic or multi-dose utilizations of the antibody. Thus, it would be desirable to provide fully human antibodies against PTH in order to vitiate concerns and/or effects of HAMA or HACA response.

Humanization and Display Technologies

As discussed above in connection with human antibody generation, there are advantages to producing antibodies with reduced immunogenicity. To a degree, this can be accomplished in connection with techniques of humanization and display techniques using appropriate libraries. It will be appreciated that murine antibodies or antibodies from other species can be humanized or primatized using techniques well known in the art. See e.g., Winter and Harris, *Immunol Today* 14:43-46 (1993) and Wright et al., *Crit, Reviews in Immunol.* 12:125-168 (1992). The antibody of interest may be engineered by recombinant DNA techniques to substitute the CH1, CH2, CH3, hinge domains, and/or the framework domain with the corresponding human sequence (see WO 92/02190 and U.S. Pat. Nos. 5,530,101, 5,585,089, 5,693,761, 5,693,792, 5,714,350, and 5,777,085). Also, the use of Ig cDNA for construction of chimeric immunoglobulin genes is known in the art (Liu et al., *P.N.A.S.* 84:3439 (1987) and *J. Immunol.* 139:3521 (1987)). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al., "Sequences of Proteins of Immunological Interest," N.I.H. publication no. 91-3242 (1991). Human C region genes are readily available from known clones. The choice of isotype will be guided by the desired effector functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

Antibody fragments, such as Fv, F(ab').sub.2 and Fab may be prepared by cleavage of the intact protein, e.g., by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g., SV-40 early promoter, (Okayama et al., *Mol. Cell. Bio.* 3:280 (1983)), Rous sarcoma virus LTR (Gorman et al., *P.N.A.S.* 79:6777 (1982)), and moloney murine leukemia virus LTR (Grosschedl et al., *Cell* 41:885 (1985)). Also, as will be appreciated, native Ig promoters and the like may be used.

Further, human antibodies or antibodies from other species can be generated through display-type technologies, including, without limitation, phage display, retroviral display, ribosomal display, and other techniques, using techniques well known in the art and the resulting molecules can be subjected to additional maturation, such as affinity maturation, as such techniques are well known in the art. Wright and Harris, supra., Hanes and Plucthau, *PNAS USA* 94:4937-4942 (1997) (ribosomal display), Parmley and Smith, *Gene*

73:305-318 (1988) (phage display), Scott, *TIBS* 17:241-245 (1992), Cwirla et al., *PNAS USA* 87:6378-6382 (1990), Russel et al., *Nucl. Acids Res.* 21:1081-1085 (1993), Hoganboom et al., *Immunol. Reviews* 130:43-68 (1992), Chiswell and McCafferty, *TIBTECH* 10:80-84 (1992), and U.S. Pat. No. 5,733,743. If display technologies are utilized to produce antibodies that are not human, such antibodies can be humanized as described above.

Using these techniques, antibodies can be generated against PTH expressing cells, PTH itself, forms of PTH, epitopes or peptides thereof, and expression libraries thereto (see e.g. U.S. Pat. No. 5,703,057) which can thereafter be screened as described above for the activities described above.

Preparation of Antibodies

Antibodies in accordance with the invention were prepared through the utilization of the XenoMouse® technology, as described below. Such mice, then, are capable of producing human immunoglobulin molecules and antibodies and are deficient in the production of murine immunoglobulin molecules and antibodies. Technologies utilized for achieving the same are disclosed in the patents, applications, and references disclosed in the previous section, herein. In particular, however, a preferred embodiment of transgenic production of mice and antibodies therefrom is disclosed in U.S. patent application Ser. No. 08/759,620, filed Dec. 3, 1996 and International Patent Application Nos. WO 98/24893, published Jun. 11, 1998 and WO 00/76310, published Dec. 21, 2000, the disclosures of which are hereby incorporated by reference. See also Mendez et al., *Nature Genetics* 15:146-156 (1997), the disclosure of which is hereby incorporated by reference.

Antibodies, as described herein, are neutralizing high affinity antibodies to human PTH. Further, in some embodiments, the antibodies cross react with rat PTH. Several different methods have been used historically to generate monoclonal antibodies or polyclonal antibodies against the N-terminus of human PTH. These approaches have included immunizing with full length human PTH (hPTH) or bovine PTH (bPTH) (Vieira et al., *Braz. J. Med. Biol. Res.* 21:1005-1011 (1988)), synthetic peptides of human PTH (1-34 or 1-37) (Visser et al., *Acta Endocrinol.* 90:90-102 (1979); Logue et al., *J. Immunol. Methods* 137:159-66 (1991)), and multiple antigenic peptides (MAP) of hPTH (1-10), hPTH (9-18) and hPTH (24-37) (Magerlein et al., *Drug Res.* 48:783-87 (1998)). These approaches did not produce antibodies suitable for human therapeutics. (See section entitled "Therapeutic Administration and Formulation" herein for therapeutic criteria.) High affinity antibodies to hPTH are difficult to make because of B cell tolerance to the peptide. However, Bradwell et al., (1999) have demonstrated that immunization with a mixture of human PTH (1-34) and bovine PTH (1-34) MAPs followed by a mixture of human and bovine MAPs targeting the hPTH(51-84) and bPTH(51-86) was effective in breaking B-cell tolerance to PTH in a human patient with an inoperable parathyroid tumor.

The approach described herein was designed to overcome B-cell tolerance to hPTH as well as to produce a fully human monoclonal antibody suitable for therapeutic and diagnostic use. XenoMouse® animals were immunized with synthetic peptides of PTH (hPTH(1-34) and rPTH(1-34)), because synthetic peptides have been successfully used to generate antibodies specific to endogenous human PTH (Visser et al., (1979)). Furthermore, because the N-terminus of murine PTH is highly conserved with human PTH (85% identity) and rat PTH (91%), the combination of peptides was used as an immunogen to break B-cell tolerance to murine PTH through molecular mimicry, thereby allowing the generation of high affinity human anti-human PTH antibodies. These peptides were both coupled to keyhole limpet hemocyanin and emulsified in complete Freund's adjuvant or incomplete Freund's adjuvant to enhance the immunogenicity of these proteins.

After immunization, lymphatic cells (such as B cells) were recovered from the mice that expressed antibodies, and such recovered cell lines fused with a myeloid-type cell line to prepare immortal hybridoma cell lines. Such hybridoma cell lines were screened and selected to identify hybridoma cell lines that produced antibodies specific to the antigen of interest. Herein, the production of multiple hybridoma cell lines that produce antibodies specific to PTH is described. Further, a characterization of the antibodies produced by such cell lines is provided, including nucleotide and amino acid sequence analyses of the heavy and light chains of such antibodies.

Alternatively, instead of being fused to myeloma cells to generate hybridomas, B cells may be directly assayed. For example, the CD19+B cells may be isolated from hyperimmune XenoMouse® mice and allowed to proliferate and differentiate into antibody-secreting plasma cells. Antibodies from the cell supernatants are then screened by ELISA for reactivity against the PTH immunogen. The supernatants are also screened for immunoreactivity against fragments of PTH to further epitope map the different antibodies and with rat PTH to determine species cross-reactivity. Single plasma cells secreting antibodies with the desired specificities are then isolated using a PTH-specific hemolytic plaque assay (Babcook et al., *Proc. Natl. Acad. Sci. USA* 93:7843-48 (1996)). Cells targeted for lysis are preferably sheep red blood cells (SRBCs) coated with the PTH antigen. In the presence of a B cell culture containing plasma cells secreting the immunoglobulin of interest and complement, the formation of a plaque indicates specific PTH-mediated lysis of the sheep red blood cells surrounding the plasma cell of interest. The single antigen-specific plasma cell in the center of the plaque can be isolated and the genetic information that encodes the specificity of the antibody can be isolated from the single plasma cell. As an alternative to B-cell culture, antigen-specific plasma cells can be isolated directly from CD138+ splenocytes or lymphocytes of hyperimmune animals. Independent of the method of isolation, the DNA encoding the heavy and light chain variable regions of the antibody can be cloned after performing reverse-transcriptase PCR. Such cloned DNA can then be further inserted into a suitable expression vector, preferably a vector cassette such as a pcDNA, more preferably such a pcDNA vector containing the constant domains of immunglobulin heavy and light chain. The generated vector can then be transfected into host cells, preferably CHO cells, and cultured in conventional nutrient media modified as appropriate for inducing promoters, selecting transformants, or amplifying the genes encoding the desired sequences. The isolation of multiple single plasma cells that produce antibodies specific to PTH is described below. Further, the genetic material that encodes the specificity of the anti-PTH antibody can be isolated, introduced into a suitable expression vector that can then be transfected into host cells.

In general, antibodies produced by the above-mentioned cell lines possessed fully human IgG2 heavy chains with human kappa light chains. The antibodies possessed high affinities, typically possessing a dissociation constant ($K_D$) of from about $10^{-6}$ through about $10^{-12}$ M, when measured by either solid phase and solution phase. Antibodies possessing a $K_D$ from at least $10^{-9}$ M are preferred, with antibodies possessing $K_D$'s of $10^{-10}$, $10^{-11}$, or $10^{-12}$ M being highly preferred. Due to the kinetics of monoclonal antibody interactions with secreted antigens, the efficiency of binding is greatly reduced when the antibody $K_D$ exceeds the concentration of the antigen. To efficiently suppress levels of the antigen, the antibody $K_D$ should be less than the antigen concentration.

Regarding the importance of affinity to therapeutic utility of anti-PTH antibodies, it will be understood that one can generate anti-PTH antibodies, for example, combinatorially, and assess such antibodies for binding affinity. One approach that can be utilized is to take the heavy chain cDNA from an antibody, prepared as described above and found to have good affinity to PTH, and combine it with the light chain cDNA from a second antibody, prepared as described above and also found to have good affinity to PTH, to produce a third antibody. The affinities of the resulting third antibodies can be measured as described herein and those with desirable dissociation constants isolated and characterized. For example, based on the high binding affinity of anti-PTH mAb 183 and anti-PTH mAb 168 antibodies, heavy chain cDNA from anti-PTH mAb 168 can be linked to the light chain cDNA from anti-PTH mAb 183 and the resulting antibody can be assayed for binding. Alternatively, the light chain of any of the antibodies described above can be used as a tool to aid in the generation of a heavy chain that when paired with the light chain will exhibit a high affinity for PTH, or vice versa. For example, the light chain or the light chain variable region of anti-PTH mAb 183 can be expressed with a library of heavy chains or heavy chain variable regions. These heavy chain variable regions in this library could be isolated from naive animals, isolated from hyperimmune animals, generated artificially from libraries containing variable heavy chain sequences that differ in the CDR regions, or generated by any other methods that produce diversity within the CDR regions of any heavy chain variable region gene (such as random or directed mutagenesis). These CDR regions, and in particular CDR3, may be a significantly different length or sequence identity from the heavy chain initially paired with anti-PTH mAb 183. The resulting library could then be screened for high affinity binding to PTH to generate a therapeutically relevant antibody molecule with similar properties as anti-PTH mAb 183 (high affinity and neutralization). A similar process using the heavy chain or the heavy chain variable region can be used to generate a therapeutically relevant antibody molecule with a unique light chain variable region. Furthermore, the novel heavy chain variable region, or light chain variable region, can then be used in a similar fashion as described above to identify a novel light chain variable region, or heavy chain variable region, that allows the generation of a novel antibody molecule.

Another combinatorial approach that can be utilized is to perform mutagenesis on germ line heavy and/or light chains that are demonstrated to be utilized in the antibodies in accordance with the invention described herein, particularly in the complementarity determining regions (CDRs). The affinities of the resulting antibodies can be measured as described herein and those with desirable dissociation constants isolated and characterized. Upon selection of a preferred binder, the sequence or sequences encoding the same may be used to generate recombinant antibodies as described above. Appropriate methods of performing mutagenesis on an oligonucleotide are known to those skilled in the art and include chemical mutagenesis, for example, with sodium bisulfite, enzymatic misincorporation, and exposure to radiation. It is understood that the invention described herein encompasses antibodies with substantial identity, as defined herein, to the antibodies explicitly set forth herein, whether produced by mutagenesis or by any other means. Further, antibodies with conservative or non-conservative amino acid substitutions, as defined herein, made in the antibodies explicitly set forth herein, are included in embodiments of the invention described herein.

Another combinatorial approach that can be used is to express the CDR regions, and in particular CDR3, of the antibodies described above in the context of framework regions derived from other variable region genes. For example, CDR1 (GYSFTSYWIG (SEQ ID NO: 89)), CDR2 (IISPGDSDTRYSPSFQG (SEQ ID NO: 90)) and CDR3 (QGDYVWGSYDS (SEQ ID NO: 91)) of the heavy chain of anti-PTH mAb 183 could be expressed in the context of the framework regions of other heavy chain variable genes. Similarly, CDR1 (KSSQSLLDSDGKTYLY (SEQ ID NO: 92)), CDR2 (EVSNRFS (SEQ ID NO: 93)) and CDR3 (MPSIHLWT (SEQ ID NO: 94)) of the light chain of anti-PTH mAb 183 could be expressed in the context of the framework regions of other light chain variable genes. In addition, the germline sequences of these CDR regions could be expressed in the context of other heavy or light chain variable region genes (for example, heavy chain CDR2: IIYPGDSDTRYSPSFQG (SEQ ID NO: 95)). The resulting antibodies can be assayed for specificity and affinity and may allow the generation of a novel antibody molecule.

Furthermore, a heavy chain CDR3 with the ability to interact with PTH from the germline D-region 21-10 cam be created. One reading frame of the germline form of this D-region encodes the core binding region of CDR3 (YY DYVWGSYAYT (SEQ ID NO: 96)) as underlined. The underlined core sequence, or fragments thereof, with random flanking amino acids could be expressed to generate a novel CDR3 with similar specificity to the CDR3 identified in anti-PTH mAb 183. The new heavy chain could generate an antibody with similar or improved binding properties compared to the original anti-PTH mAb 183. One may also mutate this D-region encoding CDR3 to generate a functionally equivalent antibody to anti-PTH mAb 183. For example, the aspartic acid ("D") of the sequence (DYVWGSY (SEQ ID NO: 97)) can be mutated to any other amino acid and when paired with a relevant light chain the new antibody can be assayed for specificity and high affinity. Similarly, amino acids encoded in the CDR3 of the light chain can be added and/or removed by slightly altering the junction of the V region and the J region as well as altering the number and identity of the nucleotides used to join these two light chain segments.

In the preferred embodiment, the properties of anti-PTH mAb 183 include, for example, high affinity of the antibody for PTH ($K_D$ of $10^{-10}$ or better), specificity for a neutralizing epitope on the N-terminus of human PTH or orthologous proteins, the ability to neutralize calcium flux in PTH-responsive cells, and the ability to inhibit hypercalcemia in rats infused with human PTH. The examples are illustrative of the many possible means under the current art to use the sequences of the invention to aid in the generation of an antibody with similar properties to anti-PTH mAb 183. Any improvements to the current art or any generation of unique antibodies through future or conventional technology with the aforementioned properties ascribed to anti-PTH mAb 183 are deemed to be "functionally equivalent" to anti-PTH mAb 183 and thereby are included in embodiments of the invention described herein.

As will be appreciated, antibodies in accordance with the invention described herein can be expressed in various cell lines. Sequences encoding particular antibodies can be used for transformation of a suitable mammalian host cell. Transformation can be accomplished by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference). The transformation procedure used depends upon the host to be transformed. Methods for introduction of heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. Cell lines of particular preference are selected through determining which cell lines have high expression levels and produce antibodies with constitutive PTH binding properties.

Epitope Mapping

Immunoblot Analysis

The binding of the antibodies described herein to PTH can be examined by a number of methods. For example, PTH may be subjected to SDS-PAGE and analyzed by immunoblotting. The SDS-PAGE may be performed either in the absence or presence of a reduction agent. Such chemical modifications may result in the methylation of cysteine residues. Accordingly, it is possible to determine whether the anti-PTH antibodies described herein bind to a linear epitope on PTH.

Surface-Enhanced Laser Desorption/Ionization

Epitope mapping of the epitope for the PTH antibodies described herein can also be performed using SELDI. SELDI ProteinChip® arrays are used to define sites of protein-protein interaction. Antigens are specifically captured on antibodies covalently immobilized onto the Protein Chip array surface by an initial incubation and wash. The bound antigens can be detected by a laser-induced desorption process and analyzed directly to determine their mass. Such fragments of the antigen that bind are designated as the "epitope" of a protein.

The SELDI process enables individual components within complex molecular compositions to be detected directly and mapped quantitatively relative to other components in a rapid, highly-sensitive and scalable manner. SELDI utilizes a diverse array of surface chemistries to capture and present large numbers of individual protein molecules for detection by a laser-induced desorption process. The success of the SELDI process is defined in part by the miniaturization and integration of multiple functions, each dependent on different technologies, on a surface ("chip"). SELDI BioChips and other types of SELDI probes are surfaces "enhanced" such that they become active participants in the capture, purification (separation), presentation, detection, and characterization of individual target molecules (e.g., proteins) or population of molecules to be evaluated.

A single SELDI protein BioChip, loaded with only the original sample, can be read thousands of times. The SELDI protein BioChips from LumiCyte hold as many as 10,000 addressable protein docking locations per 1 square centimeter. Each location may reveal the presence of dozens of individual proteins. When the protein composition information from each location is compared and unique information sets combined, the resulting composition map reveals an image with sets of features that are used collectively to define specific patterns or molecular "fingerprints." Different fingerprints may be associated with various stages of health, the onset of disease, or the regression of disease associated with the administration of appropriate therapeutics.

The SELDI process may be described in further detail in four parts. Initially, one or more proteins of interest are captured or "docked" on the ProteinChip Array, directly from the original source material, without sample preparation and without sample labeling. In a second step, the "signal-to-noise" ratio is enhanced by reducing the chemical and biomolecular "noise." Such "noise" is reduced through selective retention of target on the chip by washing away undesired materials. Further, one or more of the target protein(s) that are captured are read by a rapid, sensitive, laser-induced process (SELDI) that provides direct information about the target (molecular weight). Lastly, the target protein at any one or more locations within the array may be characterized in situ by performing one or more on-the-chip binding or modification reactions to characterize protein structure and function.

Phage Display

The epitope for the anti-PTH antibodies described herein can be determined by exposing the ProteinChip Array to a combinatorial library of random peptide 12-mer displayed on Filamentous phage (New England Biolabs).

Phage display describes a selection technique in which a peptide is expressed as a fusion with a coat protein of a bacteriophage, resulting in display of the fused protein on the surface of the virion. Panning is carried out by incubation of a library of phage displayed peptide with a plate or tube coated with the target, washing away the unbound phage, and eluting the specifically bound phage. The eluted phage is then amplified and taken through additional binding and amplification cycles to enrich the pool in favor of binding sequences. After three or four rounds, individual clones binding are further tested for binding by phage ELISA assays performed on antibody-coated wells and characterized by specific DNA sequencing of positive clones.

After multiple rounds of such panning against the anti-PTH antibodies described herein, the bound phage may be eluted and subjected to further studies for the identification and characterization of the bound peptide.

Diagnostic Use

Antibodies in accordance with the invention described herein are useful for diagnostic assays, and, particularly, in vitro assays, for example, for use in determining the level of circulating PTH in the bloodstream. It is possible to determine the presence and/or severity of hyperparathyroidism in a subject based on expression levels of the PTH antigen. Patient samples, preferably blood, and more preferably blood serum, are taken from subjects diagnosed as being at various stages in the progression of hyperparathyroidism, and/or at various points in the therapeutic treatment of the disease. The concentration of the PTH antigen present in the blood samples is determined using a method that specifically determines the amount of the antigen that is present. Such a method includes an ELISA method in which, for example, antibodies of the invention may be conveniently immobilized on an insoluble matrix, such as a polymer matrix. Using a population of samples that provides statistically significant results for known levels of progression or therapy, a range of concentrations of the antigen that may be considered characteristic of each level is designated.

In order to determine the degree of hyperparathyroidism in a subject under study, or to characterize the response of the subject to a course of therapy, a sample of blood is taken from the subject and the concentration of the PTH antigen present in the sample is determined. The concentration so obtained is used to identify in which range of concentrations the value falls. The range so identified correlates with a level of disease progression or a level of therapy identified in the various populations of diagnosed subjects, thereby providing a level in the subject under study.

Gene amplification and/or expression may be measured in a sample directly, for example, by conventional Southern blotting, Northern blotting to quantitate the transcription of mRNA (Thomas, *Proc. Natl. Acad. Sci. USA,* 77:5201-5205 (1980)), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay can be carried out where the duplex is bound to a surface, so that upon the formation of duplex on the surface, the presence of antibody bound to the duplex can be detected.

For example, antibodies, including antibody fragments, can be used to qualitatively or quantitatively detect the expression of PTH proteins. As noted above, the antibody preferably is equipped with a detectable, e.g., fluorescent label, and binding can be monitored by light microscopy, flow cytometry, fluorimetry, or other techniques known in the art. These techniques are particularly suitable if the amplified gene encodes a cell surface protein, e.g., a growth factor. Such binding assays are performed as known in the art.

In situ detection of antibody binding to the PTH protein can be performed, for example, by immunofluorescence or immunoelectron microscopy. For this purpose, a tissue specimen is removed from the patient, and a labeled antibody is applied to it, preferably by overlaying the antibody on a biological sample. This procedure also allows for determining the distribution of the marker gene product in the tissue examined. It will be apparent for those skilled in the art that a wide variety of histological methods are readily available for in situ detection.

One of the most sensitive and most flexible quantitative methods for quantitating differential gene expression is RT-PCR, which can be used to compare mRNA levels in different sample populations, in normal and tumor tissues, with or without drug treatment, to characterize patterns of gene expression, to discriminate between closely related mRNAs, and to analyze RNA structure.

The first step is the isolation of mRNA from a target sample. The starting material is typically total RNA isolated from a disease tissue and corresponding normal tissues, respectively. Thus, mRNA can be extracted, for example, from frozen or archived paraffin-embedded and fixed (e.g. formalin-fixed) samples of diseased tissue for comparison with normal tissue of the same type. Methods for mRNA extraction are well known in the art and are disclosed in standard textbooks of molecular biology, including Ausubel et al., *Current Protocols of Molecular Biology,* John Wiley and Sons (1997). Methods for RNA extraction from paraffin embedded tissues are disclosed, for example, in Rupp and Locker, *Lab Invest.,* 56:A67 (1987), and De Andrés et al., *BioTechniques,* 18:42044 (1995). In particular, RNA isolation can be performed using purification kit, buffer set and protease from commercial manufacturers, such as QIAGEN® according to the manufacturer's instructions. For example, total RNA from cells in culture can be isolated using QIAGEN® RNEASY® mini-columns. Total RNA from tissue samples can be isolated using RNA STAT-60® centrifugation (Tel-Test).

As RNA cannot serve as a template for PCR, the first step in differential gene expression analysis by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GENEAMP® RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' endonuclease activity. Thus, TAQMAN® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicontypical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan RT-PCR can be performed using commercially available equipments, such as, for example, ABI PRIZM 7700™ Sequence Detection System™ (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRIZM 7700™ Sequence Detection System™. The system consists of a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5'-Nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle (Ct). The ΔCt values are used as quantitative measurement of the relative number of starting copies of a particular target sequence in a nucleic acid sample when comparing the expression of RNA in a cell from a diseased tissue with that from a normal cell.

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and β-actin.

Differential gene expression can also be identified, or confirmed using the microarray technique. In this method, nucleotide sequences of interest are plated, or arrayed, on a microchip substrate. The arrayed sequences are then hybridized with specific DNA probes from cells or tissues of interest.

In a specific embodiment of the microarray technique, PCR amplified inserts of cDNA clones are applied to a substrate in a dense array. Preferably at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip selectively hybridize to each spot of DNA on the array. After stringent washing to remove non-specifically bound probes, the chip is scanned by confocal laser microscopy. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., *Proc. Natl. Acad. Sci. USA*, 93(20)L106-49). The methodology of hybridization of nucleic acids and microarray technology is well known in the art.

PTH Agonists and Antagonists

Embodiments of the invention described herein also pertain to variants of a PTH protein that function as either PTH agonists (mimetics) or as PTH antagonists. Variants of a PTH protein can be generated by mutagenesis, e.g., discrete point mutation or truncation of the PTH protein. An agonist of the PTH protein can retain substantially the same, or a subset of, the biological activities of the naturally occurring form of the PTH protein. An antagonist of the PTH protein can inhibit one or more of the activities of the naturally occurring form of the PTH protein by, for example, competitively binding to a downstream or upstream member of a cellular signaling cascade which includes the PTH protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the PTH protein.

Variants of the PTH protein that function as either PTH agonists (mimetics) or as PTH antagonists can be identified by screening combinatorial libraries of mutants, e.g., truncation mutants, of the PTH protein for protein agonist or antagonist activity. In one embodiment, a variegated library of PTH variants is generated by combinatorial mutagenesis at the nucleic acid level and is encoded by a variegated gene library. A variegated library of PTH variants can be produced by, for example, enzymatically ligating a mixture of synthetic oligonucleotides into gene sequences such that a degenerate set of potential PTH sequences is expressible as individual polypeptides, or alternatively, as a set of larger fusion proteins (e.g., for phage display) containing the set of PTH sequences therein. There are a variety of methods which can be used to produce libraries of potential PTH variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential PTH variant sequences. Methods for synthesizing degenerate oligonucleotides are known in the art (see, e.g., Narang, *Tetrahedron* 39:3 (1983); Itakura et al., *Annu. Rev. Biochem.* 53:323 (1984); Itakura et al., *Science* 198:1056 (1984); Ike et al., *Nucl. Acid Res.* 11:477 (1983).

Additional Criteria for Antibody Therapeutics

As discussed herein, the function of the PTH antibody appears important to at least a portion of its mode of operation. By function, is meant, by way of example, the activity of the anti-PTH antibody in binding to PTH. Accordingly, in certain respects, it may be desirable in connection with the generation of antibodies as therapeutic candidates against PTH that the antibodies be capable of fixing complement and participating in complement-dependent cytotoxicity (CDC). For example, the anti-PTH antibodies according to embodiments of the invention described herein may be made capable of effector function, including CDC and antibody-dependent cellular cytotoxicity (ADCC). There are a number of isotypes of antibodies that are capable of the same, including, without limitation, the following: murine IgM, murine IgG2a, murine IgG2b, murine IgG3, human IgM, human IgG1, and human IgG3. It will be appreciated that antibodies that are generated need not initially possess such an isotype but, rather, the antibody as generated can possess any isotype and the antibody can be isotype switched thereafter using conventional techniques that are well known in the art. Such techniques include the use of direct recombinant techniques (see, e.g., U.S. Pat. No.

4,816,397 and U.S. Pat. No. 6,331,415), cell-cell fusion techniques (see, e.g., U.S. Pat. Nos. 5,916,771 and 6,207,418), among others.

In the cell-cell fusion technique, a myeloma or other cell line is prepared that possesses a heavy chain with any desired isotype and another myeloma or other cell line is prepared that possesses the light chain. Such cells can, thereafter, be fused and a cell line expressing an intact antibody can be isolated.

By way of example, certain anti-PTH antibodies of the invention described herein are human anti-PTH IgG2 antibodies. If such an antibody possessed desired binding to the PTH molecule, it could be readily isotype switched to generate a human IgM, human IgG1, or human IgG3 isotype, while still possessing the same variable region (which defines the antibody's specificity and some of its affinity).

Accordingly, as antibody candidates are generated that meet desired "structural" attributes as discussed above, they can generally be provided with certain alternate "functional" attributes through isotype switching.

Design and Generation of Other Therapeutics

In accordance with embodiments of the invention described herein and based on the activity of the antibodies that are produced and characterized herein with respect to PTH, the design of other therapeutic modalities beyond antibody moieties is facilitated. Such modalities include, without limitation, advanced antibody therapeutics, such as bispecific antibodies, immunotoxins, and radiolabeled therapeutics, generation of peptide therapeutics, gene therapies, particularly intrabodies, antisense therapeutics, and small molecules.

In connection with the generation of advanced antibody therapeutics, where complement fixation is a desirable attribute, it may be possible to sidestep the dependence on complement for cell killing through the use of bispecifics, immunotoxins, or radiolabels, for example.

For example, in connection with bispecific antibodies, bispecific antibodies can be generated that comprise (i) two antibodies one with a specificity to PTH and another to a second molecule that are conjugated together, (ii) a single antibody that has one chain specific to PTH and a second chain specific to a second molecule, or (iii) a single chain antibody that has specificity to PTH and the other molecule. Such bispecific antibodies can be generated using techniques that are well known for example, in connection with (i) and (ii) see e.g., Fanger et al. *Immunol Methods* 4:72-81 (1994) and Wright and Harris, supra. and in connection with (iii) see e.g., Traunecker et al. *Int. J. Cancer (Suppl.)* 7:51-52 (1992). In each case, the second specificity can be made to the heavy chain activation receptors, including, without limitation, CD16 or CD64 (see e.g., Deo et al. 18:127 (1997)) or CD89 (see e.g., Valerius et al. *Blood* 90:4485-4492 (1997)).

In connection with immunotoxins, antibodies can be modified to act as immunotoxins utilizing techniques that are well known in the art. See e.g., Vitetta *Immunol Today* 14:252 (1993). See also U.S. Pat. No. 5,194,594. In connection with the preparation of radiolabeled antibodies, such modified antibodies can also be readily prepared utilizing techniques that are well known in the art. See e.g., Junghans et al. in *Cancer Chemotherapy and Biotherapy* 655-686 (2d edition, Chafner and Longo, eds., Lippincott Raven (1996)). See also U.S. Pat. Nos. 4,681,581, 4,735,210, 5,101,827, 5,102,990 (RE 35,500), 5,648,471, and 5,697,902.

Therapeutic Administration and Formulations

Biologically active anti-PTH antibodies in accordance with the invention described herein may be used in a sterile pharmaceutical preparation or formulation to reduce the level of serum PTH thereby effectively treating pathological conditions where, for example, serum PTH is abnormally elevated. Such conditions include, for instance, hyperparathyroidism, such as primary, secondary, and tertiary hyperparathyroidism, hypercalcemia, and hyperphosphatemia. The anti-PTH antibody preferably possesses adequate affinity to potently suppress PTH to within the target therapeutic range, and preferably has an adequate duration of action to allow for infrequent dosing. In the treatment of secondary hyperparathyroidism in hemodialysis patients, PTH should preferably be suppressed by the administration of the antibody with a minimum duration of at least two days to provide continuous efficacy between dialysis sessions, which occur three times weekly. Such duration of action allows for intravenous dosing at the time of hemodialysis, which will result in increased compliance and convenience to patients and health care providers. In other hyperparathyroid patient populations, a prolonged duration of action of greater than two days, preferably three to five days, more preferably seven to ten days, will allow for less frequent and more convenient dosing schedules by alternate parenteral routes such as subcutaneous or intramuscular injection.

The preference for high affinity and prolonged duration of action extends to all conditions of hyperparathyroidism, such as primary hyperparathyroidism, secondary hyperparathyroidism and tertiary hyperparathyroidism. A convenient prolonged duration of action is one that preferably exceeds two days, preferably one that exceeds five to seven days, more preferably one that exceeds ten days, following a single dose of the antibody. A preferred antibody of the invention has a $K_D$ of $10^{-10}$ M, a half-life exceeding 1.5 days, preferably 2 to 4 days, more preferably 6 to 10 days and suppresses the levels of circulating PTH by greater than 50%, preferably by greater than 60%, 65%, or 70%, more preferably by greater than 75%, 80% or 85%. In a preferred embodiment, an antibody demonstrating a suppression of greater than 75% for greater than 1.5 days is provided.

Biologically active anti-PTH antibodies of the instant invention may be employed alone or in combination with other therapeutic agents. For example, current approved therapy for secondary hyperparathyroidism due to chronic renal failure (CRF) consists of (1) calcitriol (active form of vitamin D) and analogs, which act to promote absorption of calcium in the gastrointestinal tract, (2) calcium carbonate with meals to bind to phosphate and prevent its absorption in the gut, and (3) other phosphate binders. One of the main causes of secondary hyperparathyroidism in CRF is high levels of serum phosphate acting directly on the parathyroid glands causing them to produce PTH. Phosphate levels increase due to inadequate phosphate excretion due to the kidney failure. The above-mentioned current treatments act to prevent bone resorption and could be used in combination with antibodies of the invention described herein in a therapeutic regime.

When used for in vivo administration, the antibody formulation should be sterile. This is readily accomplished, for example, by filtration through sterile filtration membranes, prior to or following lyophilization and reconstitution. The antibody ordinarily will be stored in lyophilized form or in solution. Therapeutic antibody compositions generally are placed into a container having a sterile access port, for example, an intravenous solution bag or vial having an adapter that allows retrieval of the formulation, such as a stopper pierceable by a hypodermic injection needle.

The route of antibody administration is in accord with known methods, e.g., injection or infusion by intravenous, intraperitoneal, intracerebral, intramuscular, intraocular, intraarterial, intrathecal, inhalation or intralesional routes, or by sustained release systems as noted below. The antibody is preferably administered continuously by infusion or by bolus injection.

An effective amount of antibody to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. Typically, the clinician will administer antibody until a dosage is reached that achieves the desired effect. The progress of this therapy is easily monitored by conventional assays or by the assays described herein.

Antibodies in accordance with the invention may be prepared in a mixture with a pharmaceutically acceptable carrier. This therapeutic composition can be administered intravenously or through the nose or lung, preferably as a liquid or powder aerosol (lyophilized). The composition may also be administered parenterally or subcutaneously as desired. When administered systemically, the therapeutic composition should be sterile, pyrogen-free and in a parenterally acceptable solution having due regard for pH, isotonicity, and stability. These conditions are known to those skilled in the art.

Briefly, dosage formulations of the compounds of the invention described herein are prepared for storage or administration by mixing the compound having the desired degree of purity with physiologically acceptable carriers, excipients, or stabilizers. Such materials are non-toxic to the recipients at the dosages and concentrations employed, and include buffers such as TRIS HCl, phosphate, citrate, acetate and other organic acid salts; antioxidants such as ascorbic acid; low molecular weight (less than about ten residues) peptides such as polyarginine, proteins, such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium and/or nonionic surfactants such as TWEEN, PLURONICS or polyethyleneglycol.

Sterile compositions for injection can be formulated according to conventional pharmaceutical practice as described in *Remington's Pharmaceutical Sciences* (18th ed., Mack Publishing Company, Easton, Pa. 1990). For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice.

Suitable examples of sustained-release preparations include semipermeable matrices of solid hydrophobic polymers containing the polypeptide, which matrices are in the form of shaped articles, films or microcapsules. Examples of sustained-release matrices include polyesters, hydrogels (e.g., poly(2-hydroxyethyl-methacrylate) as described by Langer et al., *J. Biomed Mater. Res.*, 15:167-277 (1981) and Langer, *Chem. Tech.*, 12:98-105 (1982), or poly(vinylalcohol)), polylactides (U.S. Pat. No. 3,773,919, EP 58,481), copolymers of L-glutamic acid and gamma ethyl-L-glutamate (Sidman et al., *Biopolymers*, 22:547-56 (1983)), non-degradable ethylene-vinyl acetate (Langer et al., supra), degradable lactic acid-glycolic acid copolymers such as the LUPRON Depot™ (injectable microspheres composed of lactic acid-glycolic acid copolymer and leuprolide acetate), and poly-D-(-)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through disulfide interchange, stabilization may be achieved by modifying sulfhydryl residues, lyophilizing from acidic solutions, controlling moisture content, using appropriate additives, and developing specific polymer matrix compositions.

Sustained-release compositions also include liposomally entrapped antibodies of the invention. Liposomes containing such antibodies are prepared by methods known per se: U.S. Pat. No. DE 3,218,121; Epstein et al., *Proc. Natl. Acad. Sci. USA*, 82:3688-92 (1985); Hwang et al., *Proc. Natl. Acad. Sci. USA*, 77:4030-34 (1980); EP 52,322; EP 36,676; EP 88,046; EP 143,949; 142,641; Japanese patent application 83-118008; U.S. Pat. Nos. 4,485,045 and 4,544,545; and EP 102,324.

The dosage of the antibody formulation for a given patient will be determined by the attending physician taking into consideration various factors known to modify the action of drugs including severity and type of disease, body weight, sex, diet, time and route of administration, other medications and other relevant clinical factors. Therapeutically effective dosages may be determined by either in vitro or in vivo methods.

An effective amount of the antibody of the invention to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 0.001 mg/kg to up to 100 mg/kg or more, depending on the factors mentioned above. Desirable dosage concentrations include 0.001 mg/kg, 0.005 mg/kg, 0.01 mg/kg, 0.05 mg/kg, 0.1 mg/kg, 0.5 mg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, and 100 mg/kg or more. Typically, the clinician will administer the therapeutic antibody until a dosage is reached that achieves the desired effect. The progress of this therapy is easily monitored by conventional assays or as described herein.

EXAMPLES

The following examples, including the experiments conducted and results achieved are provided for illustrative purposes only and are not to be construed as limiting upon the invention described herein.

Example 1

PTH Antigen Preparation

The following PTH peptides were used in the experiments described herein.

```
Human PTH (1-84):
SVSEIQLMHNLGKHLNSMERVEWLRKKIQDVHNF  (SEQ ID NO: 81)
VALGAPLAPRDAGSQRPRKKEDNVLVESHEKSLG
EADKADVNVLTKAKSQ Human PTH (1-34):
SVSEIQLMHNLGKHLNSMERVEWLRKKLQDVHNF  (SEQ ID NO: 82)
```

-continued

Human PTH (7-84):
LMHNLGKHLNSMERVEWLRKKLQDVHNFVALGAP (SEQ ID NO: 83)
LAPRDAGSQRPRKKEDNVLVESHEKSLGEADKAD
VNVLTKAKSQ Human PTH (18-48):
MERVEWLRKKLQDVHNFVALGAPLAPRDAGS (SEQ ID NO: 84)

Human PTH-related peptide (1-34):
AVSEHQLLHDKGKSIQDLRRRFFLHHLIAEIHTA (SEQ ID NO: 85)

Rat PTH (1-84):
AVSEIQLMHNLGKHLASVERMQWLRKKLQDVHNF (SEQ ID NO: 86)
VSLGVQMAAREGSYQRPTKKEENVLVDGNSKSLG
EGDKADVDVLVKAKSQ

Rat PTH (1-34):
AVSEIQLMHNLGKHLASVERMQWLRKKLQDVHNF (SEQ ID NO: 87)

Cynomolgus PTH (1-84):
SVSEIQLMHNLGKHLNSMERVEWLRKKLQDVHNF (SEQ ID NO: 88)
IALGAPLAPRDAGSQRPRKKEDNILVESHEKSLG
EADKADVDVLTKAKSQ.

These peptides were purchased from Bachem California Inc., Torrance, Calif. Cynomolgus PTH (1-84) was also purchased from CS Bio Company, Inc., San Carlos, Calif.

Antigen Preparation. The antigen used for the immunization of XenoMouse® animals was prepared as follows. Human PTH1-34 (500 mcg) was mixed with rat PTH1-34 (500 mcg) and dissolved in 500 mcL of conjugation buffer (0.1M MES, 0.9M NaCl, pH 4.7). Two milligrams of keyhole limpet hemocyanin (KLH; Pierce, Rockford, Ill.) were dissolved in 200 mcL of distilled water and then added to the PTH mixture. PTH and KLH were cross-linked by the addition of 50 mcL of a 10 mg/mL stock solution of 1-ethyl-3-[3-dimethylaminopropyl]carbodiimide hydrochloride (EDC, Pierce, Rockford, Ill.) and incubation of the mixture for 2 hours at room temperature. The unreacted EDC was removed by overnight dialysis through a 1 kDa cutoff membrane against PBS pH 7.4.

Example 2

Anti-PTH Antibodies

Antibody Generation

Immunization of animals. Monoclonal antibody against PTH was developed by sequentially immunizing XenoMouse® mice (XenoMouse® XG2, Abgenix, Inc. Fremont, Calif.). Synthetic 34mer human and rat PTH (50/50) coupled to KLH as described above was used as the antigen. The initial immunization was with 10 µg of antigen mixed 1:1 v/v with Complete Freund's Adjuvant (CFA, Sigma, Oakville, ON) per mouse. Subsequent boosts were made first with 10 µg of antigen admixed 1:1 v/v with Incomplete Freund's Adjuvant (IFA, Sigma, Oakville, ON) per mouse, followed by three injections with 10 µg of antigen mixed 1:1 v/v with IFA, and then a final boost of 10 µg of antigen admixed 1:1 v/v with IFA per mouse. In particular, each mouse was immunized at the base of the tail by subcutaneous injection. The animals were immunized on days 0, 14, 28, 42 and 54. The animals were bled on day 49 to obtain sera for harvest selection as described below.

Selection of animals for harvest. Anti-PTH antibody titers were determined by ELISA. PTH (84mer; 1 µg/mL) was coated onto Costar Labcoat Universal Binding Polystyrene 96-well plates (Corning, Acton, Mass.) overnight at four degrees. The solution containing unbound PTH was removed and the plates were treated with UV light (365 nm) for 4 minutes (4000 microjoules). The plates were washed five times with dH$_2$O. XenoMouse® sera from the PTH immunized animals, or naïve XenoMouse® animals, were titrated in 2% milk/PBS at 1:2 dilutions in duplicate from a 1:100 initial dilution. The last well was left blank. The plates were washed five times with dH$_2$O. A goat anti-human IgG Fc-specific horseradish peroxidase (HRP, Pierce, Rockford, Ill.) conjugated antibody was added at a final concentration of 1 µg/mL for 1 hour at room temperature. The plates were washed five times with dH$_2$O. The plates were developed with the addition of TMB chromogenic substrate (Gaithersburg, Md.) for 30 minutes and the ELISA was stopped by the addition of 1 M phosphoric acid. The specific titer of individual XenoMouse® animals was determined from the optical density at 450 nm and are shown in Table 2. The titer represents the reciprocal dilution of the serum and therefore the higher the number the greater the humoral immune response to PTH.

TABLE 2

| Mouse I.D. | Titer |
|---|---|
| M469-1 | 16000 |
| M469-2 | 4000 |
| M469-3 | 16000 |
| M469-4 | 32000 |
| M469-5 | 8000 |
| M469-6 | 32000 |
| M469-7 | 8000 |
| M469-8 | 32000 |
| M469-9 | >32000 |
| M469-10 | 3200 |
| Naïve | 1000 |

XenoMouse® animals (M469-4, M469-6, M469-8 and M469-9) were selected for harvest based on the serology data in Table 2.

Culture and selection of B cells. B cells from the harvested animals were cultured and those secreting PTH-specific antibodies were isolated as described in Babcook et al., *Proc. Natl. Acad. Sci. USA,* 93:7843-48 (1996). ELISA, performed as described above, was used to identify primary PTH-specific wells. One hundred plates cultured at 500, 250, 125 or 50 cells/well were screened on PTH to identify the antigen-specific wells and 98 wells showed ODs significantly over background (0.1), a representative sample of which are shown in Table 3.

TABLE 3

| | Positives above cutoff OD of: | | | | | | | | | | | |
|---|---|---|---|---|---|---|---|---|---|---|---|---|
| Tissue | 0.1 | 0.2 | 0.3 | 0.4 | 0.5 | 0.6 | 0.7 | 0.8 | 0.9 | 1.0 | 1.5 | 2.0 |
| Pooled LN @ 500 cells/well (plates #279-303) | 861 | 133 | 52 | 30 | 23 | 16 | 11 | 9 | 8 | 6 | 1 | 1 |

TABLE 3-continued

| Tissue | Positives above cutoff OD of: | | | | | | | | | | | |
|---|---|---|---|---|---|---|---|---|---|---|---|---|
| | 0.1 | 0.2 | 0.3 | 0.4 | 0.5 | 0.6 | 0.7 | 0.8 | 0.9 | 1.0 | 1.5 | 2.0 |
| Pooled LN @ 250 cells/well (plates #304-328) | 436 | 90 | 34 | 23 | 17 | 13 | 8 | 7 | 6 | 5 | 1 | 0 |
| Pooled LN @ 125 cells/well (plates #329-353) | 32 | 8 | 7 | 3 | 3 | 1 | 1 | 1 | 1 | 1 | 0 | 0 |
| Pooled LN @ 50 cells/well (plates #354-378) | 31 | 7 | 5 | 5 | 2 | 2 | 1 | 1 | 1 | 0 | 0 | 0 |
| Total Number Positives: | 1360 | 238 | 98 | 61 | 45 | 32 | 21 | 18 | 16 | 12 | 2 | 1 |

These data indicated a very low frequency of hits and indicated that the wells were monoclonal for antigen-specificity at all cell dilutions. These 98 positive wells were rescreened on antigen (Table 4) and only 48 wells were found to repeat as clearly antigen-specific wells. These 48 wells were analyzed for binding to either hPTH7-84 or hPTH18-48. Antibodies specific to hPTH7-34 were desired as they were unlikely to cross-react with human PTHrp. A total of 14 wells with reactivity for either hPTH7-84 or hPTH18-48 were identified and these wells were subsequently analyzed for relative affinity using into limiting antigen ELISA analysis as described below. The well 292A10 was the source of anti-PTH mAb 183. This well bound nicely to human PTH 1-84 (OD 1.4), human PTH 7-84 (OD 1.95), human PTH 18-48 (OD 3.26) and rat PTH 1-84 (OD 0.66). These data were qualitative and were useful to indicate that this antibody binds PTH between amino acids 18 and 34 (as the immunogen was only the N-terminal fragment 1-34) and that this antibody was able to bind to rat PTH.

Limiting antigen analysis. The limiting antigen analysis is a method that affinity ranks the antigen-specific antibodies in the B cell culture supernatants relative to all other antigen-specific antibodies. The concept being that in the presence of a very low coating of antigen that only the highest affinity antibodies will be able to bind to any detectable level at equilibrium. (See, e.g., U.S. Ser. No. 60/337,250, filed Dec. 3, 2001.) Biotinylated PTH was bound to streptavidin plates at 25 ng/mL for 30 minutes at room temperature on 96-well culture plates. Each plate was washed 5 times with dH$_2$O, before 40 µL of 1% milk in PBS with 0.05% sodium azide were added to the plate, followed by 10 µL of B cell supernatant added to each well. After 18 hours at room temperature on a shaker, the plates were again washed 5 times with dH$_2$O. To each well was added 50 µL of Gt anti-Human (Fc)-HRP at 1 µg/mL. After 1 hour at room temperature, the plates were again washed 5 times with dH$_2$O and 50 µL of TMB substrate were added to each well. The reaction was stopped by the addition of 50 µL of 1M phosphoric acid to each well and the plates were read at wavelength 450 nm to give the results shown in Table 4.

Quantitation of antigen-specific antibody in the B-cell culture supernatants have indicated the concentration ranges from 10 ng/mL to 500 ng/mL. As it is difficult to determine the concentration of antigen-specific antibody in every antigen-specific well, the results generated from limiting antigen analysis was compared to a titration of recombinant antibodies at comparable concentrations (2 ng/mL to 100 ng/mL). In this assay less than half of the antibodies were able to give detectable binding and well 292A10 (anti-PTH mAb 183) was clearly superior as measured by O.D. to the other culture supernatants and recombinant antibodies at all concentrations (Table 4).

TABLE 4

| Plate ID | Limited Ag OD | 1' OD | Hu 84mer | 7-84mer | 18-48mer | Rat 84mer |
|---|---|---|---|---|---|---|
| 292A10 (XG2-183) | 2.747 | 0.992 | 1.40 | 1.95 | 3.26 | 0.62 |
| 302A7 (XG2-168) | 1.376 | 0.317 | 0.35 | 0.36 | 2.66 | 0.19 |
| 361B2 | 0.747 | 0.416 | 0.48 | 0.37 | 0.26 | 0.49 |
| 331H6 | 0.322 | 0.312 | 0.52 | 0.45 | 2.40 | 0.24 |
| 287E7 | 0.261 | 0.682 | 0.71 | 0.13 | 0.36 | 1.03 |
| 315D8 | 0.221 | 0.441 | 0.14 | 0.17 | 0.29 | 0.31 |
| 279E6 | 0.213 | 0.379 | 0.31 | 0.10 | 0.17 | 0.19 |
| 313D5 | 0.170 | 0.664 | 0.12 | 0.29 | 0.43 | 0.30 |
| 339F5 | 0.120 | 0.319 | 0.40 | 0.21 | 0.11 | 0.25 |
| 279D2 | 0.114 | 0.353 | 0.31 | 0.11 | 0.27 | 0.18 |
| 307H1 | 0.084 | 0.401 | 0.10 | 0.14 | 0.30 | 0.42 |
| 308A1 | 0.079 | 0.312 | 0.19 | 0.22 | 0.30 | 0.45 |
| 284D9 (XG2-262) | ND | 0.585 | 1.46 | 0.07 | 0.25 | 2.11 |
| 322F2 | ND | 1.87 | 1.01 | 0.15 | 0.34 | 1.41 |

PTH-specific Hemolytic Plaque Assay. A number of specialized reagents were needed to conduct the assay. These reagents were prepared as follows.

Biotinylation of Sheep red blood cells (SRBC). SRBC were stored in RPMI media as a 25% stock. A 250 µL SRBC packed-cell pellet was obtained by aliquoting 1.0 mL of the stock into a 15-mL falcon tube, spinning down the cells and removing the supernatant. The cell pellet was then re-suspended in 4.75 mL PBS at pH 8.6 in a 50 mL tube. In a separate 50 mL tube, 2.5 mg of Sulfo-NHS biotin was added to 45 mL of PBS at pH 8.6. Once the biotin had completely dissolved, 5 mL of SRBCs were added and the tube rotated at RT for 1 hour. The SRBCs were centrifuged at 3000 g for 5 min, the supernatant drawn off and 25 mL PBS at pH 7.4 as a wash. The wash cycle was repeated 3 times, then 4.75 mL immune cell media (RPMI 1640 with 10% FCS) was added to the 250 µL biotinylated-SRBC (B-SRBC) pellet to gently re-suspend the B-SRBC (5% B-SRBC stock). Stock was stored at 4° C. until needed.

Streptavidin (SA) coating of B-SRBC. One mL of the 5% B-SRBC stock was transferred into to a fresh eppendorf tube. The B-SRBC cells were pelleted with a pulse spin at 8000 rpm (6800 rcf) in microfuge, the supernatant drawn off, the pellet re-suspended in 1.0 mL PBS at pH 7.4, and the centrifugation repeated. The wash cycle was repeated 2 times, then the B-SRBC pellet was resuspended in 1.0 mL of PBS at pH 7.4 to give a final concentration of 5% (v/v). 10 µL of a 10 mg/mL streptavidin (CalBiochem, San Diego, Calif.) stock solution was added and the tube mixed and rotated at RT for 20 min. The washing steps were repeated and the SA-SRBC were re-suspended in 1 mL PBS pH 7.4 (5% (v/v)).

Human PTH 1-34 coating of SA-SRBC. The SA-SRBC were coated with biotinylated-Human PTH 1-34 at 10 μg/mL, the mixed and rotated at RT for 20 min. The SRBC were washed twice with 1.0 mL of PBS at pH 7.4 as above. The PTH-coated SRBC were re-suspended in RPMI (+10% FCS) to a final concentration of 5% (v/v).

Determination of the quality of PTH-SRBC by immunofluorescence (IF). 10 μL of 5% SA-SRBC and 10 μL of 5% PTH-coated SRBC were each added to separate fresh 1.5 mL eppendorf tube containing 40 μL of PBS. A control human anti-PTH antibody was added to each sample of SRBCs at 45 μg/mL. The tubes were rotated at RT for 25 min, and the cells were then washed three times with 100 μL of PBS. The cells were re-suspended in 50 μL of PBS and incubated with 2 mcg/mL Gt-anti Human IgG Fc antibody conjugated to Alexa488 (Molecular Probes, Eugene, Oreg.). The tubes were rotated at RT for 25 min, and then washed with 100 μL PBS and the cells re-suspended in 10 μL PBS. 10 μL of the stained cells were spotted onto a clean glass microscope slide, covered with a glass coverslip, observed under fluorescent light, and scored on an arbitrary scale of 0-4.

Preparation of plasma cells. The contents of a single microculture well previously identified by various assays as containing a B cell clone secreting the immunoglobulin of interest were harvested. Using a 100-1000 μL pipettman, the contents of the well were recovered by adding 37 C RPMI (+10% FCS). The cells were re-suspended by pipetting and then transferred to a fresh 1.5 mL eppendorf tube (final volume approximately 500-700 μL). The cells were centrifuged in a microfuge at 1500 rpm (240 rcf) for 2 minutes at room temperature, then the tube rotated 180 degrees and spun again for 2 minutes at 1500 rpm. The freeze media was drawn off and the immune cells resuspended in 100 μL RPMI (10% FCS), then centrifuged. This washing with RPMI (10% FCS) was repeated and the cells re-suspended in 60 μL RPMI (FCS) and stored on ice until ready to use.

Plaque assay. Glass slides (2×3 inch) were prepared in advance with silicone edges and allowed to cure overnight at RT. Before use the slides were treated with approx. 5 μL of SigmaCoat (Sigma, Oakville, ON) wiped evenly over glass surface, allowed to dry and then wiped vigorously. To a 60 μL sample of cells was added 60 μL each of PTH-coated SRBC (5% v/v stock), 4× guina pig complement (Sigma, Oakville, ON) stock prepared in RPMI (FCS), and 4× enhancing sera stock (1:900 in RPMI (FCS)). The mixture (3-5 ul) was spotted onto the prepared slides and the spots covered with undiluted paraffin oil. The slides were incubated at 37° C. for a minimum of 45 minutes.

Plaque assay results. The coating of the sheep red blood cells with Human PTH 1-34 worked very well. The coating was determined qualitatively by immunofluorescent microscopy to be very high (4/4) using a control human anti-PTH antibody to detect coating compared to a secondary detection reagent alone (0/4). There was no signal detected using a control human anti-PTH antibody on red blood cells that were only coated with streptavidin (0/4). These red blood cells were then used to identify antigen-specific plasma cells from the well 292A10 (see Table 5). After micromanipulation to rescue the antigen-specific plasma cells, the genes encoding the variable region genes were rescued by RT-PCR on a single plasma cell.

TABLE 5

| Plate ID | Single Cell Numbers |
| --- | --- |
| 292A10 | PTH-SCX-179-190 |
| 302A7 | PTH-SCX-164-178 |

Expression, Purification and Characterization of Anti-PTH mAb 183

Expression. After isolation of the single plasma cells, mRNA was extracted and reverse transcriptase PCR was conducted to generate cDNA. The cDNA encoding the variable heavy and light chains was specifically amplified using polymerase chain reaction. The variable heavy chain region was cloned into an IgG2 expression vector. This vector was generated by cloning the constant domain of human IgG2 into the multiple cloning site of pcDNA3.1+/Hygro (Invitrogen, Burlington, ON). The variable light chain region was cloned into an IgK expression vector. This vector was generated by cloning the constant domain of human IgK into the multiple cloning site of pcDNA3.1+/Neo (Invitrogen, Burlington, ON). The heavy chain and the light chain expression vectors were then co-lipofected into a 60 mm dish of 70% confluent human embryonal kidney 293 cells and the transfected cells were allowed to secrete a recombinant antibody with the identical specificity as the original plasma cell for 24 hours. The supernatant (3 mL) was harvested from the HEK 293 cells and the secretion of an intact antibody (anti-PTH mAb 183) was demonstrated with a sandwich ELISA to specifically detect human IgG (Table 7). The specificity of anti-PTH mAb 183 was assessed through binding of the recombinant antibody to PTH using ELISA (Table 6). The ability of this antibody to bind to Rat PTH was also demonstrated using an ELISA method (Table 7) as measured by O.D.

TABLE 6

| Clone | Cell # | Secretion | Binding |
| --- | --- | --- | --- |
| 292A10 | SC-PTH-XG2-183 | >1:64 | 1:16 |

TABLE 7

| Conc. | Anti-PTH mAb 183 | |
| --- | --- | --- |
| Neat | 3.291 | 3.432 |
| 1/2 | 3.266 | 3.384 |
| 1/4 | 3.397 | 3.456 |
| 1/8 | 3.123 | 3.272 |
| 1/16 | 2.722 | 3.006 |
| 1/32 | 2.569 | 2.691 |
| 1/64 | 1.893 | 2.362 |
| Blank | 0.215 | 0.182 |

The secretion ELISA tests were performed as follows. Control plates were coated with 2 mg/mL Goat anti-human IgG H+L O/N as for binding plates. Human or rat PTH (84mer; 11 μg/mL) was coated onto Costar Labcoat Universal Binding Polystyrene 96 well plates and held overnight at four degrees. The plates were washed five times with dH$_2$O. Recombinant antibodies were titrated 1:2 for 7 wells from the undiluted minilipofection supernatant. The plates were washed five times with dH$_2$O. A goat anti-human IgG Fc-specific HRP-conjugated antibody was added at a final concentration of 1 µg/mL for 1 hour at RT for the secretion and the two binding assays. The plates were washed five times with dH₂O. The plates were developed with the addition of TMB for 30 minutes and the ELISA was stopped by the addition of 1 M phosphoric acid. Each ELISA plate was analyzed to determine the optical density of each well at 450 nm.

Purification of anti-PTH mAb 183. For larger scale production of anti-PTH mAb 183, the heavy and light chain expression vectors (2.5 µg of each chain/dish) were lipofected into ten 100 mm dishes that were 70% confluent with HEK 293 cells. The transfected cells were incubated at 37° C. for 4 days, the supernatant (6 mL) was harvested and replaced with 6 mL of fresh media. At day 7, the supernatant was removed and pooled with the initial harvest (120 mL total from 10 plates). The anti-PTH mAb 183 antibody was purified from the supernatant using a Protein-A Sepharose (Amersham Biosciences, Piscataway, N.J.) affinity chromatography (1 mL). The antibody was eluted from the Protein-A column with 500 mcL of 0.1 M Glycine pH 2.5. The eluate was dialysed in PBS pH 7.4 and filter sterilized. The antibody was analyzed by non-reducing SDS-PAGE to assess purity and yield.

Deposits of plasmid DNA encoding for the heavy chain and the light chain of anti-PTH mAb 183 have been made, under Budapest Treaty conditions at the American Type Culture Collection, 1080 University Blvd., Manassas, Va. 20110-2209, under ATCC deposit number PTA-4311 for the heavy chain and PTA-4310 for the light chain. The deposit of material does not constitute an admission that the written description herein contained is inadequate to enable the practice of any embodiment of the invention, including the best mode thereof, nor is it to be construed as limiting the scope of the claims to the specific illustrations that it represents. All restrictions on access to the deposits will be removed as required by applicable law and/or regulations.

Failure of anti-PTH mAb 183 to bind to PTH-related peptide (1-34). The ability of anti-PTH mAb 183 to bind to PTH-related protein (PTHrP) was assessed indirectly through its ability to bind to human PTH 1-34 in the presence of saturating levels of PTH-related peptide over a 3-log titration. Biotinylated human PTH 1-34 was bound to streptavidin plates at 1 µg/mL for 30 minutes at RT. The plates were washed 5 times with dH2O. Anti-PTH mAb 183 was then titrated 1:2 from 1 µg/mL in the presence or absence of 5 µg/mL PTH-related protein 1-34. The titrated antibody was then transferred to the plate coated with human PTH 1-34 and allowed to bind for 1 hour at RT. After washing the plates 5 times with dH2O, 50 µL of Gt anti-Human (Fc)-HRP at 1 µg/mL was added to each well and the plates held 1 hour at RT. After washing the plates 5 times with dH2O, 50 µL of TMB substrate was added to each well. To stop the reaction, 50 µL of 1M phosphoric acid was added to each well. The plates were read at wavelength 450 nm. There was no inhibition of anti-PTH mAb 183 binding to human PTH 1-34 even at 1 ng/mL anti-PTH mAb 183 in the presence of 5000 ng/mL PTHrp as shown in Table 8.

TABLE 8

| | Dilution of anti-PTH mAb 183 | | | | | |
|---|---|---|---|---|---|---|
| | 1 µg/mL | 500 ng/mL | 250 ng/mL | 125 ng/mL | 62.5 ng/mL | 31.3 ng/mL |
| +PTHrp (5 µg/mL) | 2.248 | 2.184 | 2.110 | 2.026 | 1.908 | 1.903 |
| | 2.298 | 2.229 | 2.095 | 2.012 | 1.968 | 1.950 |

TABLE 8-continued

| | Dilution of anti-PTH mAb 183 | | | | | |
|---|---|---|---|---|---|---|
| −PTHrp | 2.269 | 2.205 | 2.063 | 2.067 | 1.946 | 1.854 |
| | 2.342 | 2.188 | 2.105 | 2.019 | 1.975 | 1.880 |
| | 15.6 ng/mL | 7.8 ng/mL | 3.9 ng/mL | 2.0 ng/mL | 1 ng/mL | Blank |
| +PTHrp (5 µg/mL) | 1.788 | 1.600 | 1.251 | 0.860 | 0.542 | 0.077 |
| | 1.753 | 1.598 | 1.316 | 0.900 | 0.583 | 0.087 |
| −PTHrp | 1.848 | 1.461 | 1.115 | 0.800 | 0.496 | 0.069 |
| | 1.715 | 1.508 | 1.203 | 0.758 | 0.500 | 0.077 |

Kinetic analysis. The kinetic measurements of the anti-PTH antibody (anti-PTH mAb 183) were evaluated using the KinExA technology. This method involves solution-based determination of formal affinity measurements at equilibrium. Dual curve analysis with two known antibody concentrations and unknown antigen concentration was used to determine the $K_D$ measurements on human 34mer, human 84mer, cynomolgus 84mer and rat 84mer. The $K_D$ was determined to be approximately 10-30 pM for synthetic human PTH (1-84 or 1-34) and cynomolgus PTH (1-84) (CS Bio Company, Inc., San Carlos, Calif.) at room temperature. The $K_D$ of anti-PTH mAb 183 was lower (3000 pM) for synthetic rat PTH 1-84 at room temperature.

The affinity of anti-PTH mAb 183 was also determined for human PTH in pooled serum from hemodialysis patients with end stage renal disease. Binding affinity was determined using an immunoassay-based Scatchard analysis. The binding affinity for endogenous human PTH was 60 pM, consistent with the high affinity observed for synthetic human PTH using KinExA technology.

The affinity ($K_D$) of other PTH-specific monoclonal antibodies was also determined (Table 9). These antibodies were found to be significantly lower affinity (350-5000 pM) than anti-PTH mAb 183 (80 pM) as determined using BiaCore (Amersham Pharmacia) technology. The majority of these recombinant antibodies were also found to map to a similar region or epitope on PTH contained within amino acids (18-34) as anti-PTH mAb 183 (Table 10). This region or epitope has been shown to be involved in receptor binding and, as such, antibodies against this epitope have a strong possibility of displaying neutralizing activity (Duvos et al., Bone, (1995) 17:403-406).

TABLE 9

| Antigen | $K_D$ | $K_D$ High | $K_D$ Low |
|---|---|---|---|
| Human PTH(1-84) | 22 pM | 39 pM | 12 pM |
| Human PTH(1-34) | 33 pM | 65 pM | 14 pM |
| Cynomolgus PTH (1-84) | 10 pM | 18 pM | 5 pM |
| Rat PTH(1-84) | 3 nM | 5 nM | 2 nM |

TABLE 10

| Well ID | Anti-PTH mAb ID | $K_D$ @ 25° C. (nM) - 34mer | $K_D$ @ 37° C. (nM) - 34mer | $K_D$ @ 37° C. (nM) - 84mer | Recombinant Bin |
|---|---|---|---|---|---|
| 133A8 | 011 | 1.0 | 3.5 | ND | 18-34 |
| 126B1 | 026 | 3.0 | 9.5 | ND | 18-34 |
| 123B12 | 045 | 0.5 | 2.0 | ND | 18-34 |
| 119G2 | 057 | 1.0 | 1.0 | ND | 18-34 |
| 133D2 | 086 | 4.7 | 16.7 | ND | 18-34 |
| 135H11 | 124 | 0.5 | 3.3 | ND | 18-34 |

TABLE 10-continued

| Well ID | Anti-PTH mAb ID | $K_D$ @ 25° C. (nM) - 34mer | $K_D$ @ 37° C. (nM) - 34mer | $K_D$ @ 37° C. (nM) - 84mer | Recombinant Bin |
|---|---|---|---|---|---|
| 132G12 | 140 | 0.8 | 5.2 | ND | 18-34 |
| 130A1 | 163 | 3.0 | 7.9 | 41.1 | 18-34 |
| 302A7 | 168 | 2.7 | 2.6 | 9.9 | 18-34 |
| NA | 168g2/183k | 0.28 | 0.64 | ND | ND |
| 292A10 | 183 | 0.08 | 0.1 | 1.0 | 18-34 |
| 267D10 | 214 | 0.8 | 0.4 | 1.6 | 1-7 |
| 275A4 | 225 | 0.35 | 0.6 | 7.1 | 1-7 |
| 264E5 | 238 | 0.6 | 0.2 | 3.9 | 1-7 |
| 284D9 | 262 | ND | ND | ND | 18-34 |
| 252G11 | 275 | ND | ND | ND | 1-7 |
| 130C6 | 302 | ND | ND | ND | 1-34 |

Additional kinetic constants can be calculated from BiaCore data using the methods described in their product literature. A binding speed constant ($k_a$) is the value that represents strength (extent) of binding of an antibody with target antigen as calculated based on antigen-antibody reaction kinetics. A dissociation speed constant ($k_d$) is the value that represents the strength (extent) of dissociation of this monoclonal antibody from target antigen as calculated based on antigen-antibody reaction kinetics. The dissociation constant ($K_D$) is the value obtained by dividing the dissociation speed constant ($k_d$) value from the binding speed constant ($k_a$). These constants were used as indicators that represent affinity of antibodies for antigen and neutralizing activity of antigen. Values for $k_a$ and $k_d$ for the antibodies shown in Table 10 were calculated and are given in Table 11.

TABLE 11

| AB-PTH-XG2-xxx | ka @ 25° C. (nM) - 34mer | kd @ 25° C. (nM) - 34mer | ka @ 37° C. (nM) - 34mer | kd @ 37° C. (nM) - 34mer | ka @ 37° C. (nM) - 84mer | kd @ 37° C. (nM) - 84mer |
|---|---|---|---|---|---|---|
| 011 | $2.3 \times 10^6$ | $2.2 \times 10^{-3}$ | $3.6 \times 10^6$ | $1.3 \times 10^{-2}$ | ND | ND |
| 026 | $1.9 \times 10^6$ | $5.8 \times 10^{-3}$ | $3.1 \times 10^6$ | $2.9 \times 10^{-2}$ | ND | ND |
| 045 | $1.1 \times 10^7$ | $5.5 \times 10^{-3}$ | $1.1 \times 10^7$ | $2.2 \times 10^{-2}$ | ND | ND |
| 057 | $5.6 \times 10^6$ | $5.7 \times 10^{-3}$ | $1.1 \times 10^7$ | $1.1 \times 10^{-2}$ | ND | ND |
| 086 | $2.2 \times 10^6$ | $1.0 \times 10^{-2}$ | $4.3 \times 10^6$ | $7.2 \times 10^{-2}$ | ND | ND |
| 124 | $7.9 \times 10^6$ | $4.3 \times 10^{-3}$ | $7.3 \times 10^6$ | $2.4 \times 10^{-2}$ | ND | ND |
| 140 | $5.9 \times 10^6$ | $4.6 \times 10^{-3}$ | $5.2 \times 10^6$ | $2.7 \times 10^{-2}$ | ND | ND |
| 163 | $1.5 \times 10^6$ | $4.5 \times 10^{-3}$ | $3.4 \times 10^6$ | $2.7 \times 10^{-2}$ | $3.8 \times 10^5$ | $1.6 \times 10^{-2}$ |
| 168 | $9.3 \times 10^5$ | $2.5 \times 10^{-3}$ | $3.1 \times 10^6$ | $8.1 \times 10^{-3}$ | $5.2 \times 10^5$ | $5.2 \times 10^{-3}$ |
| 168g2/183k | $3.0 \times 10^6$ | $8.3 \times 10^{-4}$ | $5.3 \times 10^6$ | $3.4 \times 10^{-3}$ | ND | ND |
| 183 | $4.2 \times 10^6$ | $3.5 \times 10^{-4}$ | $1.5 \times 10^7$ | $1.3 \times 10^{-3}$ | $2.0 \times 10^6$ | $2.0 \times 10^{-3}$ |
| 214 | $1.5 \times 10^5$ | $1.2 \times 10^{-4}$ | $2.6 \times 10^5$ | $1.1 \times 10^{-4}$ | $1.6 \times 10^5$ | $2.5 \times 10^{-4}$ |
| 225 | $2.9 \times 10^5$ | $1.0 \times 10^{-4}$ | $8.9 \times 10^5$ | $5.5 \times 10^{-4}$ | $2.7 \times 10^5$ | $1.9 \times 10^{-3}$ |
| 238 | $1.7 \times 10^5$ | $1.0 \times 10^{-4}$ | $7.6 \times 10^5$ | $1.8 \times 10^{-4}$ | $2.1 \times 10^5$ | $8.2 \times 10^{-4}$ |
| 262 | $7.4 \times 10^6$ | $6.8 \times 10^{-3}$ | $1.7 \times 10^7$ | $4.2 \times 10^{-2}$ | ND | ND |
| 275 | $4.9 \times 10^5$ | $9.8 \times 10^{-5}$ | ND | ND | ND | ND |
| 302 | ND | ND | ND | ND | ND | ND |

Neutralization in vitro of PTH bioactivity with anti-PTH mAb 183. PTH delivers its biological signal to responsive cells through the N-terminal 34 amino acids. Anti-PTH mAb 183 binds to amino acids 18-34 and therefore might be able to inhibit biological activity. As a model system, the rat osteoblastic cell line UMR-106 was used. Human and Rat PTH binds to UMR-106 cells and activates the PTH receptor. Upon activation, the receptor increases the level of intracellular calcium. Intracellular calcium was monitored by the change of fluorescence in cells loaded with a calcium sensitive fluorescent dye, which was measured by FLuorometric Imaging Plate Reader (FLIPR). To determine whether anti-PTH mAb 183 could neutralize PTH effect, the antibody was pre-incubated with PTH and its effect on PTH-induced calcium influx in UMR-106 cells was detected by FLIPR. Anti-PTH mAb 183 blocked the calcium influx induced by 200 nM of human PTH 1-34 in a dose-dependent manner. The IC50 value for anti-PTH mAb 183 was approximately 100 nM as demonstrated in FIG. 1.

Figure 2:
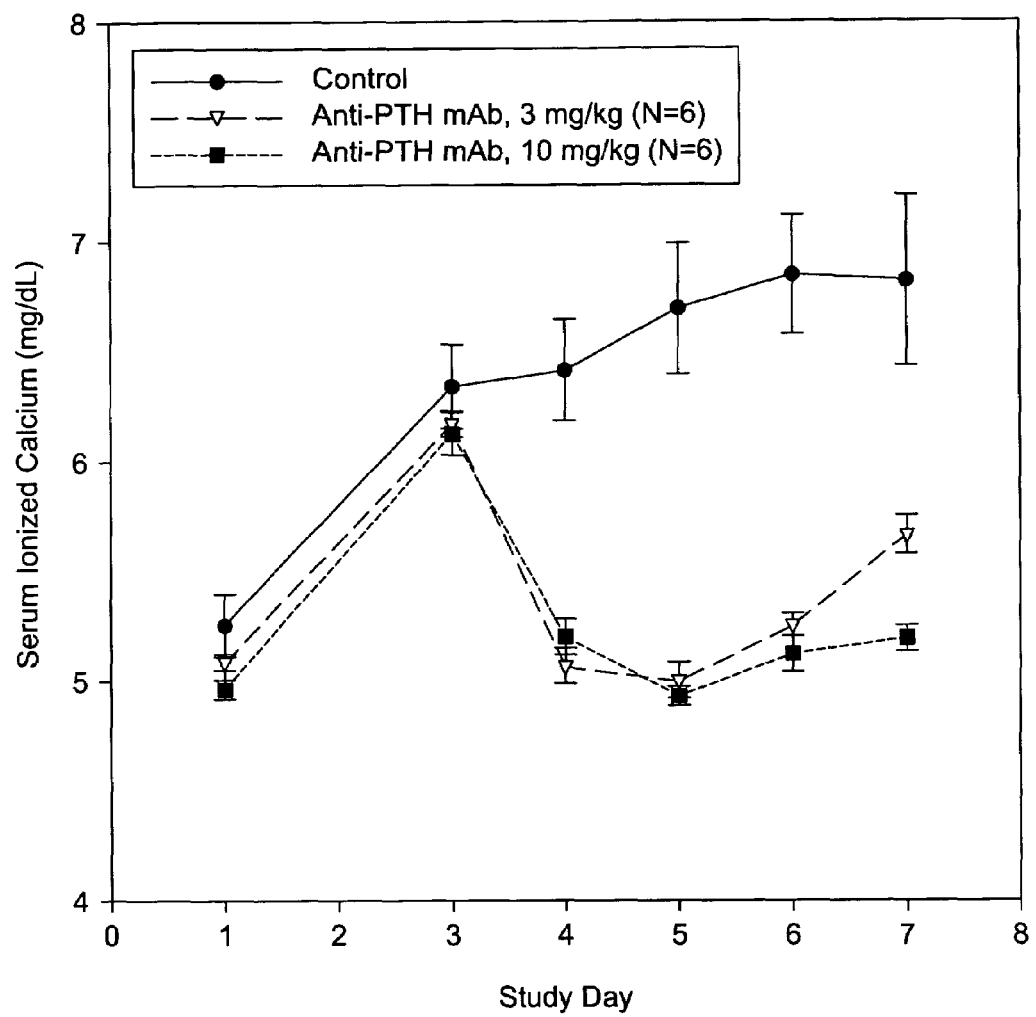
FIG. 2 is a graph showing neutralization of human PTH in vivo by anti-PTH mAb 183 as measured by reversal of a hypercalcemic response to infused human PTH (34mer) in rats.

Neutralization in vivo of PTH bioactivity with anti-PTH mAb 183. The ability of anti-PTH mAb 183 to neutralize human PTH in vivo was assessed by infusing the synthetic human PTH 34mer into rats and subsequently administering anti-PTH mAb 183 or PBS. The 34mer was administered subcutaneously via a 1-week osmotic pump (50 mcg/kg/day) starting on Study Day 1. The hypercalcemic response to the infused PTH was used as a biomarker to assess neutralization of PTH bioactivity by the anti-PTH antibody. Anti-PTH mAb 183 (3 or 10 mg/kg) or an isotype matched control antibody (PK 16.3.1, 10 mg/kg) was administered on Study Day 3 after severe hypercalcemia had developed in the rats. Anti-PTH mAb 183 reversed the hypercalcemic effects of infused PTH for the entire course of the experiment at both dose levels (FIG. 2).

Example 3

Structural Analysis of Anti-PTH Antibodies

The variable heavy chains and the variable light chains for the antibodies shown in Table 1 above were sequenced to determine their DNA sequences. The complete sequence information for all anti-PTH antibodies are shown in the sequence listing submitted herewith, including nucleotide and amino acid sequences for each gamma and kappa chain combination.

The variable heavy chain nucleotide sequences were analyzed to determine the VH family, the D-region sequence and the J-region sequence. The sequences were then translated to determine the primary amino acid sequence and compared to the germline VH, D and J-region sequences to assess somatic hypermutations. The primary amino acid sequences of all the anti-PTH heavy chains are shown in FIG. 3. The germline sequences are shown above and the mutations are indicated with the new amino acid sequence. Amino acids in the sequence that were identical to the indicated germline sequence are indicated with a dash (-). The light chain was analyzed similarly to determine the V and the J-regions and to identify any somatic mutations from germline light chain sequences (FIG. 4).

Example 4

Use of Anti-PTH Antibodies as a Diagnostic Agent

Detection of PTH Antigen in a Sample

An Enzyme-Linked Immunosorbent Assay (ELISA) for the detection of PTH antigen in a sample may be developed. In the assay, wells of a microtiter plate, such as a 96-well microtiter plate or a 384-well microtiter plate, are adsorbed for several hours with a first monoclonal antibody directed against the antigen. The immobilized antibody serves as a capture antibody for any of the antigen that may be present in a test sample. The wells are rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample may be, for example, a serum sample from a subject suspected of having levels of circulating antigen considered to be diagnostic of pathology.

After rinsing away the test sample or standard, the wells are treated with a second fully human monoclonal anti-PTH antibody that is labeled by conjugation with biotin. The labeled anti-PTH antibody serves as a detecting antibody. After rinsing away excess second antibody, the wells are treated with avidin-conjugated horseradish peroxidase (HRP) and a suitable chromogenic substrate. The concentration of the antigen in the test samples is determined by comparison with a standard curve developed from the standard samples.

This ELISA assay provides a highly specific and very sensitive assay for the detection of the PTH antigen in a test sample.

Determination of PTH Concentration in a Patient Sample

A sandwich ELISA is developed to quantify PTH levels in human blood serum. The two monoclonal anti-PTH antibodies used in the sandwich ELISA, recognize different epitopes on the PTH molecule. The ELISA is performed as follows: 50 µl of capture anti-PTH antibody in coating buffer (0.1 M $NaHCO_3$, pH 9.6) at a concentration of 2 µg/mL is coated on ELISA plates (Fisher). After incubation at 4° C. overnight, the plates are treated with 200 µl of blocking buffer (0.5% BSA, 0.1% Tween 20, 0.01% Thimerosal in PBS) for 1 hr at 25° C. The plates are washed (3×) using 0.05% Tween 20 in PBS (washing buffer, WB). Normal or patient sera (Clinomics, Bioreclaimation) are diluted in blocking buffer containing 50% human serum. The plates are incubated with serum samples overnight at 4° C., washed with WB, and then incubated with 100 µl/well of biotinylated detection anti-PTH antibody for 1 hr at 25° C. After washing, the plates are incubated with HRP-Streptavidin for 15 min, washed as before, and then treated with 100 µl/well of o-phenylenediamine in $H_2O_2$ (Sigma developing solution) for color generation. The reaction is stopped with 50 µl/well of $H_2SO_4$ (2M) and analyzed using an ELISA plate reader at 492 nm. Concentration of PTH antigen in serum samples is calculated by comparison to dilutions of purified PTH antigen using a four-parameter curve-fitting program.

Example 5

Use of Anti-PTH Antibodies to Treat Secondary Hyperparathyroidism

To determine the in vivo effects of anti-PTH antibody treatment in human patients with secondary hyperparathyroidism, a number of human patients with end-stage renal disease are enrolled in a study. The selected patients are on dialysis for at least four months prior to enrollment. The patients each have a history of elevated serum PTH values of greater than 400 pg/mL when not receiving therapy.

Patients are injected over a certain amount of time with an effective amount of anti-PTH antibody or placebo containing similar excepients as used to formulate anti-PTH antibody. At periodic times during the treatment, the patients are monitored to determine levels of serum calcium, phosphorus, osteocalcin, bone alkaline phosphatase, unbound active PTH, total PTH (antibody bound and unbound), and radial, hip and spinal bone mineral density.

Analysis of the clinical data shows that anti-PTH antibody significantly reduces the level of circulating active PTH as determined in the above example. Treated patients also show significant decreases in the serum levels of osteocalcin and bone alkaline phosphatase. Treated patients may demonstrate transient reductions in serum calcium following the first dose or with dose escalation. Over time, radial, hip and spinal bone mineral density will increase compared to baseline in untreated patients. In contrast, patients treated with placebo maintain increased levels of circulating PTH, and persistent or decreasing bone mineral density.

The foregoing written specification is considered to be sufficient to enable one skilled in the art to practice the invention. The invention described herein is not to be limited in scope by the construct deposited, since the deposited embodiment is intended as a single illustration of certain embodiments of the invention and any constructs that are functionally equivalent are within the scope of this invention. The deposit of material herein does not constitute an admission that the written description herein contained is inadequate to enable the practice of any embodiment of the invention, including the best mode thereof, nor is it to be construed as limiting the scope of the claims to the specific illustrations that it represents.

All references cited herein, including patents, patent applications, papers, text books, and the like, and the references cited therein, to the extent that they are not already, are hereby incorporated herein by reference in their entirety.

The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. An isolated human monoclonal antibody or binding fragment thereof, that binds to human parathyroid hormone (PTH) and comprises a heavy chain polypeptide comprising the sequence of SEQ ID NO:2 and a light chain polypeptide comprising the sequence of SEQ ID NO:4.

2. A composition, comprising the isolated antibody, or binding fragment thereof, of claim 1 and a pharmaceutically acceptable carrier.

3. The antibody, or binding fragment thereof, of claim 1, wherein the antibody is monoclonal antibody 183.

4. An isolated fully human monoclonal antibody, or binding fragment thereof, that binds to human parathyroid hormone (PTH) with a dissociation constant ($K_D$) of less than about $10^{-9}$ M, wherein said antibody or binding fragment thereof comprises a heavy chain polypeptide comprising the sequence of SEQ ID NO: 2, and wherein the antibody or binding fragment thereof comprises a light chain polypeptide comprising the sequence of SEQ ID NO: 4.

5. The antibody, or binding fragment thereof, of claim 4, wherein said $K_D$ is less than about $10^{-10}$ M.

6. The antibody, or binding fragment thereof of claim 5, wherein said antibody is anti-PTH mAb 183.

7. An isolated fully human monoclonal antibody, or binding fragment thereof, that binds to human parathyroid hormone (PTH), wherein the antibody, or binding fragment thereof, binds an epitope contained within amino acids 18-34 of human PTH (SEQ ID NO: 81), wherein said antibody or binding fragment thereof comprises a heavy chain polypeptide comprising the sequence of SEQ ID NO: 2, and a light chain polypeptide comprising the sequence of SEQ ID NO: 4.

8. The antibody, or binding fragment thereof, of claim 7, wherein the antibody, or binding fragment thereof, binds to PTH with a $K_D$ of less than 100 pM.

9. The antibody, or binding fragment thereof, of claim 7, wherein the antibody, or binding fragment thereof, binds to PTH with a $K_D$ of about 80 pM or less.

10. The antibody, or binding fragment thereof, of claim 7, wherein the antibody, or binding fragment thereof, binds to PTH with a $K_D$ of about 60 pM or less.

11. The antibody, or binding fragment thereof, of claim 7, wherein the antibody, or binding fragment thereof, binds to PTH with a $K_D$ of about 40 pM or less.

12. The antibody, of claim 7, where said antibody is a complete antibody.

13. The antibody, of claim 12, wherein the antibody is monoclonal antibody 183.

14. The antibody, of claim 13, wherein the monoclonal antibody 183 is in admixture with a pharmaceutically acceptable carrier.

15. The antibody, or binding fragment thereof, of claim 7, wherein said binding fragment is a binding fragment selected from the group consisting of Fab, Fab', F(ab')$_2$, and Fv.

16. An isolated antibody immobilized on an insoluble matrix, wherein the antibody is the antibody of claim 7.

* * * * *

UNITED STATES PATENT AND TRADEMARK OFFICE
CERTIFICATE OF CORRECTION

PATENT NO. : 7,288,253 B2
APPLICATION NO. : 10/638265
DATED : October 30, 2007
INVENTOR(S) : Roskos et al.

Page 1 of 1

It is certified that error appears in the above-identified patent and that said Letters Patent is hereby corrected as shown below:

Title Page; item (56);
On page 3, Col. 2 (Other Publications), line 9, please delete "hormones's" and insert --hormone's--, therefor.

On page 3, Col. 2 (Other Publications), line 13, after "region" please insert --of--.

In Col. 1, line 40, please delete "124-647" and insert --1246-47--, therefor.

In Col. 19, line 48 (approx.), please delete "Mol" and insert --Mol..--, therefor.

In Col. 25, line 33, please delete "naive" and insert --naïve--, therefor.

In Col. 38, line 15, please delete "naive" and insert --naïve--, therefor.

In Col. 42, line 61, please delete "11 µg/mL)" and insert --1 µg/mL)--, therefor.

Signed and Sealed this

Twenty-sixth Day of August, 2008

JON W. DUDAS
*Director of the United States Patent and Trademark Office*

SEQUENCE LISTING

<160> NUMBER OF SEQ ID NOS: 97

<210> SEQ ID NO 1
<211> LENGTH: 360
<212> TYPE: DNA
<213> ORGANISM: Homosapien

<400> SEQUENCE: 1

```
gaggtgcagc tggtgcagtc tggagcagag gtgaaaaagc ccggggagtc tctgaagatc      60
tcctgtaagg gttctggata cagctttacc agctactgga tcggctgggt gcgccagatg     120
cccgggaaag gcctggagtg gatggggatc atctctcctg gtgactctga taccagatac     180
agcccgtcct tccaaggcca ggtcaccatc tcagccgaca gtccatcag caccgcctac      240 ctgcagtgga gcagcctgaa ggcctcggac accgccatgt attactgtgc gagacagggg     300
gattacgttt gggggagcta tgactcctgg ggccaggaa ccctggtcac cgtctcctca      360
```

<210> SEQ ID NO 2
<211> LENGTH: 120
<212> TYPE: PRT
<213> ORGANISM: Homosapien

<400> SEQUENCE: 2

```
Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Ser Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Gly Asp Tyr Val Trp Gly Ser Tyr Asp Ser Trp Gly Gln
            100                 105                 110

Gly Thr Leu Val Thr Val Ser Ser
        115                 120
```

<210> SEQ ID NO 3
<211> LENGTH: 333
<212> TYPE: DNA
<213> ORGANISM: Homosapien

<400> SEQUENCE: 3

```
gatattgtga tgacccagac tccactctct ctgtccgtca cccctggacg gccggcctcc      60
atctcctgta gtctagtca gagcctcctg atagtgatg aaagaccta tttgtattgg       120 tacctgcaga agccaggcca gcctccacag ctcctgatct atgaagtttc caaccggttc     180
tctggagtgc cagataggtt cagtggcagc gggtcaggga cagatttcac actgagaatc     240
agccgggtgg aggctgagga tgttggattt tatttctgca tgccaagtat acatctgtgg     300
acgttcggcc aagggaccaa ggtggaaatc aaa                                   333
```

<210> SEQ ID NO 4
<211> LENGTH: 111
<212> TYPE: PRT
<213> ORGANISM: Homosapien

<400> SEQUENCE: 4

Asp Ile Val Met Thr Gln Thr Pro Leu Ser Leu Ser Val Thr Pro Gly
1               5                   10                  15

Arg Pro Ala Ser Ile Ser Cys Lys Ser Gln Ser Leu Leu Asp Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Ile Tyr Phe Cys Met Pro Ser
                85                  90                  95

Ile His Leu Trp Thr Phe Gly Gln Gly Thr Lys Val Glu Ile Lys
            100                 105                 110

<210> SEQ ID NO 5
<211> LENGTH: 351
<212> TYPE: DNA
<213> ORGANISM: Homosapien

<400> SEQUENCE: 5
gaggtgcagc tggtggagtc tgggggaggc ttggtaaagc ctgggggtc ccttagactc      60 tcctgtgcag cctctggatt cactttcagt aacgcctgga tgagctgggt ccgccaggct    120
ccagggaagg ggctggagtg ggttggccgt attaaaagca aaactgatgg tgggacaaca    180
gactacgctg cacccgtgaa aggcagattc aacatctcaa gagatgattc aaaaaatacg    240
ctgtatctgc aaatgaacag cctgaaaacc gaggacacag ccgtgtatta ctgtaccacg    300
ggagctactt ttgactcctg gggccaggga accctggtca ccgtctcctc a             351

<210> SEQ ID NO 6
<211> LENGTH: 117
<212> TYPE: PRT
<213> ORGANISM: Homosapien

<400> SEQUENCE: 6

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Asn Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Gly Ala Thr Phe Asp Ser Trp Gly Gln Gly Thr Leu
            100                 105                 110

Val Thr Val Ser Ser
            115

<210> SEQ ID NO 7
<211> LENGTH: 337
<212> TYPE: DNA
<213> ORGANISM: Homosapien

<400> SEQUENCE: 7

```
gatattgtga tgactcagtc tccactctcc ctgcccgtca cccctggaga gccggcctcc      60
atctcctgca ggtctagtca gagcctcctg catagtaatg gatacaaata tttggattgg     120
ttcctgcaga agccagggca gtctccacag ctcctgatct atttgggttc tattcgggcc     180 tccgggggtcc ctgacaggtt cagtggcagt ggatcaggca cagattttac actgaaaatc    240
agcagagtgg aggctgagga tgttggggtt tattactgca tgcaagctct gcaaactccg     300
tggacgttcg gccaagggac caaggtggaa atcaaac                              337
```

<210> SEQ ID NO 8
<211> LENGTH: 112
<212> TYPE: PRT
<213> ORGANISM: Homosapien

<400> SEQUENCE: 8

```
Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
             20                  25                  30

Asn Gly Tyr Lys Tyr Leu Asp Trp Phe Leu Gln Lys Pro Gly Gln Ser
         35                  40                  45

Pro Gln Leu Leu Ile Tyr Leu Gly Ser Ile Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Trp Thr Phe Gly Gln Gly Thr Lys Val Glu Ile Lys
            100                 105                 110
```

<210> SEQ ID NO 9
<211> LENGTH: 352
<212> TYPE: DNA
<213> ORGANISM: Homosapien

<400> SEQUENCE: 9

```
gaggtgcagc tggtggagtc tgggggaggc ttggtaaagc ctggggagtc ccttagactc      60
tcctgtgcag cctctggatt cactttcagt aacgcctgga tgagctgggt ccgccaggct    120
ccagggaagg ggctggagtg ggttggccgt attaaaagca aaactgatgg tgggacaaca    180
gactacgctg cacccgtgaa aggcagattc accatctcaa gagatgattc aaaaaacacg    240
ctgtatctgc aaatgaacag cctgaaaacc gaggacacag ccgtgtatta ctgtaccacg    300
ggagctactt ttgactcctg gggccaggga accctggtca ccgtctcctc ag            352
```

<210> SEQ ID NO 10
<211> LENGTH: 117
<212> TYPE: PRT
<213> ORGANISM: Homosapien

<400> SEQUENCE: 10

```
Glu Val Gln Leu Val Glu Ser Gly Gly Gly Leu Val Lys Pro Gly Glu
  1               5                  10                  15
```

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
            85                  90                  95

Tyr Cys Thr Thr Gly Ala Thr Phe Asp Ser Trp Gly Gln Gly Thr Leu
            100                 105                 110

Val Thr Val Ser Ser
        115

<210> SEQ ID NO 11
<211> LENGTH: 337
<212> TYPE: DNA
<213> ORGANISM: Homosapien

<400> SEQUENCE: 11
gatattgtga tgactcagtc tccactctcc ctgcccgtca cccctggaga gccggcctcc      60
atctcctgca ggtctagtca gagcctcctg tatagtaatg gatacaaata tttggattgg     120
tacctgcaga agccaggtca gtctccacag ctcctgatct atttgggttc ttatcgggcc     180
tccggggtcc ctgacaggtt cagtggcagt ggatcaggca cagattttac actgaaaatc     240
agcagagtgg aggctgagga tgttggggtt tattactgca tgcaagctct acaaactccg     300
tggacgttcg gccaagggac caaggtggaa atcaaac                              337

<210> SEQ ID NO 12
<211> LENGTH: 112
<212> TYPE: PRT
<213> ORGANISM: Homosapien

<400> SEQUENCE: 12

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Asn Gly Tyr Lys Tyr Leu Asp Trp Tyr Leu Gln Lys Pro Gly Gln Ser
        35                  40                  45

Pro Gln Leu Leu Ile Tyr Leu Gly Ser Tyr Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
            85                  90                  95

Leu Gln Thr Pro Trp Thr Phe Gly Gln Gly Thr Lys Val Glu Ile Lys
            100                 105                 110

<210> SEQ ID NO 13
<211> LENGTH: 352
<212> TYPE: DNA
<213> ORGANISM: Homosapien

<400> SEQUENCE: 13
gaggtgcagc tggtggagtc tgggggaggc ttggtaaagc ctggggggtc ccttagactc      60

```
tcctgtgcag cctctggatt cactttcagg aacgcctgga tgagttgggt ccgccaggct        120
ccagggaagg ggttggagtg ggttggccgt attaaaagca aaactgatgg tgggacaaca        180
gactacgctg cacccgtgaa aggcagattc accatctcaa gagatgattc aaaaaacacg        240
ctgtatctgc aaatgaacag cctgaaaacc gaggacacag ccttgtatta ctgtaccacg        300
ggagctactt ttgactgctg gggccaggga accctggtca ccgtctcctc tg                352
```

<210> SEQ ID NO 14
<211> LENGTH: 117
<212> TYPE: PRT
<213> ORGANISM: Homosapien

<400> SEQUENCE: 14

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Arg Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Leu Tyr
                85                  90                  95

Tyr Cys Thr Thr Gly Ala Thr Phe Asp Cys Trp Gly Gln Gly Thr Leu
            100                 105                 110

Val Thr Val Ser Ser
        115
```

<210> SEQ ID NO 15
<211> LENGTH: 337
<212> TYPE: DNA
<213> ORGANISM: Homosapien

<400> SEQUENCE: 15

```
gatattgtga tgactcagtc tccactctcc ctgcccgtca cccctggaga gccggcctcc        60
atctcctgca ggtctagtca gagcctcctg catagtaatg gatacaacta tttggattgg       120
ttcctgcaga agccagggca gtctccacag ctcctgatct atttgggttc ttatcgggcc       180
tccggggtcc ctgacaggtt cagtggcagt ggatcaggca cagattttac actgaaaatc       240
agcagagtgg aggctgagga tgttggaatt tattattgca tgcaagctcg acaaactccg       300
tggacgttcg gccaagggac caaggtggaa atcaaac                                337
```

<210> SEQ ID NO 16
<211> LENGTH: 112
<212> TYPE: PRT
<213> ORGANISM: Homosapien

<400> SEQUENCE: 16

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Phe Leu Gln Lys Pro Gly Gln Ser
        35                  40                  45
```

```
Pro Gln Leu Leu Ile Tyr Leu Gly Ser Tyr Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Arg Gln Thr Pro Trp Thr Phe Gly Gln Gly Thr Lys Val Glu Ile Lys
            100                 105                 110
```

<210> SEQ ID NO 17
<211> LENGTH: 352
<212> TYPE: DNA
<213> ORGANISM: Homosapien

<400> SEQUENCE: 17

```
caggtgcagc tggtggagtc tgggggaggc gtggtccagc ctgggaggtc cctgagactc    60
tcctgtgcag cctctggatt caccttcagt agctatggca tgcactgggt ccgccaggct   120
ccaggcaagg ggctggactg ggtggcagtt atatcatatg atggaagtaa taaattctat   180
gcagactccg tgaagggccg attcaccatc tccagagaca attccaagaa cacgctgtat   240
ctgcaaatga acagcctgag agctgaggac acggctgtgt attactgtgc gagagaccat   300
tgggagctac ttgactactg gggccaggga accctggtca ccgtctcctc ag           352
```

<210> SEQ ID NO 18
<211> LENGTH: 117
<212> TYPE: PRT
<213> ORGANISM: Homosapien

<400> SEQUENCE: 18

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Asp Trp Val
        35                  40                  45

Ala Val Ile Ser Tyr Asp Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp His Trp Glu Leu Leu Asp Tyr Trp Gly Gln Gly Thr Leu
            100                 105                 110

Val Thr Val Ser Ser
        115
```

<210> SEQ ID NO 19
<211> LENGTH: 337
<212> TYPE: DNA
<213> ORGANISM: Homosapien

<400> SEQUENCE: 19

```
gatattgtga tgacccagac tccactctct ctgtccgtca cacctggaca gccggcctcc    60
atctcctgca agtctagtca gagcctcctg gatagtgatg gaaagaccta tttgtattgg   120
tacttgcaga ggtcaggcca gcctccacag ctcctgatcc atgaagtttc caaccggttt   180
```

| | | |
|---|---|---|
| tctggagtgc catataggtt cattggcagc gggtcaggga cagatttcac actgaaaatc | 240 |
| agccgggtgg aggctgagga tgttggggct tattactgca tgcagggtaa acagtttcca | 300 |
| ttcattttcg gccctgggac caaagtggat atcaaac | 337 |

<210> SEQ ID NO 20
<211> LENGTH: 112
<212> TYPE: PRT
<213> ORGANISM: Homosapien

<400> SEQUENCE: 20

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Tyr Trp Tyr Leu Gln Arg Ser Gly Gln Pro
        35                  40                  45

Pro Gln Leu Leu Ile His Glu Val Ser Asn Arg Phe Ser Gly Val Pro
    50                  55                  60

Tyr Arg Phe Ile Gly Ser Gly Ser Gly Thr Asp Phe Thr Leu Lys Ile
65                  70                  75                  80

Ser Arg Val Glu Ala Glu Asp Val Gly Ala Tyr Tyr Cys Met Gln Gly
                85                  90                  95

Lys Gln Phe Pro Phe Ile Phe Gly Pro Gly Thr Lys Val Asp Ile Lys
            100                 105                 110

<210> SEQ ID NO 21
<211> LENGTH: 352
<212> TYPE: DNA
<213> ORGANISM: Homosapien

<400> SEQUENCE: 21

| | | |
|---|---|---|
| gaggtgcagc tggtggagtc tgggggaggc ttggtaaagc ctgggggtc ccttacactc | 60 |
| tcctgtgcag cctctggatt cactttcagt aacgcctggc tgagctgggt ccgccaggct | 120 |
| ccagggaagg gactggagtg ggttggccgt attaaaagca aaactgatgg tgggacaaca | 180 |
| gactacgctg cacccgtgaa aggcagattc accgtctcaa gagatgattc aaaaaacacg | 240 |
| ctgtttctgc aaatgaacag cctgaaaacc gaggacacag ccgtgtatta ctgtaccacg | 300 |
| ggagctactt tgactcctg gggccaggga accctggtca ccgtctcctc ag | 352 |

<210> SEQ ID NO 22
<211> LENGTH: 117
<212> TYPE: PRT
<213> ORGANISM: Homosapien

<400> SEQUENCE: 22

Glu Val Gln Leu Val Glu Ser Gly Gly Gly Leu Val Lys Pro Gly Gly
1               5                   10                  15

Ser Leu Thr Leu Ser Cys Ala Ala Ser Gly Phe Thr Phe Ser Asn Ala
            20                  25                  30

Trp Leu Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Val Ser Arg Asp Asp Ser Lys Asn Thr
65                  70                  75                  80

Leu Phe Leu Gln Met Asn Ser Leu Lys Thr Glu Asp Thr Ala Val Tyr 85                  90                  95
Tyr Cys Thr Thr Gly Ala Thr Phe Asp Ser Trp Gly Gln Gly Thr Leu
                100                 105                 110
Val Thr Val Ser Ser
        115

<210> SEQ ID NO 23
<211> LENGTH: 337
<212> TYPE: DNA
<213> ORGANISM: Homosapien

<400> SEQUENCE: 23
gatattgtga tgactcagtc tccactctcc ctgcccgtca cccctggaga gccggcctcc      60
atctcctgca ggtctagtca gagcctccta catagtaatg gatacaaatt tttggattgg     120
ttcctgcaga agccagggca gtctccacag ctcctgatct atttgggttc ttatcgggcc     180 tccgggcc ctgacaggtt cagtggcagt ggatcaggca cagattttac actgacaatc      240
agcagagtgg aggctgagga tgttggggtt tattactgca tgcaagctct acaaactccg     300
tggacgttcg gccaagggac caaggtggaa atcaaac                              337

<210> SEQ ID NO 24
<211> LENGTH: 112
<212> TYPE: PRT
<213> ORGANISM: Homosapien

<400> SEQUENCE: 24

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

Asn Gly Tyr Lys Phe Leu Asp Trp Phe Leu Gln Lys Pro Gly Gln Ser
        35                  40                  45

Pro Gln Leu Leu Ile Tyr Leu Gly Ser Tyr Arg Ala Ser Gly Val Pro
    50                  55                  60

Asp Arg Phe Ser Gly Ser Gly Ser Gly Thr Asp Phe Thr Leu Thr Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

<210> SEQ ID NO 25
<211> LENGTH: 351
<212> TYPE: DNA
<213> ORGANISM: Homosapien

<400> SEQUENCE: 25
gaggtgcagc tggtggagtc tgggggaggc ttggtaaagc ctggggggtc ccttagactc      60
tcctgtgcag cctctggatt cactttcagt aacgcctgga tgagctgggt ccgccaggct     120
ccagggaagg ggctggactg ggttggccgt attaaaagca aaactgatgg tgggacaaca     180
gactacgctg cacccgtgaa aggcagattc accatctcaa gagatgattc aaaaaacacg     240
ctgtatctgc aaatgaacag cctgaaaacc gaggacacag ccgtgtatta ctgtaccacg     300
ggagctactt ttgactcctg gggccaggga accctggtca ccgtctcctc a              351

<210> SEQ ID NO 26

<211> LENGTH: 117
<212> TYPE: PRT
<213> ORGANISM: Homosapien

<400> SEQUENCE: 26

| Glu | Val | Gln | Leu | Val | Glu | Ser | Gly | Gly | Gly | Leu | Val | Lys | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Asn | Ala |
|---|---|---|---|---|---|---|---|---|---|---|---|---|---|---|---|
| | | | 20 | | | | | 25 | | | | | 30 | | |

| Trp | Met | Ser | Trp | Val | Arg | Gln | Ala | Pro | Gly | Lys | Gly | Leu | Asp | Trp | Val |
|---|---|---|---|---|---|---|---|---|---|---|---|---|---|---|---|
| | | 35 | | | | | 40 | | | | | 45 | | | |

| Gly | Arg | Ile | Lys | Ser | Lys | Thr | Asp | Gly | Gly | Thr | Thr | Asp | Tyr | Ala | Ala |
|---|---|---|---|---|---|---|---|---|---|---|---|---|---|---|---|
| 50 | | | | | 55 | | | | | 60 | | | | | |

| Pro | Val | Lys | Gly | Arg | Phe | Thr | Ile | Ser | Arg | Asp | Asp | Ser | Lys | Asn | Thr |
|---|---|---|---|---|---|---|---|---|---|---|---|---|---|---|---|
| 65 | | | | | 70 | | | | | 75 | | | | | 80 |

| Leu | Tyr | Leu | Gln | Met | Asn | Ser | Leu | Lys | Thr | Glu | Asp | Thr | Ala | Val | Tyr |
|---|---|---|---|---|---|---|---|---|---|---|---|---|---|---|---|
| | | | | 85 | | | | | 90 | | | | | 95 | |

| Tyr | Cys | Thr | Thr | Gly | Ala | Thr | Phe | Asp | Ser | Trp | Gly | Gln | Gly | Thr | Leu |
|---|---|---|---|---|---|---|---|---|---|---|---|---|---|---|---|
| | | | 100 | | | | | 105 | | | | | 110 | | |

| Val | Thr | Val | Ser | Ser |
|---|---|---|---|---|
| | | | | 115 |

<210> SEQ ID NO 27
<211> LENGTH: 337
<212> TYPE: DNA
<213> ORGANISM: Homosapien

<400> SEQUENCE: 27

| gatattgtga tgactcagtc tccactctcc ctgcccgtca cccctggaga gccggcctcc | 60 |
| atctcctgca ggtctagtca gagcctccta catagtaatg gatacaaatt tttggattgg | 120 |
| ttcctgcaga agccagggca gtctccacag ctcctgatct atttgggttc ttatcgggcc | 180 |
| tccggggtcc ctgacaggtt cagtggccgt ggatcaggca cagattttac actgaaaatc | 240 |
| agcagagtgg aggctgagga tgttggggtt tattactgca tgcaagctct acaaactccg | 300 |
| tggacgttcg gccaagggac caaggtggaa atcaaac | 337 |

<210> SEQ ID NO 28
<211> LENGTH: 112
<212> TYPE: PRT
<213> ORGANISM: Homosapien

<400> SEQUENCE: 28

| Asp | Ile | Val | Met | Thr | Gln | Ser | Pro | Leu | Ser | Leu | Pro | Val | Thr | Pro | Gly |
|---|---|---|---|---|---|---|---|---|---|---|---|---|---|---|---|
| 1 | | | | 5 | | | | | 10 | | | | | 15 | |

| Glu | Pro | Ala | Ser | Ile | Ser | Cys | Arg | Ser | Ser | Gln | Ser | Leu | Leu | His | Ser |
|---|---|---|---|---|---|---|---|---|---|---|---|---|---|---|---|
| | | | 20 | | | | | 25 | | | | | 30 | | |

| Asn | Gly | Tyr | Lys | Phe | Leu | Asp | Trp | Phe | Leu | Gln | Lys | Pro | Gly | Gln | Ser |
|---|---|---|---|---|---|---|---|---|---|---|---|---|---|---|---|
| | | 35 | | | | | 40 | | | | | 45 | | | |

| Pro | Gln | Leu | Leu | Ile | Tyr | Leu | Gly | Ser | Tyr | Arg | Ala | Ser | Gly | Val | Pro |
|---|---|---|---|---|---|---|---|---|---|---|---|---|---|---|---|
| 50 | | | | | 55 | | | | | 60 | | | | | |

| Asp | Arg | Phe | Ser | Gly | Arg | Gly | Ser | Gly | Thr | Asp | Phe | Thr | Leu | Lys | Ile |
|---|---|---|---|---|---|---|---|---|---|---|---|---|---|---|---|
| 65 | | | | | 70 | | | | | 75 | | | | | 80 |

| Ser | Arg | Val | Glu | Ala | Glu | Asp | Val | Gly | Val | Tyr | Tyr | Cys | Met | Gln | Ala |
|---|---|---|---|---|---|---|---|---|---|---|---|---|---|---|---|
| | | | | 85 | | | | | 90 | | | | | 95 | |

| Leu | Gln | Thr | Pro | Trp | Thr | Phe | Gly | Gln | Gly | Thr | Lys | Val | Glu | Ile | Lys |
|---|---|---|---|---|---|---|---|---|---|---|---|---|---|---|---|
| | | | 100 | | | | | 105 | | | | | 110 | | |

<210> SEQ ID NO 29
<211> LENGTH: 352
<212> TYPE: DNA
<213> ORGANISM: Homosapien

<400> SEQUENCE: 29

| | | | | | |
|---|---|---|---|---|---|
| gaggtgcagc | tggtggagtc | tgggggaggc | ttggtaaagc | ctgggggtc | ccttagactc | 60 |
| tcctgtgcag | cctctggatt | cactttcagt | aacgcctgga | tgagctgggt | ccgtcaggct | 120 |
| ccagggaagg | ggctggagtg | ggttggccgt | attaaaagca | aaactgatgg | tgggacaaca | 180 |
| gactacgctg | cacccgtgaa | aggcagattc | accatctcaa | gagatgattc | aaaaaaaacg | 240 |
| ctgtatctgc | aaatgaacag | cctgaaaacc | gaggacacag | ccgtgtatta | ctgtaccacg | 300 |
| ggagctactt | ttgactcctg | gggccaggga | accctggtca | ccgtctcctc | ag | 352 |

<210> SEQ ID NO 30
<211> LENGTH: 117
<212> TYPE: PRT
<213> ORGANISM: Homosapien

<400> SEQUENCE: 30

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Lys Thr
65                  70                  75                  80

Leu Tyr Leu Gln Met Asn Ser Leu Lys Thr Glu Asp Thr Ala Val Tyr
                85                  90                  95

Tyr Cys Thr Thr Gly Ala Thr Phe Asp Ser Trp Gly Gln Gly Thr Leu
            100                 105                 110

Val Thr Val Ser Ser
        115

<210> SEQ ID NO 31
<211> LENGTH: 337
<212> TYPE: DNA
<213> ORGANISM: Homosapien

<400> SEQUENCE: 31

| | | | | | |
|---|---|---|---|---|---|
| gatattgtga | tgactcagtc | tccactctcc | ctgcccgtca | cccctggaga | gccggcctcc | 60 |
| atctcctgca | ggtctagtca | gagcctcctg | catagtaatg | gatacaaata | tttggattgg | 120 |
| ttcctgcaga | agccagggca | gtctccacag | ctcctgatct | atttggggttc | taatcgggcc | 180 |
| tccggggtcc | ctgacaggtt | cagtggcagt | ggatcaggca | cagatttac | actgaaaatc | 240 |
| agcagagtgg | aggctgagga | tgttggggtt | tattactgca | tgcaagctct | acaaactccg | 300 |
| tggacgttcg | gccaagggac | caaggtggaa | atcaaac | | | 337 |

<210> SEQ ID NO 32
<211> LENGTH: 112
<212> TYPE: PRT
<213> ORGANISM: Homosapien

<400> SEQUENCE: 32

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

Asn Gly Tyr Lys Tyr Leu Asp Trp Phe Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110
```

<210> SEQ ID NO 33
<211> LENGTH: 352
<212> TYPE: DNA
<213> ORGANISM: Homosapien

<400> SEQUENCE: 33

```
gaggtgcagc tggtggagtc tgggggaggc ttggtaaagc ctgggggtc ccttagactc      60
tcctgtgcag cctctggatt cactttcagt aacgcctgga tgagctgggt ccgccaggct    120
ccagggaagg ggctggagtg ggttggccgt attaaaagca aaactgatgg tgggacaaca    180
gactacgctg cacccgtgaa aggcagattc accatctcaa gagatgattc aaaaaccacg    240
ctgtatctgc aaatgaacag cctgaaaacc gaggacacag ccgtgtatta ctgtaccacg    300
ggagctactt ttgactcctg gggccaggga accctggtca ccgtctcctc ag            352
```

<210> SEQ ID NO 34
<211> LENGTH: 117
<212> TYPE: PRT
<213> ORGANISM: Homosapien

<400> SEQUENCE: 34

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Thr Thr
65                  70                  75                  80

Leu Tyr Leu Gln Met Asn Ser Leu Lys Thr Glu Asp Thr Ala Val Tyr
                85                  90                  95

Tyr Cys Thr Thr Gly Ala Thr Phe Asp Ser Trp Gly Gln Gly Thr Leu
            100                 105                 110

Val Thr Val Ser Ser
        115
```

<210> SEQ ID NO 35
<211> LENGTH: 337
<212> TYPE: DNA
<213> ORGANISM: Homosapien

-continued

<400> SEQUENCE: 35

```
gatattgtga tgactcagtc tccactctcc ctgcccgtca cccctggaga gccggcctcc     60
atctcctgca ggtctagtca gagcctcctg tatagtaatg gattcaaata tttggattgg    120
ttcctgcaga agccaggtca gtctccacag ctcctgatct atttgggttc ttatcgggcc    180
tccggggtcc ctgacaggtt cagtggcagt ggatcaggca cagattttac actgaaaatc    240
agcagagtgg aggctgagga tgttggggtt tattactgca tgcaagctct acaaactccg    300
tggacgttcg gccaagggac caaggtggaa atcaaac                              337
```

<210> SEQ ID NO 36
<211> LENGTH: 112
<212> TYPE: PRT
<213> ORGANISM: Homosapien

<400> SEQUENCE: 36

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu Tyr Ser
            20                  25                  30

Asn Gly Phe Lys Tyr Leu Asp Trp Phe Leu Gln Lys Pro Gly Gln Ser
        35                  40                  45

Pro Gln Leu Leu Ile Tyr Leu Gly Ser Tyr Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110
```

<210> SEQ ID NO 37
<211> LENGTH: 370
<212> TYPE: DNA
<213> ORGANISM: Homosapien

<400> SEQUENCE: 37

```
gaggtgcagc tggtggagtc tgggggaggc ttggtaaagc ctggggggtc ccttagactc     60
tcctgtgcag cctctggact cactttcagt aacgcctgga tgagctgggt ccgccaggct    120
ccagggaagg ggctggagtg ggttggccgt attaaaagca aaactgatgg tgggacaaca    180
gactacgctg cacccgtgaa aggcagattc accatctcaa gagatgattc aaaaaacacg    240
ctgtatctgc aaatgaacag cctgaaaacc gaggacacag ccgtgtatta ctgtaccacg    300
tattactttg atagtagtgg ttttcctttt gactactgga gccagggaac cctggtcacc    360
gtctcctcag                                                            370
```

<210> SEQ ID NO 38
<211> LENGTH: 123
<212> TYPE: PRT
<213> ORGANISM: Homosapien

<400> SEQUENCE: 38

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Leu Thr Phe Ser Asn Ala
            20                  25                  30
```

```
Trp Met Ser Trp Val Arg Gln Ala Pro Gly Lys Gly Leu Glu Trp Val
            35                  40                  45

Gly Arg Ile Lys Ser Lys Thr Asp Gly Gly Thr Thr Asp Tyr Ala Ala
        50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                    85                  90                  95

Tyr Cys Thr Thr Tyr Tyr Phe Asp Ser Ser Gly Phe Pro Phe Asp Tyr
                100                 105                 110

Trp Ser Gln Gly Thr Leu Val Thr Val Ser Ser
            115                 120
```

<210> SEQ ID NO 39
<211> LENGTH: 337
<212> TYPE: DNA
<213> ORGANISM: Homosapien

<400> SEQUENCE: 39

```
gatattgtaa tgactcagtc tccactctcc ctgcccgtca cccctggaga gccggcctcc    60
atctcctgca ggtctagtca gagcctcctg catagtaatg gatacaagta tttggagtgg   120
tacctgcaga agccagggca gtctccacag ctcctgatct atttgggttc taatcgggcc   180
tccggggtcc ctgacaggtt cagtggcagt ggatcaggca cagattttac actgaaaatc   240
agcagagtgg aggccgagga tgttggggtt tattactgca tgcaaactct acaaattccg   300
ctcactttcg gcggagggac caaggtggag atcaaac                            337
```

<210> SEQ ID NO 40
<211> LENGTH: 112
<212> TYPE: PRT
<213> ORGANISM: Homosapien

<400> SEQUENCE: 40

```
Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
                20                  25                  30

Asn Gly Tyr Lys Tyr Leu Glu Trp Tyr Leu Gln Lys Pro Gly Gln Ser
            35                  40                  45

Pro Gln Leu Leu Ile Tyr Leu Gly Ser Asn Arg Ala Ser Gly Val Pro
         50                 55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Thr
                 85                 90                  95

Leu Gln Ile Pro Leu Thr Phe Gly Gly Gly Thr Lys Val Glu Ile Lys
                100                 105                 110
```

<210> SEQ ID NO 41
<211> LENGTH: 352
<212> TYPE: DNA
<213> ORGANISM: Homosapien

<400> SEQUENCE: 41

```
gaggtgcagc tggtggagtc tgggggaggc ttggtaaagc cggggggtc ccttagactc     60
tcctgtgcag cctctggatt cactttcagt aacgcctgga tgagctgggt ccgccaggct   120
```

```
ccagggaagg ggctggagtg ggttggccgt attaaaagca aaactgatgg tgggacaaca      180
gactacgctg cacccgtgaa aggcagattc accatctcaa gagatgattc agaaaacacg      240
ctgtatctgc aaatgaacgg cctgaaaacc gaggacacag ccgtgtatta ctgtaccacg      300
ggagctactt tgactcctg gggccaggga accctggtca ccgtctcctc ag              352
```

<210> SEQ ID NO 42
<211> LENGTH: 117
<212> TYPE: PRT
<213> ORGANISM: Homosapien

<400> SEQUENCE: 42

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Glu Asn Thr
65                  70                  75                  80

Leu Tyr Leu Gln Met Asn Gly Leu Lys Thr Glu Asp Thr Ala Val Tyr
                85                  90                  95

Tyr Cys Thr Thr Gly Ala Thr Phe Asp Ser Trp Gly Gln Gly Thr Leu
            100                 105                 110

Val Thr Val Ser Ser
        115
```

<210> SEQ ID NO 43
<211> LENGTH: 337
<212> TYPE: DNA
<213> ORGANISM: Homosapien

<400> SEQUENCE: 43

```
gatattgtga tgactcagtc tccactctcc ctgcccgtca cccctggaga gccggcctcc      60
atctcctgca ggtctagtca gagcctcctg cgtagtaatg gatacaacta tttggattgg      120
ttcctgcaga agccagggca gtctccacag ctcctgatct atttgggttc tgttcgggcc      180
tccggggtcc ctgacaggtt cagtggcagt ggatcgggca cagattttac actgaaaatc      240
agcagagtgg aggctgagga tgttggggtt tattactgca tgcaagctct acaaactccg      300
tggacgttcg gccaagggac caaggtggaa atcaaac                               337
```

<210> SEQ ID NO 44
<211> LENGTH: 112
<212> TYPE: PRT
<213> ORGANISM: Homosapien

<400> SEQUENCE: 44

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu Arg Ser
            20                  25                  30

Asn Gly Tyr Asn Tyr Leu Asp Trp Phe Leu Gln Lys Pro Gly Gln Ser
        35                  40                  45

Pro Gln Leu Leu Ile Tyr Leu Gly Ser Val Arg Ala Ser Gly Val Pro
```

```
                50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Trp Thr Phe Gly Gln Gly Thr Lys Val Glu Ile Lys
            100                 105                 110
```

<210> SEQ ID NO 45
<211> LENGTH: 370
<212> TYPE: DNA
<213> ORGANISM: Homosapien

<400> SEQUENCE: 45

| | | | | | |
|---|---|---|---|---|---|
| gaggtgcagc | tggtggagtc | tgggggaggc | ttggtaaagc | ctggggggtc | ccttagactc | 60 |
| tcctgtgcag | cctctggact | cactttcagt | aacgcctgga | tgagctgggt | ccgccaggct | 120 |
| ccagggaagg | ggctggagtg | ggttggccgt | attaaaagca | aaagtgatgg | tgggacaaca | 180 |
| gactacgctg | cacccgtgaa | aggcagattc | accatctcaa | gagatgattc | aaaaaacacg | 240 |
| ctgtatctgc | aaatgaacag | cctgaaaacc | gaggacacag | ccgtgtatta | ctgtaccacg | 300 |
| tattactttg | atagtagtgg | ttttcctttt | gactactgga | gccagggaac | cctggtcacc | 360 |
| gtctcctcag | | | | | | 370 |

<210> SEQ ID NO 46
<211> LENGTH: 123
<212> TYPE: PRT
<213> ORGANISM: Homosapien

<400> SEQUENCE: 46

```
Glu Val Gln Leu Val Glu Ser Gly Gly Gly Leu Val Lys Pro Gly Gly
  1               5                  10                  15

Ser Leu Arg Leu Ser Cys Ala Ala Ser Gly Leu Thr Phe Ser Asn Ala
                 20                  25                  30

Trp Met Ser Trp Val Arg Gln Ala Pro Gly Lys Gly Leu Glu Trp Val
             35                  40                  45

Gly Arg Ile Lys Ser Lys Ser Asp Gly Gly Thr Thr Asp Tyr Ala Ala
         50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr Tyr Tyr Phe Asp Ser Ser Gly Phe Pro Phe Asp Tyr
            100                 105                 110

Trp Ser Gln Gly Thr Leu Val Thr Val Ser Ser
            115                 120
```

<210> SEQ ID NO 47
<211> LENGTH: 337
<212> TYPE: DNA
<213> ORGANISM: Homosapien

<400> SEQUENCE: 47

| | | | | | |
|---|---|---|---|---|---|
| gatattgtga | tgactcagtc | tccactctcc | ctgcccgtca | cccctggaga | gccggcctcc | 60 |
| atctcctgca | ggtctagtca | gagcctcctg | catagtaatg | gatacaagta | tttggagtgg | 120 |
| tacctgcaga | agccagggca | gtctccacag | ctcctgatct | atttgggttc | taatcgggcc | 180 |

```
tccggggtcc ctgacaggtt cagtggcagt ggatcaggca cagattttac actgaaaatc    240
agcagagtgg aggctgagga tgttggggtt tattactgca tgcaaactct acaaattccg    300
ctcactttcg gcggagggac caaggtggag atcaaac                             337
```

<210> SEQ ID NO 48
<211> LENGTH: 112
<212> TYPE: PRT
<213> ORGANISM: Homosapien
<400> SEQUENCE: 48

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

Asn Gly Tyr Lys Tyr Leu Glu Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Leu Gln Ile Pro Leu Thr Phe Gly Gly Gly Thr Lys Val Glu Ile Lys
            100                 105                 110
```

<210> SEQ ID NO 49
<211> LENGTH: 370
<212> TYPE: DNA
<213> ORGANISM: Homosapien
<400> SEQUENCE: 49

```
gaggtgcagc tggtggagtc tgggggaggc ttggtaaagc ctggggggtc ccttagactc     60
tcctgtgcag cctctggatc cactttcagt aacgcctgga tgagctgggt ccgccaggct    120
ccagggaagg ggctggagtg ggttggccgt attaaaagca gaactgatgg tgggacagca    180
gactacgctg cacccgtgaa aggcagattc accatctcaa gagatgattt aaaaaaaacg    240
ctgtatctgc aaatgaacag cctgaaaacc gaggacacag ccgtgtatta ctgtaccacg    300
tattactttg atagtagtgg ttttcctttt gactactggg gccagggaac cctggtcacc    360
gtctcctcag                                                           370
```

<210> SEQ ID NO 50
<211> LENGTH: 123
<212> TYPE: PRT
<213> ORGANISM: Homosapien
<400> SEQUENCE: 50

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Ser Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Arg Thr Asp Gly Gly Thr Ala Asp Tyr Ala Ala
    50                  55                  60

Pro Val Lys Gly Arg Phe Thr Ile Ser Arg Asp Asp Leu Lys Lys Thr
65                  70                  75                  80
```

-continued

Leu Tyr Leu Gln Met Asn Ser Leu Lys Thr Glu Asp Thr Ala Val Tyr
                85                  90                  95

Tyr Cys Thr Thr Tyr Tyr Phe Asp Ser Ser Gly Phe Pro Phe Asp Tyr
            100                 105                 110

Trp Gly Gln Gly Thr Leu Val Thr Val Ser Ser
        115                 120

<210> SEQ ID NO 51
<211> LENGTH: 337
<212> TYPE: DNA
<213> ORGANISM: Homosapien

<400> SEQUENCE: 51
gatattgtga tgactcagtc tccactctac ctgcccgtca cccctggaga gccggcctcc      60
atctcctgca ggtctagtca gagcctcctg catagtaatg gatacaagta tttggagtgg     120
tacctgcaga agccagggca gtctccacag ctcctggtct atttgggttc taatcgggcc     180
tccggggtcc ctgacaggtt cagtggcagt ggatcaggca cagatttac actgaaaatc      240 agcagagtgg aggctgagga tgttggggtt tattactgca tgcaagctct acaaactccg     300
ctcactttcg gcggagggac caaggtggag atcaaac                              337

<210> SEQ ID NO 52
<211> LENGTH: 112
<212> TYPE: PRT
<213> ORGANISM: Homosapien

<400> SEQUENCE: 52

Asp Ile Val Met Thr Gln Ser Pro Leu Tyr Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Lys Tyr Leu Glu Trp Tyr Leu Gln Lys Pro Gly Gln Ser
        35                  40                  45

Pro Gln Leu Leu Val Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 53
<211> LENGTH: 370
<212> TYPE: DNA
<213> ORGANISM: Homosapien

<400> SEQUENCE: 53
gaggtgcagc tggtggagtc tgggggaggc ttggtaaagc ctggggggtc ccttagactc      60
tcctgtgcag cctctggact cactttcagt aacgcctgga tgagctgggt ccgccaggct     120
ccagggaagg ggctggagtg ggttggccgt attaaaagca aaactaatgg tggacaaca      180 gactacgctg cacccgtgaa aggcagattc accatctcaa gagatgattc aaaaaacacg     240
ctgtatctgc aaatgaacag cctgaaaacc gaggacacag ccgtgtatta ctgtaccacg     300
tattactttg atagtagtgg ttttcctttt gactactgga gccagggaac cctggtcacc     360

-continued gtctcctcag    370

<210> SEQ ID NO 54
<211> LENGTH: 123
<212> TYPE: PRT
<213> ORGANISM: Homosapien

<400> SEQUENCE: 54

Glu Val Gln Leu Val Glu Ser Gly Gly Gly Leu Val Lys Pro Gly Gly
1               5                   10                  15

Ser Leu Arg Leu Ser Cys Ala Ala Ser Gly Leu Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asn Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Tyr Tyr Phe Asp Ser Ser Gly Phe Pro Phe Asp Tyr
            100                 105                 110

Trp Ser Gln Gly Thr Leu Val Thr Val Ser Ser
        115                 120

<210> SEQ ID NO 55
<211> LENGTH: 337
<212> TYPE: DNA
<213> ORGANISM: Homosapien

<400> SEQUENCE: 55
gagattgtga tgacgcagtc tccactcaac ctgcccgtca cccctggaga gccggcctcc    60
atctcctgca ggtccagtca gagcctcctg catagtaatg gatacaagta tttggagtgg    120
tacctgcaga agccagggca gtctccacag ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tgcaaactct acaaattccg    300
ctcactttcg gcggagggac caaggtggag atcaaac    337

<210> SEQ ID NO 56
<211> LENGTH: 112
<212> TYPE: PRT
<213> ORGANISM: Homosapien

<400> SEQUENCE: 56

Glu Ile Val Met Thr Gln Ser Pro Leu Asn Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Lys Tyr Leu Glu Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

```
Leu Gln Ile Pro Leu Thr Phe Gly Gly Gly Thr Lys Val Glu Ile Lys
            100                 105                 110
```

<210> SEQ ID NO 57
<211> LENGTH: 352
<212> TYPE: DNA
<213> ORGANISM: Homosapien

<400> SEQUENCE: 57

```
gaaatgcagc tggtggagtc tgggggaggc ttggtaaagc ctggggggtc ccttagactc      60
tcctgtgcag cctctggatt cactttcagt agcgcctgga tgaactgggt ccgccaggct     120
ccagggaagg ggctggagtg ggttggccgt attaaaagca aaactgatgg tgggacaaca     180
gactacgctg cacccgtgaa aggcagattc accatctcaa gggatgattc aaaaaactca     240
ctttatctgg aaatgaacag cctgaaaacc gaggacacag ccgtgtatca ctgttccaca     300
ggggctgtcc ttgactactg gggccaggga accctggtca ccgtctcctc aa             352
```

<210> SEQ ID NO 58
<211> LENGTH: 117
<212> TYPE: PRT
<213> ORGANISM: Homosapien

<400> SEQUENCE: 58

```
Glu Met Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Ala
            20                  25                  30

Trp Met Asn Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Ser
65                  70                  75                  80

Leu Tyr Leu Glu Met Asn Ser Leu Lys Thr Glu Asp Thr Ala Val Tyr
                85                  90                  95

His Cys Ser Thr Gly Ala Val Leu Asp Tyr Trp Gly Gln Gly Thr Leu
            100                 105                 110

Val Thr Val Ser Ser
        115
```

<210> SEQ ID NO 59
<211> LENGTH: 338
<212> TYPE: DNA
<213> ORGANISM: Homosapien

<400> SEQUENCE: 59

```
gatattgtga tgactcagtc tccactctcc ctgcccgtca cccctggaga gccggcctcc      60
atctcctgca ggtccagtca gaacctcctg cgtagtaatg gatacaacta tttggaatgg     120
tacctgcaga agccagggca gtctccacag ctcctgatct atttgggttc taatcgggcc     180
tccggggtcc ctgacaggtt cagtggcagt ggatcaggca cagatttttc actgaaaatc     240
agcagagtgg aggctgagga tgttggggtt tattactgca tgcaatctct acaaactcct     300
ctcactttcg gcggtgggac caaggtggag atcaaacg                              338
```

<210> SEQ ID NO 60
<211> LENGTH: 112

```
<212> TYPE: PRT
<213> ORGANISM: Homosapien

<400> SEQUENCE: 60

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Asn Leu Leu Arg Ser
            20                  25                  30

Asn Gly Tyr Asn Tyr Leu Glu Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Ser Leu Lys Ile
65                  70                  75                  80

Ser Arg Val Glu Ala Glu Asp Val Gly Val Tyr Tyr Cys Met Gln Ser
                85                  90                  95

Leu Gln Thr Pro Leu Thr Phe Gly Gly Gly Thr Lys Val Glu Ile Lys
            100                 105                 110

<210> SEQ ID NO 61
<211> LENGTH: 361
<212> TYPE: DNA
<213> ORGANISM: Homosapien

<400> SEQUENCE: 61
gaggtgcagc tggtgcagtc tggagcagag gtgaaaaagc ccggggagtc tctgaagatc      60
tcctgtaagg gttctagata catctttacc aactactgga tcggctgggt gcgccagatg     120
cccgggaaag gcctggagtg gatggggatc atctatcctg gtgactctga taccagatat     180
agcccgtcct tccaaggcca ggtcaccatc tcagccgaca tgtccatcag caccgcctac     240
ctgcagtgga gcagcctgaa ggcctcggac accgccatgt attactgtgc gagacagggg     300
gattacgttt ggggagcttt tgactcctgg ggccaggaa ccctggtcac cgtctcctca     360
g                                                                       361

<210> SEQ ID NO 62
<211> LENGTH: 120
<212> TYPE: PRT
<213> ORGANISM: Homosapien

<400> SEQUENCE: 62

Glu Val Gln Leu Val Gln Ser Gly Ala Glu Val Lys Lys Pro Gly Glu
1               5                   10                  15

Ser Leu Lys Ile Ser Cys Lys Gly Ser Arg Tyr Ile Phe Thr Asn Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Met Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Gly Asp Tyr Val Trp Gly Ser Phe Asp Ser Trp Gly Gln
            100                 105                 110

Gly Thr Leu Val Thr Val Ser Ser
            115                 120
```

<210> SEQ ID NO 63
<211> LENGTH: 334
<212> TYPE: DNA
<213> ORGANISM: Homosapien

<400> SEQUENCE: 63

| | | | | | |
|---|---|---|---|---|---|
| gatattgtga | tgacccagac | tccactctct | ctgtccgtca | cccctggaca | gccggcctcc | 60 |
| atctcctgca | agtctagtca | gagcctcctg | gatagtgatg | gaaagaccta | tttgtattgg | 120 |
| tacctgcaga | agccaggcca | gcctccacag | ctcctgatct | atgaagtttc | caaccggttc | 180 |
| tctggagtgc | cagataggtt | cagtggcagc | gggtcaggga | cagatttcac | actgaaaatc | 240 |
| agccgggtgg | aggctgagga | tgttggggtt | tattactgca | tgcaaagtat | acagctgtgg | 300 |
| acgttcggcc | aagggaccaa | ggtggaaatc | aaac | | | 334 |

<210> SEQ ID NO 64
<211> LENGTH: 111
<212> TYPE: PRT
<213> ORGANISM: Homosapien

<400> SEQUENCE: 64

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Trp Thr Phe Gly Gln Gly Thr Lys Val Glu Ile Lys
            100                 105                 110

<210> SEQ ID NO 65
<211> LENGTH: 352
<212> TYPE: DNA
<213> ORGANISM: Homosapien

<400> SEQUENCE: 65

| | | | | | |
|---|---|---|---|---|---|
| gaggtgcagc | tggtggagtc | tgggggaggc | ttggtaaagc | ctggggggtc | ccttagactc | 60 |
| tcctgtgcag | cctctggatt | cactttcagt | aacgcctgga | tgagctgggt | ccgccaggct | 120 |
| ccagggaagg | ggctgagtg | ggttggccgt | attaaaagca | aaagtgatgg | tgggacaaca | 180 |
| gactacgctg | cacccgtgaa | aggcagattc | accatctcaa | gagatgattc | aaaaaacacg | 240 |
| ctgtatctgc | aaatgaacag | cctgaaaacc | gaggacacag | ccgtgtatta | ctgtaccacg | 300 |
| ggagctactt | ttgactcctg | gggccaggga | accctggtca | ccgtctcctc | ag | 352 |

<210> SEQ ID NO 66
<211> LENGTH: 117
<212> TYPE: PRT
<213> ORGANISM: Homosapien

<400> SEQUENCE: 66

Glu Val Gln Leu Val Glu Ser Gly Gly Gly Leu Val Lys Pro Gly Gly

```
  1               5                   10                  15
Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
            35                  40                  45

Gly Arg Ile Lys Ser Lys Ser Asp Gly Gly Thr Thr Asp Tyr Ala Ala
            50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                85                  90                  95

Tyr Cys Thr Thr Gly Ala Thr Phe Asp Ser Trp Gly Gln Gly Thr Leu
            100                 105                 110

Val Thr Val Ser Ser
            115
```

<210> SEQ ID NO 67
<211> LENGTH: 337
<212> TYPE: DNA
<213> ORGANISM: Homosapien

<400> SEQUENCE: 67

```
gatattgtga tgactcagtc tccactctcc ctgcccgtca cccctggaga gccggcctcc    60
atctcctgca ggtctagtca gagcctcctg catagaaatg gatacaaata tttggattgg   120
tacctgcaga agccagggca gtctccacag ctcctgatct atttgggttc ttatcgggcc   180
tccggggtcc ctgacaggtt cagtggcagt ggatcaggca cagattctac actgaaaatc   240
agcagagtgg aggctgagga tgttggggtt tattactgca tgcaagctct acaaactccg   300
tggacgttcg gccaagggac caaggtggaa atcaaac                            337
```

<210> SEQ ID NO 68
<211> LENGTH: 112
<212> TYPE: PRT
<213> ORGANISM: Homosapien

<400> SEQUENCE: 68

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Arg
            20                  25                  30

Asn Gly Tyr Lys Tyr Leu Asp Trp Tyr Leu Gln Lys Pro Gly Gln Ser
            35                  40                  45

Pro Gln Leu Leu Ile Tyr Leu Gly Ser Tyr Arg Ala Ser Gly Val Pro
            50                  55                  60

Asp Arg Phe Ser Gly Ser Gly Ser Gly Thr Asp Ser Thr Leu Lys Ile
 65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110
```

<210> SEQ ID NO 69
<211> LENGTH: 353
<212> TYPE: DNA
<213> ORGANISM: Homosapien

<400> SEQUENCE: 69

```
gaggtgcagc tggtggagtc tggggaggc ttggtaatgc ctgggggtc ccttagactc      60 tcctgtgcag cctctggatt cactttcagt aacgcctgga tgagctgggt ccgccaggct    120
ccagggaagg ggctggactg ggttggccgt attaaaagca aaactgatgg tgggacaaca    180
gactacgctg cacccgtgaa aggcagattc accatctcaa gagatgattc aaaaaacacg    240
ctgtatctgc aaatgaacag cctgaaaacc gaggacacag ccgtgtatta ctgtaccacg    300
ggagctactt ttgactcctg ggccaggga accctggtca ccgtctcatc tcc            353
```

<210> SEQ ID NO 70
<211> LENGTH: 117
<212> TYPE: PRT
<213> ORGANISM: Homosapien

<400> SEQUENCE: 70

```
Glu Val Gln Leu Val Glu Ser Gly Gly Gly Leu Val Met Pro Gly Gly
  1               5                  10                  15

Ser Leu Arg Leu Ser Cys Ala Ala Ser Gly Phe Thr Phe Ser Asn Ala
             20                  25                  30

Trp Met Ser Trp Val Arg Gln Ala Pro Gly Lys Gly Leu Asp Trp Val
         35                  40                  45

Gly Arg Ile Lys Ser Lys Thr Asp Gly Gly Thr Thr Asp Tyr Ala Ala
     50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr Gly Ala Thr Phe Asp Ser Trp Gly Gln Gly Thr Leu
                100                 105                 110

Val Thr Val Ser Ser
            115
```

<210> SEQ ID NO 71
<211> LENGTH: 337
<212> TYPE: DNA
<213> ORGANISM: Homosapien

<400> SEQUENCE: 71

```
gatattgtga tgactcagtc tccactctcc ctgcccgtca cccctggaga gccggcctcc     60
atctcctgca ggtctagtca gagcctccta catagtaatg gatacaaatt tttggattgg    120
ttcctgcaga agccagggca gtctccacag ctcctgatct atttgggttc ttatcgggcc    180
tccggggtcc ctgacaggtt cagtggccgt ggatcaggca cagattttac actgaaaatc    240
agcagagtgg aggctgagga tgttggggtt tattactgca tgcaagctct acaaactccg    300
tggacgttcg gccaagggac caaggtggaa atcaaac                             337
```

<210> SEQ ID NO 72
<211> LENGTH: 112
<212> TYPE: PRT
<213> ORGANISM: Homosapien

<400> SEQUENCE: 72

```
Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
             20                  25                  30
```

```
Asn Gly Tyr Lys Phe Leu Asp Trp Phe Leu Gln Lys Pro Gly Gln Ser
            35                  40                  45

Pro Gln Leu Leu Ile Tyr Leu Gly Ser Tyr Arg Ala Ser Gly Val Pro
        50                  55                  60

Asp Arg Phe Ser Gly Arg Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

<210> SEQ ID NO 73
<211> LENGTH: 358
<212> TYPE: DNA
<213> ORGANISM: Homosapien

<400> SEQUENCE: 73
gaggtgcagc tggtggagtc tgggggagac ttggtacagc ctggggggtc cctgagactc     60
tcctgtgcag cctctggatt caccttcagt agctacgaca tgtactgggt ccgccaagct    120
acaggaaaag gtctggagtg gtctcagct attggtactg ctggtgacac atactatcca    180
ggctccgtga agggccgatt caccatctcc agagaaaatg ccaagaactc cttgtatctt    240
caaatgaaca gcctgagagc cggggacacg gctgtgtatt actgtgcaag agggagcag    300 ttcgtccgag ggcttttga ctactggggc cagggaaccc tggtcaccgt ctcctcag    358

<210> SEQ ID NO 74
<211> LENGTH: 119
<212> TYPE: PRT
<213> ORGANISM: Homosapien

<400> SEQUENCE: 74

Glu Val Gln Leu Val Glu Ser Gly Gly Asp Leu Val Gln Pro Gly Gly
 1               5                  10                  15

Ser Leu Arg Leu Ser Cys Ala Ala Ser Gly Phe Thr Phe Ser Ser Tyr
                20                  25                  30

Asp Met Tyr Trp Val Arg Gln Ala Thr Gly Lys Gly Leu Glu Trp Val
            35                  40                  45

Ser Ala Ile Gly Thr Ala Gly Asp Thr Tyr Tyr Pro Gly Ser Val Lys
        50                  55                  60

Gly Arg Phe Thr Ile Ser Arg Glu Asn Ala Lys Asn Ser Leu Tyr Leu
 65                  70                  75                  80

Gln Met Asn Ser Leu Arg Ala Gly Asp Thr Ala Val Tyr Tyr Cys Ala
                85                  90                  95

Arg Gly Glu Gln Phe Val Arg Gly Leu Phe Asp Tyr Trp Gly Gln Gly
            100                 105                 110

Thr Leu Val Thr Val Ser Ser
            115

<210> SEQ ID NO 75
<211> LENGTH: 322
<212> TYPE: DNA
<213> ORGANISM: Homosapien

<400> SEQUENCE: 75
gacatccaga tgacccagtc tccatcttcc gtgtctgcat ctgtaggaga cagagtcacc     60
atcacttgtc gggcgagtca gggtattagc agctggttag cctggtatca gcagaaacca    120
```

```
gggaaagccc ctaagctcct gatctatgct gcatccattt acaaagtggg ggtcccatca    180
aggttcagcg gcagtggatc tgggacagat ttcactctca ccatcagcag cctgcagcct    240
gaagattttg caacttacta ttgtcaacag gctaacagtt tcccattcac tttcggccct    300
gggaccaaag tggatatcaa ac                                             322
```

<210> SEQ ID NO 76
<211> LENGTH: 107
<212> TYPE: PRT
<213> ORGANISM: Homosapien

<400> SEQUENCE: 76

```
Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ile Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Asp Ile Lys
            100                 105
```

<210> SEQ ID NO 77
<211> LENGTH: 361
<212> TYPE: DNA
<213> ORGANISM: Homosapien

<400> SEQUENCE: 77

```
gaggtgcagc tggtgcagtc tggagcagag gtgaaaaagc ccggggagtc tctgaagatc    60
tcctgtaagg gttctagata catctttacc aactactgga tcggctgggt gcgccagatg   120
cccgggaaag gcctggagtg gatggggatc atctatcctg gtgactctga taccagatat   180
agcccgtcct tccaaggcca ggtcaccatc tcagccgaca tgtccatcag caccgcctac   240
ctgcagtgga gcagcctgaa ggcctcggac accgccatgt attactgtgc gagacagggg   300
gattacgttt ggggagctt tgactcctgg ggccagggaa ccctggtcac cgtctcctca   360
g                                                                   361
```

<210> SEQ ID NO 78
<211> LENGTH: 120
<212> TYPE: PRT
<213> ORGANISM: Homosapien

<400> SEQUENCE: 78

```
Glu Val Gln Leu Val Gln Ser Gly Ala Glu Val Lys Lys Pro Gly Glu
 1               5                  10                  15

Ser Leu Lys Ile Ser Cys Lys Gly Ser Arg Tyr Ile Phe Thr Asn Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
 50                  55                  60
```

Gln Gly Gln Val Thr Ile Ser Ala Asp Met Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Gly Asp Tyr Val Trp Gly Ser Phe Asp Ser Trp Gly Gln
            100                 105                 110

Gly Thr Leu Val Thr Val Ser Ser
        115                 120

<210> SEQ ID NO 79
<211> LENGTH: 333
<212> TYPE: DNA
<213> ORGANISM: Homosapien

<400> SEQUENCE: 79
gatattgtga tgacccagac tccactctct ctgtccgtca cccctggacg gccggcctcc      60
atctcctgta agtctagtca gagcctcctg gatagtgatg aaagaccta tttgtattgg     120 tacctgcaga agccaggcca gcctccacag ctcctgatct atgaagtttc caaccggttc     180
tctggagtgc cagataggtt cagtggcagc gggtcaggga cagatttcac actgagaatc     240
agccgggtgg aggctgagga tgttgggatt tatttctgca tgccaagtat acatctgtgg     300
acgttcggcc aagggaccaa ggtggaaatc aaa                                  333

<210> SEQ ID NO 80
<211> LENGTH: 111
<212> TYPE: PRT
<213> ORGANISM: Homosapien

<400> SEQUENCE: 80

Asp Ile Val Met Thr Gln Thr Pro Leu Ser Leu Ser Val Thr Pro Gly
1               5                   10                  15

Arg Pro Ala Ser Ile Ser Cys Lys Ser Ser Gln Ser Leu Leu Asp Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Ile Tyr Phe Cys Met Pro Ser
                85                  90                  95

Ile His Leu Trp Thr Phe Gly Gln Gly Thr Lys Val Glu Ile Lys
            100                 105                 110

<210> SEQ ID NO 81
<211> LENGTH: 84
<212> TYPE: PRT
<213> ORGANISM: Homosapien

<400> SEQUENCE: 81

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu

```
                    50                  55                  60
Lys Ser Leu Gly Glu Ala Asp Lys Ala Asp Val Asn Val Leu Thr Lys
 65                  70                  75                  80

Ala Lys Ser Gln

<210> SEQ ID NO 82
<211> LENGTH: 34
<212> TYPE: PRT
<213> ORGANISM: Homosapien

<400> SEQUENCE: 82

Ser Val Ser Glu Ile Gln Leu Met His Asn Leu Gly Lys His Leu Asn
  1               5                  10                  15

Ser Met Glu Arg Val Glu Trp Leu Arg Lys Leu Gln Asp Val His
                 20                  25                  30

Asn Phe

<210> SEQ ID NO 83
<211> LENGTH: 78
<212> TYPE: PRT
<213> ORGANISM: Homosapien

<400> SEQUENCE: 83

Leu Met His Asn Leu Gly Lys His Leu Asn Ser Met Glu Arg Val Glu
  1               5                  10                  15

Trp Leu Arg Lys Lys Leu Gln Asp Val His Asn Phe Val Ala Leu Gly
                 20                  25                  30

Ala Pro Leu Ala Pro Arg Asp Ala Gly Ser Gln Arg Pro Arg Lys Lys
         35                  40                  45

Glu Asp Asn Val Leu Val Glu Ser His Glu Lys Ser Leu Gly Glu Ala
     50                  55                  60

Asp Lys Ala Asp Val Asn Val Leu Thr Lys Ala Lys Ser Gln
 65                  70                  75

<210> SEQ ID NO 84
<211> LENGTH: 31
<212> TYPE: PRT
<213> ORGANISM: Homosapien

<400> SEQUENCE: 84

Met Glu Arg Val Glu Trp Leu Arg Lys Lys Leu Gln Asp Val His Asn
  1               5                  10                  15

Phe Val Ala Leu Gly Ala Pro Leu Ala Pro Arg Asp Ala Gly Ser
                 20                  25                  30

<210> SEQ ID NO 85
<211> LENGTH: 34
<212> TYPE: PRT
<213> ORGANISM: Homosapien

<400> SEQUENCE: 85

Ala Val Ser Glu His Gln Leu Leu His Asp Lys Gly Lys Ser Ile Gln
  1               5                  10                  15

Asp Leu Arg Arg Arg Phe Phe Leu His His Leu Ile Ala Glu Ile His
                 20                  25                  30

Thr Ala

<210> SEQ ID NO 86
<211> LENGTH: 84
```

```
<212> TYPE: PRT
<213> ORGANISM: Homosapien

<400> SEQUENCE: 86

Ala Val Ser Glu Ile Gln Leu Met His Asn Leu Gly Lys His Leu Ala
 1               5                  10                  15

Ser Val Glu Arg Met Gln Trp Leu Arg Lys Lys Leu Gln Asp Val His
                20                  25                  30

Asn Phe Val Ser Leu Gly Val Gln Met Ala Ala Arg Glu Gly Ser Tyr
            35                  40                  45

Gln Arg Pro Thr Lys Lys Glu Glu Asn Val Leu Val Asp Gly Asn Ser
        50                  55                  60

Lys Ser Leu Gly Glu Gly Asp Lys Ala Asp Val Asp Val Leu Val Lys
65                  70                  75                  80

Ala Lys Ser Gln

<210> SEQ ID NO 87
<211> LENGTH: 34
<212> TYPE: PRT
<213> ORGANISM: Homosapien

<400> SEQUENCE: 87

Ala Val Ser Glu Ile Gln Leu Met His Asn Leu Gly Lys His Leu Ala
 1               5                  10                  15

Ser Val Glu Arg Met Gln Trp Leu Arg Lys Lys Leu Gln Asp Val His
                20                  25                  30

Asn Phe

<210> SEQ ID NO 88
<211> LENGTH: 84
<212> TYPE: PRT
<213> ORGANISM: Homosapien

<400> SEQUENCE: 88

Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
                20                  25                  30

Asn Phe Ile Ala Leu Gly Ala Pro Leu Ala Pro Arg Asp Ala Gly Ser
            35                  40                  45

Gln Arg Pro Arg Lys Lys Glu Asp Asn Ile Leu Val Glu Ser His Glu
        50                  55                  60

Lys Ser Leu Gly Glu Ala Asp Lys Ala Asp Val Asp Val Leu Thr Lys
65                  70                  75                  80

Ala Lys Ser Gln

<210> SEQ ID NO 89
<211> LENGTH: 10
<212> TYPE: PRT
<213> ORGANISM: Homosapien

<400> SEQUENCE: 89

Gly Tyr Ser Phe Thr Ser Tyr Trp Ile Gly
 1               5                  10

<210> SEQ ID NO 90
<211> LENGTH: 17
<212> TYPE: PRT
<213> ORGANISM: Homosapien
```

```
<400> SEQUENCE: 90

Ile Ile Ser Pro Gly Asp Ser Asp Thr Arg Tyr Ser Pro Ser Phe Gln
1               5                   10                  15
Gly

<210> SEQ ID NO 91
<211> LENGTH: 11
<212> TYPE: PRT
<213> ORGANISM: Homosapien

<400> SEQUENCE: 91

Gln Gly Asp Tyr Val Trp Gly Ser Tyr Asp Ser
1               5                   10

<210> SEQ ID NO 92
<211> LENGTH: 16
<212> TYPE: PRT
<213> ORGANISM: Homosapien

<400> SEQUENCE: 92

Lys Ser Ser Gln Ser Leu Leu Asp Ser Asp Gly Lys Thr Tyr Leu Tyr
1               5                   10                  15

<210> SEQ ID NO 93
<211> LENGTH: 7
<212> TYPE: PRT
<213> ORGANISM: Homosapien

<400> SEQUENCE: 93

Glu Val Ser Asn Arg Phe Ser
1               5

<210> SEQ ID NO 94
<211> LENGTH: 8
<212> TYPE: PRT
<213> ORGANISM: Homosapien

<400> SEQUENCE: 94

Met Pro Ser Ile His Leu Trp Thr
1               5

<210> SEQ ID NO 95
<211> LENGTH: 17
<212> TYPE: PRT
<213> ORGANISM: Homosapien

<400> SEQUENCE: 95

Ile Ile Tyr Pro Gly Asp Ser Asp Thr Arg Tyr Ser Pro Ser Phe Gln
1               5                   10                  15
Gly

<210> SEQ ID NO 96
<211> LENGTH: 12
<212> TYPE: PRT
<213> ORGANISM: Homosapien

<400> SEQUENCE: 96

Tyr Tyr Asp Tyr Val Trp Gly Ser Tyr Ala Tyr Thr
1               5                   10

<210> SEQ ID NO 97
<211> LENGTH: 7
```

```
-continued
<212> TYPE: PRT
<213> ORGANISM: Homosapien

<400> SEQUENCE: 97

Asp Tyr Val Trp Gly Ser Tyr
1               5
```